United States Patent [19]

Lowe, III

[11] Patent Number: 5,643,904

[45] Date of Patent: Jul. 1, 1997

[54] SUBSTITUTED HEXAHDRYOAZEPINONES AND TETRAHYDROBENZAZEPINONES

[75] Inventor: John A. Lowe, III, Stonington, Conn.

[73] Assignee: Pfizer Inc., New York, N.Y.

[21] Appl. No.: 495,283

[22] Filed: Jun. 27, 1995

Related U.S. Application Data

[60] Division of Ser. No. 78,125, filed as PCT/US92/10720 Dec. 16, 1992, Pat. No. 5,484,917, which is a continuation-in-part of Ser. No. 825,677, Jan. 27, 1992, abandoned.

[51] Int. Cl.$^6$ .................. A61K 31/53; C07D 223/16
[52] U.S. Cl. .................. 514/212; 514/213; 540/523; 540/527
[58] Field of Search .................. 540/523, 527; 514/212, 213

[56] References Cited

U.S. PATENT DOCUMENTS 5,484,917  1/1996  Lowe, III .................. 540/523

*Primary Examiner*—Robert T. Bond
*Attorney, Agent, or Firm*—Peter C. Richardson; Paul H. Ginsburg; Garth C. Butterfield

[57] ABSTRACT

The present invention relates to novel substituted hexahydroazepinones and tetrahydrobenzazepinones of the formulae

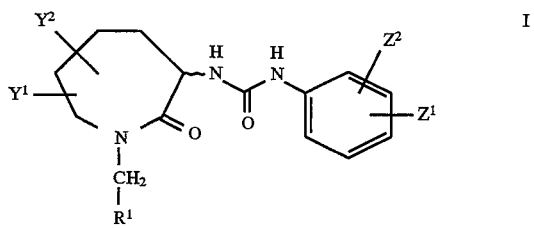

and

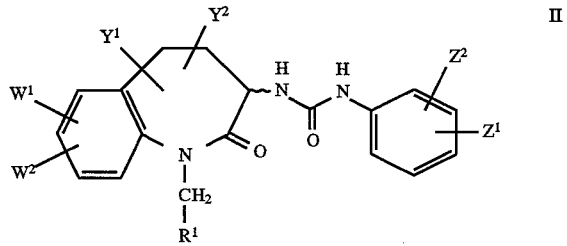

wherein $R^1, Z^1, Z^2, W^1, W^2, Y^1$ and $Y^2$ are as defined below, and to novel intermediates used in the synthesis of such compounds.

Such compounds are useful in the treatment and prevention of gastrointestinal disorders, pain and anxiety disorders.

7 Claims, No Drawings

SUBSTITUTED HEXAHDRYOAZEPINONES AND TETRAHYDROBENZAZEPINONES

This is a division of application Ser. No. 08/078,125, which was filed on Jun. 16, 1993, now U.S. Pat. No. 5,484,917 and which claims priority from international patent application PCT/US 92/10720, which was filed on Dec. 16, 1992 as a continuation-in-part of application Ser. No. 07/825,677, which was filed on Jan. 27, 1992, now abandoned, and from which both international application PCT/US 92/10720, prior application Ser. No. 08/078,125 and the present application claim priority.

BACKGROUND OF THE INVENTION

The present invention relates to novel substituted hexahydroazepinones and tetrahydrobenzazepinones, pharmaceutical compositions comprising such compounds and the use of such compounds in the treatment and prevention of central nervous system and gastrointestinal disorders. The pharmaceutically active compounds of this invention are selective CCK-B receptor antagonists.

Cholecystokinin (CCK) is a 33-amino acid peptide originally discovered and characterized in 1971. (See Mutt et al., Biochem. J., 125, 57 (1971)). It carries out its biological responses by binding to its two receptor types: CCK-A and CCK-B. The CCK-A receptor is located primarily in the gallbladder and pancreas, and mediates CCK-induced enzyme secretion and gallbladder contraction during a meal. The CCK-B receptor is located in the stomach, where it is involved in acid secretion, and in the brain, where it mediates pain and anxiety responses.

A number of potent and selective non-peptide antagonists for these two receptors are known (See M. G. Bock, Drugs of the Future, 16 (7), 631–640 (1991) and R. M. Freidinger, Med. Res. Rev., 9, 271–290 (1989)). Merck's L-364,718 (devazepide) is a selective CCK-A antagonist. (See O'Neill et al., Brain Res., 534, 287–290 (1990)). This compound, however, has proven not to be clinically useful. Merck's benzodiazepine L-365,260 is a selective CCK-B antagonist that was found to have an analgesic effect on squirrel monkeys. (See O'Neill et al., Brain Res., 534, 287–290 (1990)). Clarke-Davis' CI-988 is a selective CCK-B antagonist that was found to reverse the pentagastrin-induced anxiogenic response in rats. (See Singh et al., Proc. Nat'l. Acad. Sci., U.S., 88, 1130–33 (1991)).

SUMMARY OF THE INVENTION

The present invention relates to compounds of the formula

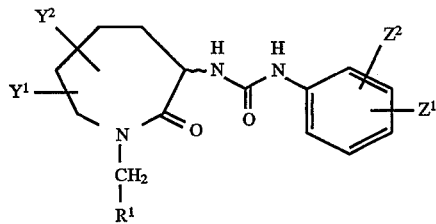

or

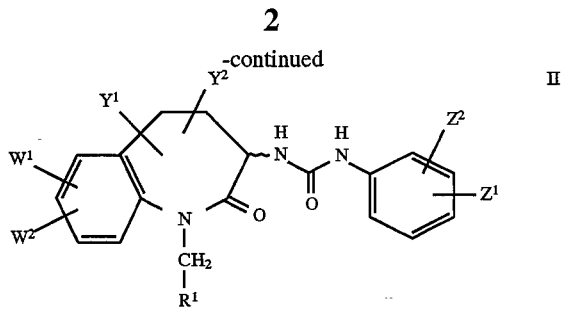

wherein $Y^1$ and $Y^2$ are independently selected from the group consisting of phenyl, thienyl, pyridyl, furyl, pyrimidyl, ($C_3$–$C_8$) straight or branched alkyl and ($C_5$–$C_8$) cycloalkyl, wherein said phenyl, thienyl, pyridyl, furyl, and pyrimidyl may optionally substituted with one or two substituents independently selected from halo (e.g., chloro, fluoro, bromo or iodo), ($C_1$–$C_6$) alkyl, ($C_1$–$C_6$) alkoxy, nitro, amino and trifluoromethyl, and wherein said cycloalkyl may optionally be substituted with one or two substituents independently selected from ($C_1$–$C_6$) alkyl;

$W^1$ and $W^2$ are independently selected from halo, nitro, amino, ($C_1$–$C_6$)alkyl optionally substituted with from one to three fluorine atoms and ($C_1$–$C_6$)alkoxy optionally subsituted with from one to three fluorine atoms;

$Z^1$ and $Z^2$ are independently selected from the group consisting of halo, ($C_1$–$C_6$) alkyl, ($C_1$–$C_6$) thioalkyl, ($C_1$–$C_6$) alkoxy, trifluoromethyl, ($C_1$–$C_6$) carboalkoxy, amino and nitro;

$R^1$ is phenyl, $CO_2R^2$, $SO_2NR^3R^6$ or $CONR^4R^5$, wherein said phenyl may optionally be substituted with one or two substituents independently selected from halo, ($C_1$–$C_6$) alkyl, ($C_1$–$C_6$) alkoxy, nitro, amino and trifluoromethyl, and wherein $R^2$, $R^3$, $R^4$, $R^5$ and $R^6$ are independently selected from hydrogen, ($C_3$–$C_{12}$) alkyl and fused, saturated carbocyclic systems containing two or three rings.

The present invention also relates to the pharmaceutically acceptable acid addition salts of compounds of the formulae I and II. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)] salts.

The term "alkyl", as used herein, unless otherwise indicated, includes saturated monovalent hydrocarbon radicals having straight, branched or cyclic moieties or combinations thereof.

The term "halo", as used herein, unless otherwise indicated, includes chloro, fluoro, bromo and iodo.

Preferred compounds of this invention are compounds of the formula I wherein either both of $Y^1$ and $Y^2$ are phenyl, or one of $Y^1$ and $Y^2$ is cyclohexyl.

Other preferred compounds of this invention are compounds of the formula II wherein $Y^1$ is phenyl.

Preferred compounds of the present invention include the following:

N-tert-butyl-2-[3-(3-(3-thiomethylphenyl)ureido)-2-oxo-5-phenyl-2,3,4,5-tetrahydro-1H-(1)benzazepin-1-yl] ethanoate;

3-((3-chlorophenyl)ureido)-7-cyclohexyl-(N-t-butoxycarbonylmethyl)-hexahydroazepin-2-one;
3-((3-tolyl)ureido)-7-cyclohexyl-(N-t-butoxycarbonylmethyl)hexahydroazepin-2-one;
3-((3-chlorophenyl)ureido)-7-cyclohexyl-(N-1-adamantyloxycarbonylmethyl)-hexahydroazepin-2-one;
3-((3-chlorophenyl)ureido)-7-cyclohexyl-(N-2-adamantyloxycarbonylmethyl)-hexahydroazepin-2-one;
3-((3-tolyl)ureido)-7-cyclohexyl-(N-1-adamantyloxycarbonylmethyl)-hexahydroazepin-2-one;
3-((3-tolyl)ureido)-7-cyclohexyl-(N-2-adamantyloxycarbonylmethyl)-hexahydroazepin-2-one;
3-((3-methoxyphenyl)ureido)-7-cyclohexyl-(N-t-butoxycarbonylmethyl)-hexahydroazepin-2-one;
3-((3-methoxyphenyl)ureido)-7-cyclohexyl-(N-1-adamantyloxycarbonylmethyl)-hexahydroazepin-2-one;
3-((3-methoxyphenyl)ureido)-7-cyclohexyl-(N-2-adamantyloxycarbonylmethyl)-hexahydroazepin-2-one;
3-((3-chlorophenyl)ureido)-5,7-diphenyl-(N-t-butoxycarbonylmethyl)-hexahydroazepin-2-one;
3-((3-tolyl)ureido)-5,7-diphenyl-(N-t-butoxycarbonylmethyl)-hexahydroazepin-2-one;
3-((3-methoxyphenyl)ureido)-5,7-diphenyl-(N-t-butoxycarbonylmethyl)-hexahydroazepin-2-one;
3-((3-chlorophenyl)ureido)-5,7-diphenyl-(N-1-adamantyloxycarbonylmethyl)-hexahydroazepin-2-one;
N-tert-butyl-2-[3-(3-(3-chlorophenyl)ureido)-2-oxo-5-phenyl-2,3,4,5-tetrahydro-1H-(1)benzazepin-1-yl]ethanoic acid amide;
N-tert-butyl-2-[3-(3-(3-chlorophenyl)ureido)-2-oxo-5-phenyl-8-methyl-2,3,4,5-tetrahydro-1H-(1)benzazepin-1-yl]ethanoic acid amide;
N-tert-butyl-2-[3-(3-(3-tolyl)ureido)-2-oxo-5-phenyl-2,3,4,5-tetrahydro-1H-(1)benzazepin-1-yl]ethanoic acid amide;
N-tert-butyl-2-[3-(3-(3-methoxyphenyl)ureido)-2-oxo-5-phenyl-2,3,4,5-tetrahydro-1H-(1)benzazepin-1-yl]ethanoic acid amide;
N-tert-butyl-2-[3-(3-(3-thiomethylphenyl)ureido)-2-oxo-5-phenyl-2,3,4,5,-tetrahydro-1H-(1)benzazepin-1-yl]ethanoic acid amide;
N,N-di(2-propyl)-2-[3-(3-(3-chlorophenyl)ureido)-2-oxo-5-phenyl-2,3,4,5-tetrahydro-1H-(1)benzazepin-1-yl]ethanoic acid amide;
N,N-di(2-propyl)-2-[3-(3-(3-toly)ureido)-2-oxo-5-phenyl-2,3,4,5-tetrahydro-1H-(1)benzazepin-1-yl]ethanoic acid amide;
N,N-di(2-propyl)-2-[3-(3-(3-methoxyphenyl)ureido)-2-oxo-5-phenyl-2,3,4,5-tetrahydro-1H-(1)benzazepin-1-yl]ethanoic acid amide;
N,N-di(2-propyl)-2-[3-(3-(3-thiomethylphenyl)ureido)-2-oxo-5-phenyl-2,3,4,5-tetrahydro-1H-(1)benzazepin-1-yl]ethanoic acid amide;
N-tert-butyl-2-[3-(3-(3-chlorophenyl)ureido)-2-oxo-5-phenyl-2,3,4,5-tetrahydro-1H-(1)benzazepin-1-yl]ethanoate;
N-tert-butyl-2-[3-(3-(3-tolyl)ureido)-2-oxo-5-phenyl-2,3,4,5-tetrahydro-1H-(1)benzazepin-1-yl]ethanoate;
N-tert-butyl-2-[3-(3-(3-methoxyphenyl)ureido)-2-oxo-5-phenyl-2,3,4,5-tetrahydro-1H-(1)benzazepin-1-yl]ethanoate;
N-tert-butyl-2-[2-oxo-3-((3-tolyl)ureido)-5,7-diphenylhexahydroazepin-1-yl]-ethanoic acid amide;
N-tert-butyl-2-[2-oxo-3-((3-chlorophenyl)ureido)-5,7-diphenylhexahydroazepin-1-yl]ethanoic acid amide;
N-tert-butyl-2-[2-oxo-3-((3-methoxyphenyl)ureido)-5,7-diphenylhexahydroazepin-1-yl]ethanoic acid amide;
N-tert-butyl-2-[2-oxo-3-((3-trifluoromethylphenyl)ureido)-5,7-diphenylhexahy-droazepin-1-yl]ethanoic acid amide;
N-tert-butyl-2-[2-oxo-3-((3-methylthiophenyl)ureido)-5,7-diphenyl-hexahydroa-zepin-1-yl]ethanoic acid amide;
N-tert-butyl-2-[2-oxo-3-((3-cyanophenyl)ureido)-5,7-diphenyl-hexahydroazepin-1-yl]ethanoic acid amide;
N-tert-butyl-2-[2-oxo-3-((3-dimethylaminophenyl)ureido)-5,7-diphenyl-hexahydroazepin-1-yl]ethanoic acid amide;
N-tert-butyl-2-[2-oxo-3-((3-ethylphenyl)ureido)-5,7-diphenyl-hexahydroazepin-1-yl]ethanoic acid amide;
N-tert-butyl-2-[2-oxo-3-(3-tolylureido)-5-phenyl-8-methyl-2,3,4,5-tetrahydro-1H-(1)benzazepin-1-yl]ethanoic acid amide;
N-tert-butyl-2-[2-oxo-3-(3-tolylureido)-5-phenyl-9-methyl-2,3,4,5-tetrahydro-1H-(1)benzazepin-1-yl]ethanoic acid amide;
N-tert-butyl-2-[2-oxo-3-(3-tolylureido)-5-phenyl-7-chloro-2,3,4,5-tetrahydro-1H(1)benzazepin-1-yl]ethanoic acid amide;
N-tert-butyl-2-[2-oxo-3-(3-tolylureido)-5-(4-fluorophenyl)-2,3,4,5-tetrahydro-1H-(1)benzazepin-1-yl]ethanoic acid amide;
N-tert-butyl-2-[2-oxo-3-(3-tolylureido)-5-(4-chlorophenyl)-2,3,4,5-tetrahydro-1H-(1)benzazepin-1-yl]ethanoic acid amide;
N-tert-butyl-2-[2-oxo-3-(3-tolylureido)-5-(4-methylphenyl)-2,3,4,5-tetrahydro-1H-(1)benzazepin-1-yl]ethanoic acid amide;
N-tert-butyl-2-[2-oxo-3-(3-tolylureido)-5-(2-fluorophenyl)-2,3,4,5-tetrahydro-1H-(1)benzazepin-1-yl]ethanoic acid amide;
N-tert-butyl-2-[2-oxo-3-(3-tolylureido)-5-(3-chlorophenyl)-2,3,4,5-tetrahydro-1H-(1)benzazepin-1-yl]ethanoic acid amide;
N-tert-butyl-2-[2-oxo-3-(3-tolylureido)-5-(3,4-dichlorophenyl)-2,3,4,5-tetrahydro-1H-(1)benzazepin-1-yl]ethanoic acid amide;
N-(1,1-dimethyl)propyl)-2-[2-oxo-3-((3-tolyl)ureido)-5-phenyl-2,3,4,5-tetrahydro-1H-(1)benzazepin-1-yl]ethanoic acid amide;
(N-(1-methyl)cyclohexyl)-2-[2-oxo-3-((3-tolyl)ureido)-5-phenyl-2,3,4,5-tetrahydro-1H-(1)benzazepin-1-yl]ethanoic acid amide;
N-tert-butyl-2-[2-oxo-3-(3-tolylureido)-5-cyclohexyl-2,3,4,5-tetrahydro-1H-(1)-benzazepin-1-yl]ethanoic acid amide.

Examples of other compounds of the present invention include:

N-tert-butyl-2-[2-oxo-3-((3-tolyl)ureido)-5-phenyl, 7-(3-pyridyl)-hexahydroazepin-1-yl]ethanoic acid amide;
N-tert-butyl-2-[2-oxo-3-((3-tolyl)ureido)-5-phenyl, 7-(2-pyridyl)-hexahydroazepin-1-yl]ethanoic acid amide;
N-tert-butyl-2-[2-oxo-3-((3-tolyl)ureido)-5-phenyl, 7-(4-pyridyl)-hexahydroazepin-1-yl]ethanoic acid amide;
N-tert-butyl-2-[2-oxo-3-((3-tolyl)ureido)-5-phenyl, 7-(3-thienyl)-hexahydroazepin-1-yl]ethanoic acid amide;
N-tert-butyl-2-[2-oxo-3-((3-tolyl)ureido)-5-phenyl, 7-(2-thienyl)-hexahydroazepin-1-yl]ethanoic acid amide;
N-tert-butyl-2-[2-oxo-3-((3-tolyl)ureido)-5-phenyl, 7-(2-pyrimidyl)-hexahydroazepin-1-yl]ethanoic acid amide;
N-tert-butyl-2-[2-oxo-3-((3-tolyl)ureido)-5-phenyl, 7-(4-pyrimidyl)-hexahydroazepin-1-yl]ethanoic acid amide;
N-tert-butyl-2-[2-oxo-3-((3-tolyl)ureido)-5-(3-fluorophenyl), 7-phenyl-hexahydroazepin-1-yl]ethanoic acid amide;
N-tert-butyl-2-[2-oxo-3-((3-tolyl)ureido)-5-(4-chlorophenyl), 7-phenyl-hexahydroazepin-1-yl]ethanoic acid amide;
N-tert-butyl-2-[2-oxo-3-((3-tolyl)ureido)-5-(3-chlorophenyl), 7-phenyl-hexahydroazepin-1-yl]ethanoic acid amide;

N-tert-butyl-2-[2-oxo-3-((3-tolyl)ureido)-5-(3-trifluoromethylphenyl), 7-phenyl-hexahydroazepin-1-yl]ethanoic acid amide;

N-tert-butyl-2-[2-oxo-3-((3-tolyl)ureido)-5-(3-tolyl), 7-phenyl-hexahydroazepin-1-yl]ethanoic acid amide;

N-tert-butyl-2-[2-oxo-3-((3-tolyl)ureido)-5-(4-tolyl), 7-phenyl-hexahydroazepin-1-yl]ethanoic acid amide;

N-tert-butyl-2-[2-oxo-3-((3-tolyl)ureido)-5-(4-methoxyphenyl), 7-phenyl-hexahydroazepin-1-yl]ethanoic acid amide;

N-tert-butyl-2-[2-oxo-3-((3-tolyl)ureido)-5-(3-methoxyphenyl), 7-phenyl-hexahydroazepin-1-yl]ethanoic acid amide;

N-tert-butyl-2-[2-oxo-3-((3-tolyl)ureido)-5-(3-pyridyl), 7-phenyl-hexahydroazepin-1-yl]ethanoic acid amide;

N-tert-butyl-2-[2-oxo-3-((3-tolyl)ureido)-5-(3-thienyl), 7-phenyl-hexahydroazepin-1-yl]ethanoic acid amide;

N-tert-butyl-2-[2-oxo-3-((3-tolyl)ureido)-5-(4-thienyl), 7-phenyl-hexahydroazepin-1-yl]ethanoic acid amide;

N-tert-butyl-2-[2-oxo-3-((3-tolyl)ureido)-5-(2-pyridyl), 7-phenyl-hexahydroazepin-1-yl]ethanoic acid amide;

N-tert-butyl-2-[2-oxo-3-((3-tolyl)ureido)-5-cyclohexyl, 7-phenyl-hexahydroazepin-1-yl]ethanoic acid amide;

N-(1,1-dimethyl)propyl-2-[2-oxo-3-((3-tolyl)ureido)-5,7-diphenyl-hexahydroazepin-1-yl]ethanoic acid amide;

N-(1,1-dimethyl)benzyl-2-[2-oxo-3-((3-tolyl)ureido)-5,7-diphenyl-hexahydroazepin-1-yl]ethanoic acid amide;

N-(1-methyl)cyclohexyl-2-[2-oxo-3-((3-tolyl)ureido)-5,7-diphenyl-hexahydroazepin-1-yl]ethanoic acid amide;

N-(1-methyl)cyclopentyl-2-[2-oxo-3-((3-tolyl)ureido)-5,7-diphenyl-hexahydroazepin-1-yl]ethanoic acid amide;

N-tert-butyl-2-[2-oxo-3-((3-methylaminophenyl)ureido)-5,7-diphenyl-hexahydroaz-epin-1-yl]ethanoic acid amide;

N-tert-butyl-2-[2-oxo-3-((3-(N-methyl,N-acetyl)ureido)-5-cyclohexyl, 7-phenyl-hexahydroazepin-1-yl]ethanoic acid amide;

N-tert-butyl-2-[2-oxo-3-((3-(N-methyl,N-methanesulfonyl)) ureido)-5-cyclohexyl, 7-phenylhexahydroazepin-1-yl]ethanoic acid amide;

N-tert-butyl-2-[2-oxo-3-((3-diethylaminophenyl)ureido)-5, 7-diphenyl-hexahy-droazepin-1-yl]ethanoic acid amide;

N-tert-butyl-2-[2-oxo-3-((3-isopropylaminophenyl)ureido)-5,7-diphenyl-hexahyd-roazepin-1-yl]ethanoic acid amide;

N-tert-butyl-2-[2-oxo-3-((3-t-butylaminophenyl)ureido)-5, 7-diphenyl-hexahydro-azepin-1-yl]ethanoic acid amide;

N-tert-butyl-2-[2-oxo-3-((3-isopropylphenyl)ureido)-5,7-diphenyl-hexahydroazepin-1-yl]ethanoic acid amide;

N-tert-butyl-2-[2-oxo-3-((3-t-butylphenyl)ureido)-5,7-diphenyl-hexahydroazepin-1-yl]ethanoic acid amide;

(N-(1,1-dimethyl)benzyl)-2-[2-oxo-3-((3-tolyl)ureido)-5-phenyl-2,3,4,5-tetrahydro-1H-(1)benzazepin-1-yl]ethanoic acid amide;

(N-(1-methyl)cyclopentyl)-2-[2-oxo-3-((3-tolyl)ureido)-5-phenyl-2,3,4,5-tetrahydro-1H-(1)benzazepin-1-yl]ethanoic acid amide;

N-tert-butyl-2-[2-oxo-3-((3-dimethylaminophenyl)ureido)-5-phenyl-2,3,4,5-tetrahydro-1H-(1)benzazepin-1-yl]ethanoic acid amide;

N-tert-butyl-2-[2-oxo-3-((3-methylaminophenyl)ureido)-5-phenyl-2,3,4,5-tetrahydro-1H-(1)benzazepin-1-yl]ethanoic acid amide;

N-tert-butyl-2-[2-oxo-3-((3-(N-methyl,N-acetyl)ureido)-5-phenyl-2,3,4,5-tetrahydro-1H-(1)benzazepin-1-yl]ethanoic acid amide;

N-tert-butyl-2-[2-oxo-3-((3-(N-methyl,N-methanesulfonyl))ureido)-5-phenyl-2,3,4,5-tetrahydro-1H-(1)benzazepin-1-yl]ethanoic acid amide;

N-tert-butyl-2-[2-oxo-3-((3-diethylaminophenyl)ureido)-5-phenyl-2,3,4,5-tetrahydro-1H-(1)benzazepin-1-yl]ethanoic acid amide;

N-tert-butyl-2-[2-oxo-3-((3-isopropylaminophenyl)ureido)-5-phenyl-2,3,4,5-tetrahydro-1H-(1)benzazepin-1-yl]ethanoic acid amide;

N-tert-butyl-2-[2-oxo-3-((3-t-butylaminophenyl)ureido)-5-phenyl-2,3,4,5-tetrahydro-1H-(1)benzazepin-1-yl]ethanoic acid amide;

N-tert-butyl-2-[2-oxo-3-((3-isopropylphenyl)ureido)-5-phenyl-2,3,4,5-tetrahydro-1H-(1)benzazepin-1-yl]ethanoic acid amide;

N-tert-butyl-2-[2-oxo-3-((3-t-butylphenyl)ureido)-5-phenyl-2,3,4,5-tetrahydro-1H-(1)benzazepin-1-yl]ethanoic acid amide;

N-tert-butyl-2-[2-oxo-3-(3-tolylureido)-5-phenyl-8-methoxy-2,3,4,5-tetrahydro-1H-(1)benzazepin-1-yl]ethanoic acid amide;

N-tert-butyl-2-[2-oxo-3-(3-tolylureido)-5-phenyl-8-ethyl-2,3,4,5-tetrahydro-1H-(1)benzazepin-1-yl]ethanoic acid amide;

N-tert-butyl-2-[2-oxo-3-(3-tolylureido)-5-phenyl-8-fluoro-2,3,4,5-tetrahydro-1H-(1)benzazepin-1-yl]ethanoic acid amide;

N-tert-butyl-2-[2-oxo-3-(3-tolylureido)-5-phenyl-8-chloro-2,3,4,5-tetrahydro-1H-(1)benzazepin-1-yl]ethanoic acid amide;

N-tert-butyl-2-[2-oxo-3-(3-tolylureido)-5-phenyl-7-methoxy-2,3,4,5-tetrahydro-1H-(1)benzazepin-1-yl]ethanoic acid amide;

N-tert-butyl-2-[2-oxo-3-(3-tolylureido)-5-phenyl-7-fluoro-2,3,4,5-tetrahydro-1H-(1)benzazepin-1-yl]ethanoic acid amide;

N-tert-butyl-2-[2-oxo-3-(3-tolylureido)-5-phenyl-7-trifluoromethyl-2,3,4,5-tetra-hydro-1H-(1)benzazepin-1-yl]ethanoic acid amide;

N-tert-butyl-2-[2-oxo-3-(3-tolylureido)-5-phenyl-8-trifluoromethyl-2,3,4,5-tetra-hydro-1H-(1)benzazepin-1-yl]ethanoic acid amide;

N-tert-butyl-2-[2-oxo-3-(3-tolylureido)-5-(3-fluorophenyl)-2,3,4,5-tetrahydro-1H-(1)benzazepin-1-yl]ethanoic acid amide;

N-tert-butyl-2-[2-oxo-3-(3-tolylureido)-5-(3-trifluoromethylphenyl)-2,3,4,5-tetrahydro-1H-(1)benzazepin-1-yl]ethanoic acid amide;

N-tert-butyl-2-[2-oxo-3-(3-tolylureido)-5-(4-trifluoromethylphenyl)-2,3,4,5-tetrahydro-1H-(1)benzazepin-1-yl]ethanoic acid amide;

N-tert-butyl-2-[2-oxo-3-(3-tolylureido)-5-(3-dimethylaminophenyl)-2,3,4,5-tetrahydro-1H-(1)benzazepin-1-yl]ethanoic acid amide;

N-tert-butyl-2-[2-oxo-3-(3-tolylureido)-5-(3-sulfonamidophenyl)-2,3,4,5-tetrahydro-1H-(1)benzazepin-1-yl]ethanoic acid amide;

N-tert-butyl-2-[2-oxo-3-(3-tolylureido)-5-(3-(acetylamino)phenyl)-2,3,4,5-tetrahydro-1H-(1)benzazepin-1-yl]ethanoic acid amide;

N-tert-butyl-2-[2-oxo-3-(3-tolylureido)-5-(3,4-difluorophenyl)-2,3,4,5-tetrahydro-1H-(1)benzazepin-1-yl]ethanoic acid amide;

N-tert-butyl-2-[2-oxo-3-(3-tolylureido)-5-(3,4-dimethylphenyl)-2,3,4,5-tetrahydro-1H-(1)benzazepin-1-yl]ethanoic acid amide;

N-tert-butyl-2-[2-oxo-3-(3-ethylphenylureido)-5-(4-chlorophenyl)-2,3,4,5-tetrahydro-1H-(1)benzazepin-1-yl]ethanoic acid amide;

N-(1,1-dimethylpropyl)-2-[2-oxo-3-(3-tolylureido)-5-(4-chlorophenyl)-2,3,4,5-tetrahydro-1H-(1)benzazepin-1-yl]ethanoic acid amide;

N-tert-butyl-2-[2-oxo-3-(3-dimethylaminophenylureido)-5-(4-chlorophenyl)-2,3,4,5-tetrahydro-1H-(1)benzazepin-1-yl]ethanoic acid amide;

N-tert-butyl-2-[2-oxo-3-(3-dimethylaminophenylureido)-5-(4-methylphenyl)-2,3,4,5-tetrahydro-1H-(1)benzazepin-1-yl]ethanoic acid amide;

N-(1,1-dimethylpropyl)-2-[2-oxo-3-(3-tolylureido)-5-(4-methylphenyl)-2,3,4,5-tetrahydro-1H-(1)benzazepin-1-yl]ethanoic acid amide;

N-tert-butyl-2-[2-oxo-3-(3-ethylphenylureido)-5-(4-chlorophenyl)-8-methyl-2,3,4,5-tetrahydro-1H-(1)benzazepin-1-yl]ethanoic acid amide;

N-(1,1-dimethylpropyl)-2-[2-oxo-3-(3-tolylureido)-5-(4-chlorophenyl)-8-methyl-2,3,4,5-tetrahydro-1H-(1)benzazepin-1-yl]ethanoic acid amide;

N-tert-butyl-2-[2-oxo-3-(3-dimethylaminophenylureido)-5-(4-chlorophenyl)-9-methyl-2,3,4,5-tetrahydro-1H-(1)benzazepin-1-yl]ethanoic acid amide;

N-tert-butyl-2-[2-oxo-3-(3-dimethylaminophenylureido)-5-(4-methylphenyl)-8-chloro-2,3,4,5-tetrahydro-1H-(1)benzazepin-1-yl]ethanoic acid amide;

N-(1,1-dimethylpropyl)-2-[2-oxo-3-(3-tolylureido)-5-(4-methylphenyl)-8-chloro-2,3,4,5-tetrahydro-1H-(1)benzazepin-1-yl]ethanoic acid amide;

N-(1,1-dimethylpropyl)-2-[2-oxo-3-(3-ethylphenylureido)-5-(4-methylphenyl)-8-chloro-2,3,4,5-tetrahydro-1H-(1)benzazepin-1-yl]ethanoic acid amide;

N-(1,1-dimethylpropyl)-2-[2-oxo-3-(3-dimethylaminophenylureido)-5-(4-methylphenyl)-8-chloro-2,3,4,5-tetrahydro-1H-(1)benzazepin-1-yl]ethanoic acid amide;

N-(1,1-dimethylpropyl)-2-[2-oxo-3-(3-dimethylaminophenylureido)-5-(4-chlorophenyl)-8-chloro-2,3,4,5-tetrahydro-1H-(1)benzazepin-1-yl]ethanoic acid amide;

N-(1,1-dimethylpropyl)-2-[2-oxo-3-(3-tolylureido)-5-(4-methylphenyl)-8-methyl-2,3,4,5-tetrahydro-1H-(1)benzazepin-1-yl]ethanoic acid amide;

N-(1,1-dimethylpropyl)-2-[2-oxo-3-(3-ethylphenylureido)-5-(4-chlorophenyl)-8-methyl-2,3,4,5-tetrahydro-1H-(1)benzazepin-1-yl]ethanoic acid amide;

N-(1,1-dimethylpropyl)-2-[2-oxo-3-(3-dimethylaminophenylureido)-5-(4-chlorophenyl)-8-methyl-2,3,4,5-tetrahydro-1H-(1)benzazepin-1-yl]ethanoic acid amide;

N,N-di(tert-butyl-2-[3-(3-(chlorophenyl)ureido)-2-oxo-5-phenyl-2,3,4,5-tetrahydro-1H-(1)benzazepin-1-yl]ethanoic acid amide;

N,N-di(tert-butyl)-2-[3-(3-tolyl)ureido)-2-oxo-5-phenyl-2,3,4,5-tetrahydro-1H-(1)benzazepin-1-yl]ethanoic acid amide;

N,N-di(tert-butyl)2-[3-(3-(methoxyphenyl)ureido)-2-oxo-5-phenyl-2,3,4,5-tetrahydro-1H-(1)benzazepin-1-yl]ethanoic acid amide;

3-((3-chlorophenyl)ureido)-7-(2,6-dimethylcyclohexyl)-(N-t-butoxycarbonylmethyl)-hexahydroazepin-2-one;

3-((3-tolyl)ureido)-7-(2,6-dimethylcyclohexyl)-(N-t-butoxycarbonylmethyl)-hexahydroazepin-2-one;

3-((3-methoxyphenyl)-7-(2,6-dimethylcyclohexyl)-(N-t-butoxycarbonylmethyl)-hexahydroazepin-2-one;

3-((3-methoxyphenyl)ureido)-5-phenyl-7-cyclohexyl-(N-1-adamantylcarbonylmethyl)-hexahydroazepin-2-one;

3-((3-methoxyphenyl)ureido)-5-phenyl-7-cyclohexyl-(N-2-adamantylcarbonylmethyl)-hexahydroazepin-2-one;

3-((3-tolyl)ureido)-5-phenyl-7-cyclohexyl-(N-1-adamantyloxycarbonylmethyl)-hexahydroazpin-2-one;

3-((3-tolyl)ureido)-5-phenyl-7-cyclohexyl-(N-2-adamantyloxycarbonylmethyl)-hexahydroazepin-2-one;

3-((3-chlorophenyl)ureido)-5-phenyl-7-cyclohexyl-(N-1-adamantyloxycarbonylmethyl)-hexahydroazepin-2-one; and 3-((3-chlorophenyl)ureido)-5-phenyl-7-cyclohexyl-(N-2-adamantyloxycarbonylmethyl)-hexahydroazepin-2-one.

This invention also relates to compounds of the formula

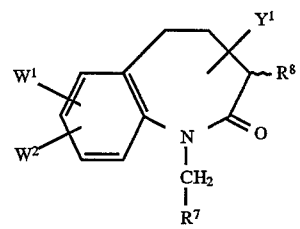

XVI wherein $R^7$ is hydrogen or one of the radicals set forth in the definition of $R^1$ above, $R^8$ is bromine, amino or azido and $Y^1$, $W^1$ and $W^2$ are defined as above. These compounds are useful as intermediates in the synthesis of compounds of the formula II.

The present invention also relates to a pharmaceutical composition for treating or preventing a condition selected from the group consisting of pain, gastrointestinal disorders such as ulcer and colitis, and central nervous system disorders such as anxiety and panic disorder in a mammal, including a human, comprising an amount of a compound of the formula I or II, or a pharmaceutically acceptable salt thereof, effective in treating or preventing such condition, and a pharmaceutically acceptable carrier.

The present invention also relates to a method of treating or preventing a condition selected from the group consisting of pain, gastrointestinal disorders such as ulcer and colitis, and central nervous system disorders such as anxiety and panic disorder in a mammal, including a human, comprising administering to said mammal an amount of a compound of the formula I or II, or a pharmaceutically acceptable salt thereof, effective in treating or preventing such condition.

The present invention also relates to a pharmaceutical composition for antagonizing the effects of cholecystokinin in a mammal, including a human, comprising a cholecystokinin antagonizing amount of a compound of the formula I or II, or a pharmaceutically acceptable salt thereof, and a pharmaceutically acceptable carrier.

The present invention also relates to a method of antagonizing the effects of cholecystokinin in a mammal, including a human, comprising administering to said mammal a cholecystokinin antagonizing amount of a compound of the formula I or II, or a pharmaceutically acceptable salt thereof.

The present invention also relates to a pharmaceutical composition for treating or preventing a cholecystokinin mediated disorder in a mammal, including a human, comprising a cholecystokinin antagonizing amount of a compound of the formula I or II, or a pharmaceutically acceptable salt thereof, and a pharmaceutically acceptable carrier.

The present invention also relates to a method of treating or preventing a cholecystokinin medicated disorder in a mammal, including a human, comprising administering to said mammal a cholecystokinin antagonizing amount of a compound of the formula I or II, or a pharmaceutically acceptable salt thereof.

The present invention also relates to a pharmaceutical composition for treating or preventing a condition selected from the group consisting of pain, gastrointestinal disorders such as ulcer and colitis, and central nervous system disorders such as anxiety and panic disorder in a mammal, including a human, comprising an amount of a compound of the formula I or II, or a pharmaceutically acceptable salt thereof, effective in antagonizing the effect of cholecystokinin at its receptor site, and a pharmaceutically acceptable carrier.

The present invention also relates to a method of treating or preventing a condition selected from the group consisting of pain, gastrointestinal disorders such as ulcer and colitis, and central nervous system disorders such as anxiety and panic disorder in a mammal, including a human, comprising administering to said mammal an amount of a compound of the formula I or II, or a pharmaceutically acceptable salt thereof, effective in antagonizing the effect of cholecystokinin at its receptor site.

The compounds of the formulae I and II have chiral centers and therefore exist in different enantiomeric and diastereomic forms. This invention relates to all optical isomers and all stereoisomers of compounds of the formulae I and II, and mixtures thereof.

Formula I and formula II above include compounds identical to those depicted but for the fact that one or more hydrogen or carbon atoms are replaced by isotopes thereof. Such compounds are useful as research and diagnostic tools in metabolism pharmacokinetic studies and in binding assays.

DETAILED DESCRIPTION OF THE INVENTION

The compounds of the formulae I and II may be prepared as described in the following reaction schemes and discussion. Unless otherwise indicated, $R^1, R^2, R^3, R^4, R^5, R^6, Y^1, Y^2, Z^1, Z^2, W^1$ and $W^2$ in the reaction schemes and discussion that follow are defined as above.

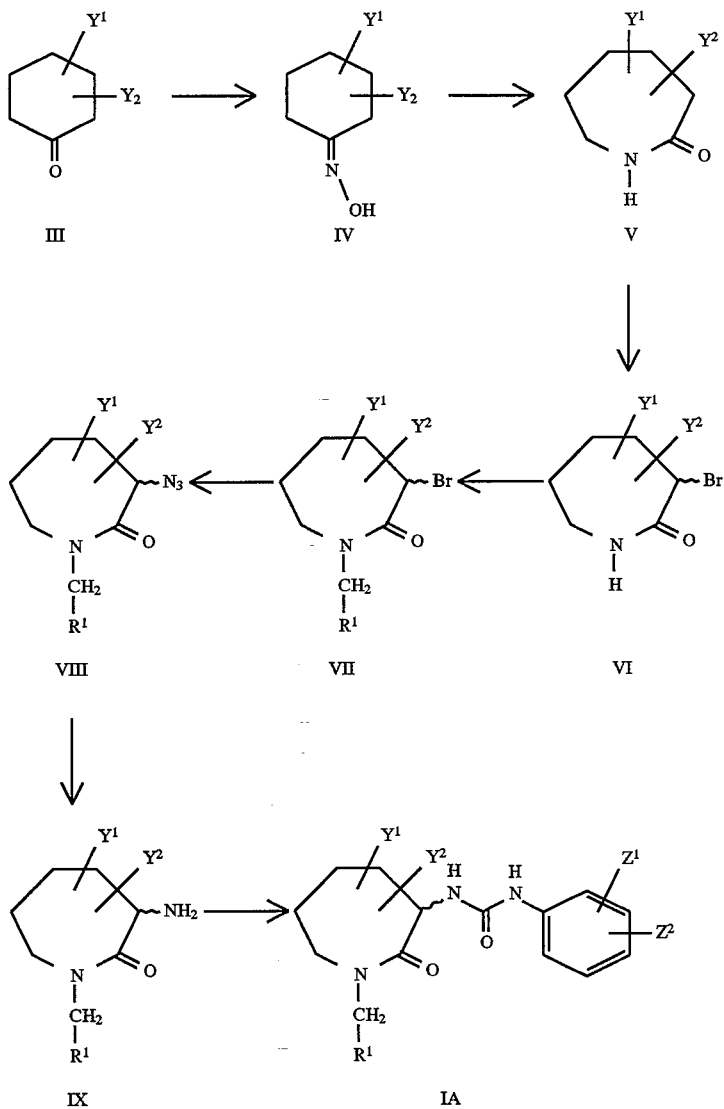

Scheme 1

($R^1 = CO_2R^2, C_6H_5, CONR^4R^5$ or $SO_2NR^3R^6$)

Scheme 2
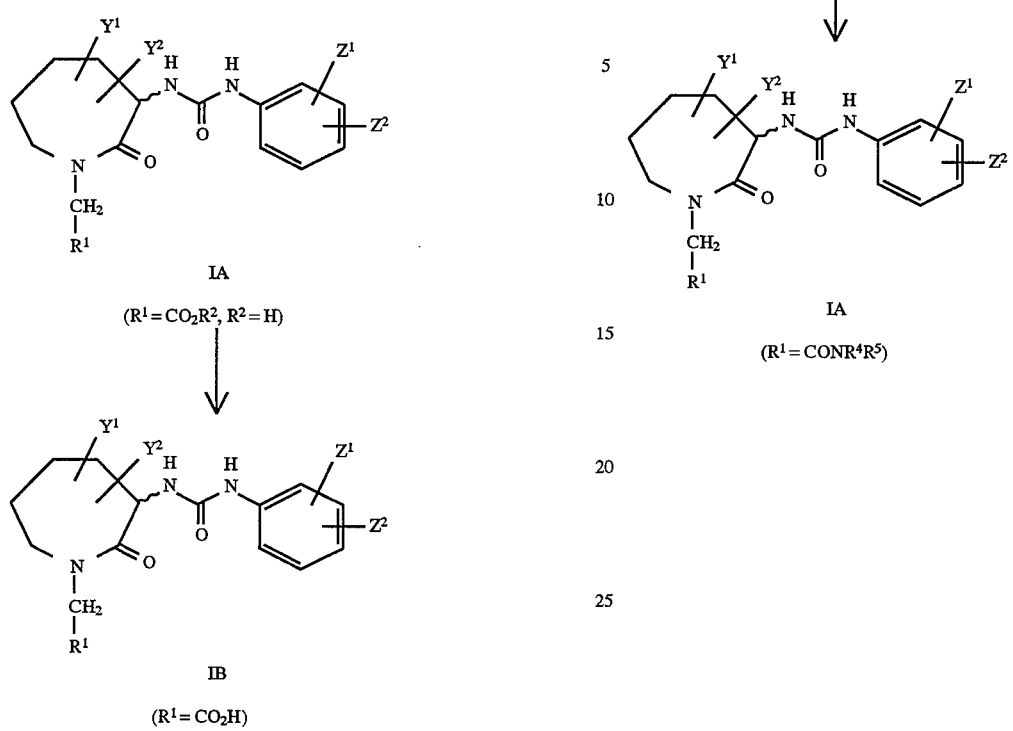
Scheme 3
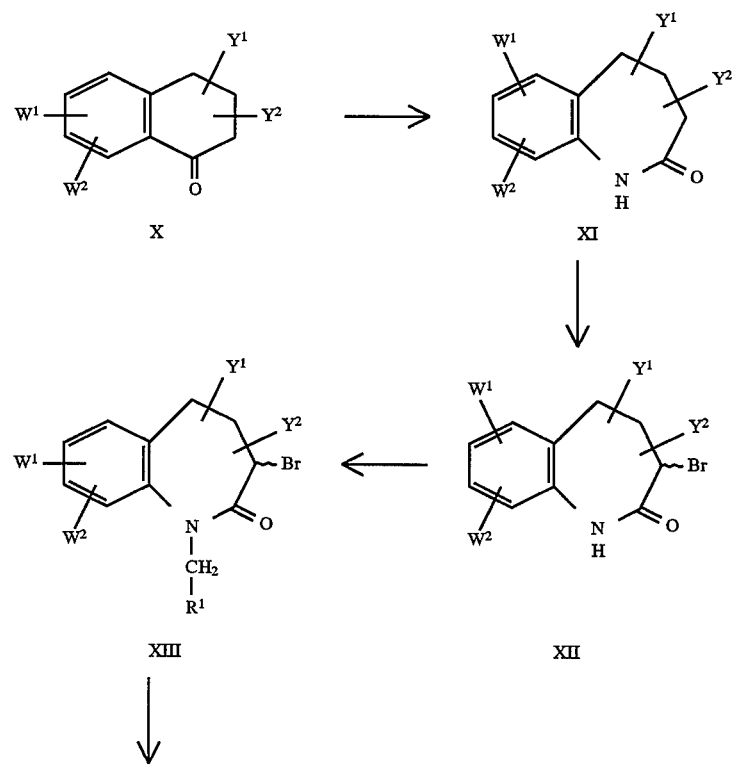

-continued
Scheme 3

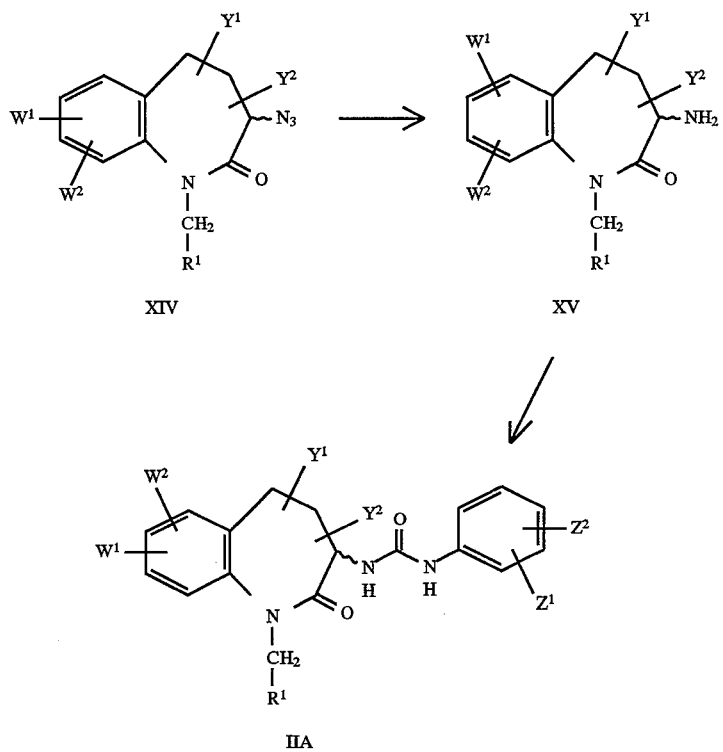

($R^1 = CO_2R^2$, $C_6H_5$, $CONR^4R^5$ or $SO_2NR^3R^6$)

The preparation of compounds of the formula I wherein $R^1$ is $CO_2R^2$, $C_6H_5$, $CONR^4R^5$ or $SO_2NR^3R^6$ (hereinafter referred to as compounds of the formula IA) is illustrated in scheme 1.

Referring to scheme 1, a compound of the formula III is reacted with hydroxylamine hydrochloride in methanol in the presence of sodium bicarbonate or triethylamine, to form a compound of the formula IV. This reaction is generally carried out at a temperature from about room temperature to about the reflux temperature of the reaction mixture. The compound of formula IV so formed is then converted to a compound of the formula V by reacting it with tosyl chloride in pyridine at about 0° C. for about 24 hours.

Alternatively, compounds of the formula III may be converted directly into the corresponding compounds having formula V in a one step procedure. According to this procedure, a compound of the formula III is reacted with $NH_2OSO_3H$ (hydroxylamine-O-sulfonic acid) in formic acid at about the reflux temperature of the reaction mixture. This one step procedure is preferred over the two step procedure described above for all compounds of the formula IV except those wherein $Y^1$ is phenyl and adjacent to the oxo group.

Bromination of the compound of formula V yields the corresponding compound having formula VI. The bromination is typically carried out by first adding a compound of the formula V to a mixture of phosphorus pentachloride and pyridine in methylene chloride at about 0° C. Then, phenyltrimethylammonium bromide tribromide is added to the reaction mixture, also at a temperature of about 0° C. Alternatively, the second step, which involves the addition of the brominating agent, may be replaced by a procedure in which bromine is added at a temperature of about 0° C. and allowed to react for a period of about 0.5 hours to about 5 hours, preferably about 2 hours, resulting in dibromination of the saturated nitrogen containing seven membered ring. One of the bromine atoms is then selectively removed by treatment with hydrogen gas in the presence of palladium which has been poisoned with quinoline.

The brominated compound of formula VI is then alkylated at the ring nitrogen by reaction with a compound of the formula $XCH_2R^1$, wherein X is bromine when $R^1$ is phenyl and X is iodine for all other $R^1$, in tetrahydrofuran (THF) in the presence of sodium hydride. This reaction, which yields the corresponding compound of formula VII, is usually conducted at a temperature from about room temperature to about 150° C. It is preferably conducted at the reflux temperature of the reaction mixture.

The compound of formula VII formed in the above step is then reacted with an alkali metal azide to produce a compound of the formula VIII. The preferred reactant is sodium azide. Generally, this reaction is carried out in a reaction inert solvent such as dimethylformamide (DMF) or dimethylsulfoxide (DMSO), preferably DMF, at a temperature from about 60° C. to about 100° C., preferably about 80° C.

Reduction of the azide of formula VIII yields the corresponding amine of formula IX. The reduction is typically accomplished using hydrogen gas at a pressure of from about 1 to about 3 atmospheres in the presence of palladium on carbon (Pd/C). Suitable reaction inert solvents include halogenated hydrocarbons and ($C_1$–$C_6$) alkanols. Ethanol is the preferred solvent. The reaction temperature may range from about 15° C. to about 70° C., with about room temperature being preferred.

Alternatively, the reduction may be accomplished using a trialkyl or triaryl phosphine. Examples of appropriate reactants are triphenylphosphine and tributylphosphine. This reaction is generally conducted in a reaction inert solvent such as THF or another ethereal water miscible solvent in the presence of water, at a temperature from about room temperature to about 100° C. Preferably, it is conducted in THF at about room temperature.

The compound of formula IX so formed is then converted into the corresponding compound having formula IA by reacting it with an isocyanate of the formula $C_6H_4Z^1Z^2NCO$. Appropriate reaction inert solvents for this reaction include hydrocarbons such as hexane, benzene and toluene, halogenated hydrocarbons such as methylene chloride and 1,2-dichloroethane, ethereal solvents such as ethyl ether, THF and glyme, and pyridine. The preferred solvent is 1,2-dichloroethane or methylene chloride. Tertiary organic amines may be useful as catalysts. The reaction temperature may range from about 0° C. to about 150° C. The reflux temperature is preferred.

The isocyanate of the formula $C_6H_4Z^1Z^2NCO$ used in the foregoing reaction can be formed by procedures well known to those skilled in the art. One such method involves mixing a benzoic acid derivative with diphenylphosphorylazide, or an analagous reagent, in the presence of an organic base such as a trialkylamine, preferably triethylamine or diisopropylethylamine. This reaction is usually conducted in an ethereal, hydrocarbon or chlorinated hydrocarbon solvent, preferably tetrahydrofuran or benzene, at a temperature from about room temperature to about 100° C., preferably at the reflux temperature of the solvent, for a period from about 20 minutes to about 24 hours, preferably about 1 hour.

Scheme 2 illustrates the synthesis of compounds of the formula I wherein $R^1$ is $CO_2H$ (hereinafter referred to as compounds of the formula IB) from compounds of the formula IA wherein $R^1$ is $CO_2R^2$. It also illustrates a method of preparing compounds of the formula IA wherein R is an amide (i.e., $R^1$ is $CONR^4R^5$) from the corresponding acids of formula IB.

Referring to scheme 2, hydrolysis of a compound of the formula IA wherein $R^1$ is $CO_2R^2$ yields the corresponding acid of formula IB. The hydrolysis is typically carried out using trifluoroacetic acid in a reaction inert solvent as hexane, an ethereal solvent (e.g., ethyl ether or THF) or a halogenated hydrocarbon solvent (e.g., methylene chloride or 1,2-dichloroethane), at a temperature from about −78° C. to about 50° C. It is preferably carried out using trifluoroacetic acid in a halogenated hydrocarbon cosolvent at about 0° C.

The acid of formula IB may be converted into the corresponding amide of formula IA, wherein $R^1$ is $CONR^4R^5$, by reacting the acid with an amine of the formula $NHR^4R^5$ in the presence of a dehydrating agent. The dehydrating agent is preferably a carbodiimide. Other dehydrating agents that may be used are 1,1'-carbonyldiimidazole and isobutylchloroformate/N-methylmorpholine. This reaction is generally conducted in a reaction inert solvent selected from hydrocarbons such as benzene, toluene and hexane, halogenated hydrocarbons such as methylene chloride and 1,2-dichloroethane, ethereal solvents such as ethyl ether, THF and glyme, and pyridine, preferably THF, at a temperature from about 0° C. to about 120° C., preferably at about room temperature.

Scheme 3 illustrates the preparation of compounds of the formula II wherein $R^1$ is $CO_2R^2$, $C_6H_5$, $CONR^4R^5$ or $SO_2NR^3R^6$ (hereinafter referred to as compounds of the formula IIA).

Referring to scheme 3, a compound of the formula X is converted into the corresponding compound of formula XII by the following two step procedure. First, the compound of formula X is converted into an oxime by the method described above and illustrated in scheme 1 for forming compounds of the formula IV from compounds of the formula III. Then, rearrangement of the oxime to form the lactam having formula XI is accomplished by reacting the oxime with polyphosphoric acid. This reaction may be carried out at temperatures ranging from about room temperature to about 200° C. Preferably, the reaction mixture is heated to about 160° C.

The resulting compound of formula XI is then brominated to form a compound of the formula XII by first reacting it with phosphorous pentachloride and pyridine, and then adding bromine. The reaction with phosphorus pentachloride and pyridine is conducted as described above for the first step in the bromination of compounds of the formula V. The reaction with bromine, which results in monobromination, is carried out at a temperature from about −78° C. about 0° C., preferably at about −40° C.

Alkylation of the compound of formula XII yields the corresponding compound of formula XIII. The alkylation is carried out by reacting the compound of formula XII with a compound of the formula $XCH_2R^1$, wherein X is bromine when $R^1$ is phenyl and X is iodine for all other $R^1$, in THF/DMSO in the presence of lithium dialkylamide. It is preferable to add the DMSO cosolvent after adding the lithium dialkylamide. The reaction temperature may range from about −78° C. to about 0° C. during addition of the base, and is preferably about −78° C. The reaction is slowly warmed to a temperature from about −20° C. to about 50° C. when the DMSO is added. Preferably, the reaction is warmed to about room temperature during addition of DMSO.

The conversion of compounds of the formula XIII formed by the foregoing procedure into the corresponding compounds of the formula IIA by the reaction sequence XIII→XIV→XV→IIA depicted in scheme 3 in carried out by the method described above for the analogous reaction steps VII→VIII→IX→IA depicted in scheme 1.

Compounds of the formula II wherein $R^1$ is $CO_2H$ may be prepared, and compounds of the formula II wherein $R^1$ is $CONR^4R^5$ may be prepared, alternatively, by the procedure depicted in scheme 2 and described above forming the analogous compounds of formula I.

The starting materials used in the procedures of schemes 1 and 3 are either commercially available, known in the art or readily obtainable form known compounds by methods that will be apparent to those skilled in the art.

The preparation of other compounds of the formulae I and II not specifically described in the foregoing experimental section can be accomplished using combinations of the reactions described above that will be apparent to those skilled in the art.

In each of the reactions discussed or illustrated in schemes 1 to 3 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The compounds of the formulae I and II (the active compounds of this invention) which are basic in nature are capable of forming a wide variety of different salts with various inorganic and organic acids. Although such salts must be pharmaceutically acceptable for administration to animals, it is often desirable in practice to initially isolate a compound of the formula I or II from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The active compounds of this invention and their pharmaceutically acceptable salts are useful as selective CCK-B receptor antagonists, i.e., they possess the ability to antagonize the effects of CCK at its B receptor site in mammals, and therefore they are able to function as therapeutic agents in the treatment of the aforementioned disorders and diseases in an afflicted mammal.

The active compounds of this invention and their pharmaceutically acceptable salts can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The active compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically when treating inflammatory conditions of the skin and this may preferably be done by way of creams, jellies, gels, pastes, ointments and the like, in accordance with standard pharmaceutical practice.

The activity of the compounds of the present invention as CCK-B antagonists may be determined by an assay that measures their ability to inhibit the binding of 125-I-BH-CCK-8 to the CCK-B receptor in a guinea pig cortical membrane preparation. This procedure is carried out as follows. The cortex is dissected from one male Hartley Guinea pig and homogenized (15 strokes) with a teflon homogenizer in 20 volumes (w./v.) of the assay buffer, which consists of 50 mM Tris (i.e., trimethamine, which is 2-amino-2-hydroxymethyl-1,3-propanediol) hydrochloric acid having pH 7.4 and 5 mM of manganese chloride at 4° C. The homogenate is centrifuged at 4° C. for 30 minutes at 100,000×G. The pellet is resuspended in the same buffer and spun as described above. The final pellet is diluted to a concentration of 20 mg/ml with the assay buffer for use in the binding assay. The tissue is kept on ice at all times.

An incubation mixture is prepared, which consists of 50 uL of the tissue preparation, prepared as described above, 100 uL 125-I-BH-CCK-8 (to give a concentration of 50 pM in the final assay), 20 uL of a blank or the compound being tested, and 30 uL of Tris with 4% DMSO. All drugs and dilutions are made using 4% DMSO in the assay buffer yielding a final assay DMSO concentration of 1%.

The reaction is initiated with the addition of tissue to a 96-well plate containing 125-I-BH-CCK-8 and the appropriate blank or compound being tested. Non-specific binding is estimated using 1 uM sulphated CCK-8. The reaction is terminated by spinning the plates in a H1000B rotor fitted on a Sorvall RT6000 refrigerated centrifuge at 4° C. The supernatant is discarded, and the pellets washed with 200 uL of assay buffer, and the plate is spun as above. The supernatant is decanted again, and the pellet is harvested onto Betaplate filters (which have been soaked in 0.2% polyethyleneimine for a minimum of 2 hours) using a Skatron cell harvester at setting 222 using Tris HCl pH 7.4 as the wash buffer. The filtermats are counted on a Betaplate counter for 45 seconds per sample.

Data are expressed as $IC_{50}$ values (the concentration which inhibits 50% of the specific binding of 125-I-BH-CCK-8). The data is analyzed using non-linear regression analysis.

The present invention is illustrated by the following examples. It will be understood, however, that the invention is not limited to the specific details of these examples.

EXAMPLE 1

N-tert-butyl-2-[3-(3-(3-tolyl)ureido)-2-oxo-5-phenyl-2,3,4,5-tetrahydro-1H-(1)benzazepin-1-yl] ethanoic acid amide A. 3-Bromo-5-phenyl-2,3,4,5-tetrahydro-1H-(1) benzazepin-2-one To a 125 ml round-bottomed flask containing $PCl_5$ (1.041 g, 5 mmoles) dissolved in 50 ml methylene chloride under nitrogen in an ice/acetone bath was added 5-phenyl-2,3,4,5-tetrahydro-1H-(1)benzazepin-2-one (1.187 g, 5 mmoles). A slight temperature rise was noted, and then pyridine (0.42 ml, 5.25 mmoles) in 5 ml methylene chloride was added rapidly dropwise. The mixture was stirred for 15 minutes. and then cooled to −45° C. Bromine (0.258 ml, 5 mmoles) in 7 ml methylene chloride was then added dropwise over 30 minutes. with rapid stirring. The bath was removed after 15 minutes. and the mixture was allowed to come to room temperature. Thin layer chromatography (TLC) (silica gel, 23:2, methylene chloride:ethyl acetate) showed no starting material, only a non-polar intermediate (iminochloride). The remainder of the reaction was diluted with an equal volume of tetrahydrofuran and 200 ml water added. This mixture was stirred for 40 minutes, then separated. The aqueous layer was re-extracted with methylene chloride and the combined organic fractions washed with water, dried with brine and sodium sulfate, filtered, and evaporated yielding 1.56 g (98.7%) of crude product.

The diastereomeric bromides ($R_f$=0.57, and 0.48) may be separated by chromatography or crystallized from ether and hexane; however, the mixture was used directly in the next step (B).

The solid obtained by crystallization was predominately the more polar isomer while the mother liquor contained more of the less polar isomer as well as traces of the iminochloride and starting material. Recrystallization of the more polar diastereomer from chloroform gave large crystals, mp 191°–192° C.:

$^1$H-NMR (δ, $CDCl_3$): 2.92 (m, 1H), 3.14 (m, 1H), 4.49 (m, 1H), 4.63 (m, 1H), 6.77 (d, 1H), 7.09 (m, 3H), 7.32 (m, 6H), 7.85 (bs, 1H).

MS (%): 315/317 (parent for $Br^{79}/Br^{81}$, 20/18) 236 (78), 208 (100), 194 (36), 180 (73), 130 (47), 115 (39), 91 (79).

B. t-Butyl 2-[3-bromo-2-oxo-5-phenyl-2,3,4,5-tetrahydro-1H-(1)benzazepin-1-yl]ethanoate To a 125 ml three-neck round bottomed flask equipped with septum and $N_2$ inlet were added 3-bromo-5-phenyl-2,3,4,5-tetrahydro-1H-(1)benzazepin-2-one (3.216 g, 10.17 mmoles) and 50 ml dry tetrahydrofuran (THF) under nitrogen. The reaction was cooled in a dry ice bath, and lithium bis-trimethylsilyl amide (11.2 ml of 1M in THF) was added slowly. The mixture was stirred for 5 minutes. T-butyl iodoacetate (2.708 g, 11.19 mmoles) was then added. The bath was removed and 25 ml of dimethylsulfoxide (DMSO) was added at −20° C. After one hour at room temperature, an acidified aliquot showed only a trace of starting material by TLC (24:1, $CH_2Cl_2$:EtOAc). The reaction mixture was poured into ice water and ethyl acetate containing 25 ml of N HCl, stirred for 5 minutes. and separated. The ethyl acetate extraction was repeated and the combined extracts washed three times with water, dried with brine and sodium sulfate, and filtered and evaporated, yielding 4.9 g (>100%, still containing traces of solvent) crude product.

Similarly, the lactam was alkylated with N-tert-butyl iodoacetamide to yield N-t-Butyl-2-[3-bromo-2-oxo-5-phenyl-2,3,4,5,-tetrahydro-1H-(1)benzazepin-1-yl]-ethanoic acid amide.

C. N-tert-butyl-2-[3-azido-2-oxo-5-phenyl-2,3,4,5-tetrahydro-1H-(1)benzazepin-1-yl]ethanoic acid amide To a 250 ml round-bottomed flask equipped with $N_2$ inlet were added N-tert-butyl-2-[3-bromo-2-oxo-5-phenyl-2,3,4,5-tetrahydro-1H-(1)benzazepin-1-yl]ethanoic acid amide, (8.317 g, 19.37 mmoles), 90 ml dimethylformamide (DMF), and sodium azide (5.25 g, 80 mmoles, under nitrogen), and the mixture was heated at 75° C. for 20 hours with stirring. The reaction mixture was then cooled and distributed between water and ethyl acetate, separated, and the aqueous phase was again extracted. The combined extracts were washed with water three times, with bicarbonate solution once, and then dried with brine and sodium sulfate and filtered and evaporated, leaving a gummy residue, 8.58 g (100%), containing some solvent.

$^1$H-NMR (δ, $CDCl_3$): 1.48 (s, 9H), 2.88 (m, 2H), 4.52 (AB quartet, $J_{AB}$=17, Δγ=138, 2H), 4.57 (m, 1H), 5.06 (m, 1H), 6.73 (d, 1H), 7.26 (m, 8H).

D. N-tert-butyl-2-[3-amino-2-oxo-5-phenyl-2,3,4,5-tetrahydro-1H-(1)benzazepin-1-yl]ethanoic acid amide The crude product from the previous displacement reaction, N-tert-butyl-2-[3-azido-2-oxo-5-phenyl-2,3,4,5-tetrahydro-1H-(1)benzazepin-1-yl]ethanoic acid amide, (8.58 g, 19.37 mmoles), was dissolved in 75 ml methanol under nitrogen. The catalyst, 6 g of 5% Pd/C, 50% w/w, was added and the mixture was hydrogenated at 55 psi $H_2$ for 5 hours. The mixture was filtered through Celite®and the catalyst washed three times with methanol and the filtrate evaporated. TLC (24:1, methylene chloride: methanol, silica gel), showed less polar material and the product at $R_f$=0.25. The crude product taken up in ethyl acetate and extracted with acid. The acidic extract was back washed with ethyl acetate and then the aqueous fraction was taken with fresh ethyl acetate and the pH adjusted to 10.0. The organic fraction was then dried with brine and sodium sulfate, filtered and concentrated, yielding 1.832 g (25.8%) of the crystalline amine (mp 189°–192° C., one diastereomer). The mother liquor yielded 1.545 g (21.8%) of a foam upon stripping the solvent, which contained nearly a 1:1 mixture of the diastereomers.

$^1$H-NMR (δ, $CDCl_3$): 1.30 (s, 9H), 2.2 (bs, 2H), 3.06 (AB quartet, $J_{AB}$=15, Δγ=276, 2H), 2.67 (m, 1H), 2.84 (m, 1H), 3.57 (m, 1H), 4.18 (m, 1H), 6.01 (bs, 1H), 7.2 (m, 9H).

E. N-tert-butyl-2-[3-(3-(3-tolyl)ureido)-2-oxo-5-phenyl-2,3,4,5-tetrahydro-1H-(1)benzazepin-1-yl]ethanoic acid amide To a 25 ml round-bottomed flask equipped with $N_2$ inlet were added N-tert-butyl-2-[3-amino-2-oxo-5-phenyl-2,3,4,5-tetrahydro-1H-(1)benzazepin-1-yl]ethanoic acid amide (0.50 g, 1.368 mmoles) and 10 ml methylene chloride under nitrogen, and the reaction cooled in an ice bath. A solution of m-tolyl isocyanate (0.194 ml, 1.5 mmol) in 5 ml methylene chloride was then added dropwise. A solid formed immediately. Stirring was continued for 15 minutes and then the ice bath removed, allowing the reaction to come to room temperature for several hours. The solid was filtered and washed with methylene chloride/hexane (1:1), yielding 600 mg (87.9%) of product, mp 263°–266° C.

NMR (δ, DMSO-$d_6$): 1.23 (s, 9H), 2.21 (s, 3H), 2.54 (m, 1H), 2.9 (m, 1H), 3.34 (AB quartet, $J_{AB}$=16, Δγ=255, 2H), 3.4 (HOD peak), 4.34 (m, 2H), 6.8 (m, 2H), 7.3 (m, 11H), 8.78 (s, 1H).

The title compounds of Examples 2 through 10 were prepared using a procedure analogous to that of Example 1.

EXAMPLE 2 tert-butyl-2-[3-(3-(4-chlorophenyl)ureido)-2-oxo-5-phenyl-2,3,4,5-tetrahydro-1H-(1)benzazepin-1-yl]ethanoate Prepared in 30% yield after chromatography and crystallization, M.P. 148°–150° C.

$^1$H-NMR ($\delta$, CDCl$_3$): 1.37 (s, 9H), 2.8–3.1 (m, 2H), 3.30 (AB quartet, J$_{AB}$=17, $\Delta v$=188, 2H), 4.27 (m, 1H), 4.76 (m, 1H), 6.8 (broad s, 1H), 7.0–7.5 (m, 14H).

MS (%): 520 (18, parent), 366 (35), 337 (43), 267 (70), 206 (85), 153 (76), 127 (100), 91 (53).

HRMS calc'd for C$_{29}$H$_{31}$N$_3$O$_4$Cl: 520.2003. Found: 520.1983.

EXAMPLE 3

N-tert-butyl-2-[3-(3-(3-chlorophenyl)ureido)-2-oxo-5-phenyl-2,3,4,5-tetrahydro-1H-(1)benzazepin-1-yl]ethanoic acid amide Prepared in 90% yield, mp 264°–266° C.

$^1$H-NMR ($\delta$, DMSO-d$_6$): 1.21 (s, 9H), 2.56 (m, 1H), 2.9 (m, 1H), 3.35 (AB quartet, J$_{AB}$=17, $\Delta v$=255, 2H), 4.37 (m, 2H), 6.7–7.6 (m, 14H), 9.08 (s, 1H).

MS (%): 518 (1, parent), 322 (40), 194 (60), 91 (70), 58 (100).

HRMS calc'd for C$_{29}$H$_{31}$N$_4$O$_3$Cl: 518.2097. Found: 518.2100.

EXAMPLE 4

N-tert-butyl-2-[3-(3-(2-tolyl)ureido)-2-oxo-5-phenyl-2,3,4,5-tetrahydro-1H-(1)benzazepin-1-yl]ethanoic acid amide Prepared in 85% yield, mp 231°–233° C.

$^1$H-NMR ($\delta$, CDCl$_3$): 1.28 (s, 9H), 2.24 (s, 3H), 2.65 (m, 1H), 3.09 (AB quartet J$_{AB}$=17, $\Delta v$=291, 2H), 3.11 (m, 1H), 4.22 (m, 1H), 4.62 (m, 1H), 6.01 (broad s, 1H), 6.41 (broad s, 1H), 6.9–7.5 (m, 13H).

MS (%): 498 (0.5, parent), 322 (5), 249 (8), 133 (80), 105 (100), 78 (80).

HRMS calc'd for C$_{30}$H$_{34}$N$_4$O$_3$: 498.2630. Found: 498.25475.

EXAMPLE 5

N-tert-butyl-2-[3-(3-(3-methoxyphenyl)ureido)-2-oxo-5-phenyl-2,3,4,5-tetrahydro-1H-(1)benzazepin-1-yl]ethanoic acid amide Prepared in 81% yield, mp 254°–257° C.

$^1$H-NMR ($\delta$, DMSO-d$_6$): 1.21 (s, 9H), 2.56 (m, 1H), 2.9 (m, 1H), 3.33 (AB quartet, J$_{AB}$=16, $\Delta v$=259, 2H), 4.35 (m, 2H), 6.4–7.6 (m, 14H), 8.865 (broad s, 1H).

MS (%): 514 (0.1, parent), 322 (6), 149 (100), 106 (40).

HRMS calc'd for C$_{30}$H$_{34}$N$_4$O$_4$: 514.2553. Found: 514.26134.

EXAMPLE 6

N-tert-butyl-2-[3-(3-(4-chlorophenyl)ureido)-2-oxo-5-phenyl-2,3,4,5-tetrahydro-1H-(1)benzazepin-1-yl]ethanoic acid amide Prepared in 88% yield, mp 247°–249° C.

$^1$H-NMR ($\delta$, CDCl$_3$): 1.31 (s, 9H), 2.92 (m, 1H), 3.10 (m, 1H), 3.22 (AB quartet, J$_{AB}$=16, $\Delta v$=260, 2H), 4.29 (m, 1H), 4.60 (m, 1H), 5.74 (broad s, 1H), 6.43 (broad s, 1H), 7.0–7.5 (m, 13H).

MS (%): 518 (1, parent), 322 (40), 261 (70), 153 (100).

HRMS calc'd for C$_{29}$H$_{31}$N$_4$O$_3$Cl: 518.2070. Found: 518.21007.

EXAMPLE 7

N-tert-butyl-2-[3-(3-(4-tolyl)ureido)-2-oxo-5-phenyl-2,3,4,5-tetrahydro-1H-(1)benzazepin-1-yl]ethanoic acid amide Prepared in 95% yield, mp 235°–238° C.

$^1$H-NMR ($\delta$, CDCl$_3$): 1.29 (s, 9H), 2.27 (s, 3H), 2.72 (m, 1H), 3.12 (m, 1H), 3.25 (AB quartet, J$_{AB}$=16, $\Delta v$=283, 2H), 4.24 (m, 1H), 4.60 (m, 1H), 5.88 (broad s, 1H), 6.8–7.4 (m, 14H).

MS (%): 498 (1, parent), 322 (30), 249 (15), 221 (20), (20), 133 (100).

HRMS calc'd for C$_{30}$H$_{34}$N$_4$O$_3$: 498.2646. Found: 498.26153.

EXAMPLE 8

N-tert-butyl-2-[3-(3-trifluoromethylphenyl)ureido-2-oxo-5-phenyl-2,3,4,5-tetrahydro-1H-(1)benzazepin-1-yl]ethanoic acid amide Prepared in 67% yield, mp 135°–139° C.

$^1$H-NMR ($\delta$, CDCl$_3$): 1.30 (s, 9H), 3.1 (m, 2H), 3.31 (AB quartet, J$_{AB}$=16, $\Delta v$=270, 2H), 4.32 (m, 1H), 4.62 (m, 1H), 5.77 (broad s, 1H), 6.6 (broad s, 1H), 7.0–7.9 (m, 13H).

MS (%): 552 (0.2, parent), 416 (1), 322 (5), 254 (20), 91 (100).

HRMS calc'd for C$_{30}$H$_{31}$N$_4$O$_3$F$_3$: 552.2341. Found: 552.2288.

EXAMPLE 9

N-tert-butyl-2-[3-(3-(3-thiomethylphenyl)ureido)-2-oxo-5-phenyl-2,3,4,5-tetrahydro-1H-(1)benzazepin-1-yl]ethanoic acid amide Prepared in 78% yield.

$^1$H-NMR ($\delta$, CDCl$_3$): 1.22 (s, 9H), 2.35 (s, 3H), 2.58 (m, 1H), 2.97 (m, 1H), 3.21 (AB quartet, J$_{AB}$=16, $\Delta v$=288, 2H), 4.18 (m, 1H), 4.40 (m, 1H), 6.6–7.4 (m, 13H), 7.75 (broad s, 1H), 8.67 (broad s, 1H).

MS (%): 530 (0.7, parent), 322 (18), 261 (21), 165 (100), 132 (32).

HRMS calc'd for C$_{30}$H$_{34}$N$_4$O$_3$S: 530.2352. Found: 530.2332.

EXAMPLE 10 tert-butyl-2-[3-(3-(3-tolyl)ureido)-2-oxo-5-phenyl-2,3,4,5-tetrahydro-1H-(1)benzazepin-1-yl]ethanoate Prepared in 76% yield, mp 195° C.

$^1$H-NMR ($\delta$, CDCl$_3$): 1.4 (s, 9H), 2.29 (s, 3H), 2.72 (m, 1H), 3.19 (m, 1H), 3.28 (AB quartet, J$_{AB}$=16, $\Delta v$=230, 2H), 4.22 (m, 1H), 4.7 (m, 1H), 6.37 (broad s, 1H), 6.78–7.5 (m, 14H).

MS (%): 500 (18, parent+1), 484 (4), 444 (20), 426 (4), 337 (42), 311 (100), 266 (20), 240 (30), 194 (34).

EXAMPLE 11

3-(3-Tolylureido)-7-phenyl-(N-2-adamantyl) carboxamidomethyl)-hexahydro-azepin-2-one A. 7-Phenyl-hexahydroazepin-2-one To a 250 ml round-bottomed flask equipped with $N_2$ inlet were added 7.33 g (38.8 mmol) 2-phenylcyclohexanone oxime (Chem. Ber., 55, 3664 (1922)) and 25 ml pyridine. The solution was cooled to 0° C., and 9.61 g (50.4 mmol) p-toluenesulfonyl chloride was added. The reaction was allowed to stir overnight as the ice melted, and then poured into water. Excess chloride was skimmed off the surface, and the reaction mixture was stirred at pH 4 for 3 hours. The precipitate was filtered, washed with water, and dried to a solid, 4.65 g (55%), mp 135°–137° C. (J. Am. Chem. Soc., 82, 4671 (1960) gives mp 139°–141° C.).

B. 3-Bromo-7-phenyl-hexahydroazepin-2-one

To a 250 ml round-bottomed flask equipped with $N_2$ inlet were added 5.12 g (24.6 mmol) phosphorus pentachloride and 45 ml methylene chloride. To the stirring mixture cooled to 0° C. was added dropwise over 20 minutes, a solution of 4.65 g (24.6 mmol) 7-phenyl-hexahydroazepin-2-one and 3.98 ml (49.2 mmol) pyridine in 40 ml methylene chloride. To the stirring mixture at 0° C. was then added 9.25 g (24.6 mmol) phenyltrimethylammonium bromide tribromide. The reaction was then allowed to warm to room temperature and stirred for 3 hours. It was then evaporated, taken up in tetrahydrofuran, quenched with water, evaporated, and partitioned between water and methylene chloride. The organic layer was washed with water and saturated aqueous sodium bisulfite, dried over sodium sulfate, and evaporated. The residue was chromatographed on silica gel with ethyl acetate/hexane as eluent to afford the product as an oil, 4.0 g (61%).

$^1$H-NMR ($\delta$, $CDCl_3$): 1.8–2.4 (m, 6H), 4.35 and 4.63 (multiplets, 1H), 4.7–4.9 (m, 1H), 5.73 and 5.81 (broad singlets, 1H, NH), 7.2–0.74 (m, 5H).

IR (cm.$^{-1}$,$CHCl_3$): 1670 (C=O).

MS (%): 267 (6,parent), 188 (39), 160 (70), 106 (100), 91 (43), 55 (59).

C. 3-Bromo-7-phenyl-(N-t-butoxycarbonylmethyl) hexahydroazepin-2-one

To a 100 ml three-necked round-bottomed flask equipped with $N_2$ inlet were added 0.30 g (6.07 mmol) sodium hydride, which was washed with hexane and suspended in 3 ml dry tetrahydrofuran. To the stirring mixture was added a solution of 1.55 g (5.78 mmol) 3-bromo-7-phenylhexahydroazepin-2-one and 1.42 g (6.07 mmol) t-butyl iodoacetate dropwise over 20 minutes. The reaction was stirred for 3 hours at room temperature, quenched with saturated aqueous ammonium chloride, and taken up in ethyl acetate. The organic layer was washed with water and brine, dried over sodium sulfate, and evaporated. The residue was chromatographed on silica gel using ethyl acetate/hexane as eluent to afford the product as an oil, 1.65 g (75%).

$^1$H-NMR ($\delta$, $CDCl_3$): 1.40 and 1.42 (singlets, 9H, two diastereomers), 1.8–2.4 (m, 6H), 3.6–3.9 (m, 2H), 4.56 and 4.95 (multiplets, 1H), 4.71 and 5.16 (multiplets, 1H), 7.2–7.4 (m, 5H).

D. 3-Azido-7-phenyl-(N-butoxycarbonylmethyl) hexahydroazepin-2-one

To a 100 ml round-bottomed flask equipped with $N_2$ inlet were added 1.65 g (4.32 mmol) 3-bromo-7-phenyl-(N-t-butoxycarbonylmethyl)-hexahydroazepin-2-one, 4 ml dimethylformamide, 0.34 g (5.18 mmol) sodium azide, and a drop of water. The mixture was heated at 80° C. for 36 hours, and then poured into water and extracted into ethyl acetate. The organic layer was washed with water and brine, dried over sodium sulfate and evaporated. The residue was chromatographed on silica gel with ethyl acetate/hexane as eluent to afford the product as an oil, 1.0 g (67%).

$^1$H-NMR ($\delta$, $CDCl_3$): 1.34 (s, 9H), 1.7–2.4 (m, 6H) (only one diastereomer could be accurately identified), 3.62 (AB quartet, $J_{AB}$=17, $\Delta\gamma$=193, 2H), 4.38 (m, 1H), 4.77 (m, 1H), 7.2–7.4 (m, 5H).

IR (cm.$^{-1}$, KBr): 2106 ($N_3$) and 1739 and 1661 (C=O).

E. 3-Amino-7-phenyl-(N-t-butoxycarbonylmethyl) hexahydroazepin-2-one

The azide from step D above (6. 1.0 g, 2.91 mmol) was treated under 45 lb/in$^2$ hydrogen in the presence of 200 mg 10% palladium-on-carbon in 30 ml ethanol for 4.6 hours. The reaction was filtered through Celite® and evaporated to leave an oil, which was used directly in the following step.

$^1$H-NMR ($\delta$, $CDCl_3$): 1.6–2.4 (m, 6H), 3.63 (only one diastereomer could be accurately identified) (AB quartet, $J_{AB}$=17, $\Delta\gamma$=156, 2H), 4.02 (m, 1H), 4.91 (m, 1H), 7.2–7.4 (m, 5H).

IR (cm.$^{-1}$, neat): 1741 and 1649 (C=O).

F. 3-(3-Tolylureido)-7-phenyl-(N-t-butoxycarbonylmethyl)-hexahydroazepin-2-one

To a 100 ml round-bottomed flask equipped with $N_2$ inlet were added 1.28 g (4.02 mmol) 3-amino-7-phenyl-(N-t-butoxycarbonylmethyl)-hexahydroazepin-2-one, 5 ml 1,2-dichlorethane and 0.57 ml (4.43 mmol) 3-tolylisocyanate. The reaction was stirred for 3 hours at room temperature and chromatographed on silica gel, using ethyl acetate/hexane as eluent, to afford the product as an oil. The oil was crystallized from isopropyl ether to give a solid, mp 194°–196° C.

$^1$H-NMR ($\delta$, $CDCl_3$): 1.25 (s, 9H), 1.6–2.3 (m, 6H), 2.17 and 2.20 (singlets, 3H, diastereomers), 3.56 (AB quartet, $J_{AB}$=17, $\Delta\gamma$=236, 2H), 5.01 (d, J=11, 1H), 5.08 (m, 1H), 6.71 (d, J=7, 1H), 6.8–7.3 (m, 9H), 7.87 (s, 1H).

IR (cm.$^{-1}$, KBr): 1743 and 1650 (C=O).

MS (%): 451 (14, parent), 159 (45), 117 (64), 107 (100), 91 (46), 57 (41), 56 (48).

Anal. calc'd for $C_{26}H_{33}N_3O_4$: C, 69.16; H, 7.57; N, 9.31. Found: C, 69.10; H, 7.75; N, 9.08.

G. 3-(3-Tolylureido)-7-phenyl-(N-carboxymethyl) hexahydroazepin-2-one

To a 100 ml round-bottomed flask equipped with $N_2$ inlet were added 1.5 g (3.32 mmol) 3-(3-tolylureido)-7-phenyl-(N-t-butoxycarbonylmethyl)-hexahydroazepin-2-one and 25 ml methylene chloride. The solution was cooled to 0° C. and 5 ml trifluoroacetic acid was added. The reaction was then stirred at 0° C. for 1.2 hours. The reaction was poured into water, extracted into methylene chloride, and the organic layer was washed with water and brine, dried over sodium sulfate, and evaporated. The residue was crystallized from isopropyl ether to afford a solid, mp 121°–130° C., 1.1 g (84%).

$^1$H-NMR ($\delta$, $CDCl_3$): 1.4–2.2 (m, 6H), 2.22 and 2.24 (singlets, 3H (one for each diastereomer)), 3.55 and 3.61 (AB quartet-1, $J_{AB}$=18, $\Delta\gamma$=138 and AB quartet-2, $J_{AB}$=18, $\Delta\gamma$=348, 2H), 3.4–3.8 (m, 1H), 4.0–4.1 (m, 1H), 6.6 and 6.78 (m, 2H), 7.07–7.4 (m, 9H).

IR (cm.$^{-1}$, KBr): 1740 and 1640 (C=O).

MS (%): 395 (9, parent), 159 (63), 133 (100), 98 (78).

HRMS calc'd for $C_{22}H_{25}N_3O_4$: 395.1769. Found: 395.1853.

H. 3-(3-Tolylureido)-7-phenyl-(N-(N-2-adamantyl) carboxamidomethyl)-hexahydroazepin-2-one To a 100 ml round-bottomed flask equipped with $N_2$ inlet were added 330 mg (0.835 mmol) 3-(3-tolylureido)-7-phenyl-(N-carboxymethyl)-hexahydroazepin-2-one, 5 ml 1,2-dichloroethane, 0.25 g (1.7 mmol) 2-aminoadamantane, and 0.24 g (1.25 mmol) ethyl(dimethylaminopropyl) carbodiimide. The reaction was stirred 3 days at room temperature and chromatographed on silica gel using methanol/methylene chloride as eluent to afford an oil which was crystallized from isopropyl ether to give a solid, 20 mg (4.5%), mp 145°–153° C.

$^1$H-NMR ($\delta$, CDCl$_3$): 1.4–2.2 (m, 22H), 2.20 and 2.23 (singlets, 3H, for each diastereomer), 3.6 (AB quartet, J$_{AB}$=14, $\Delta\gamma$=121 (for one set, other set obscured), 2H), 3.9 (m, 1H), 4.5–4.8 (m, 1H), 5.04 and 5.12 multiplets, 1H), 6.08 and 6.42 (d, J=8, 1H), 6.7 and 7.0–7.4 (m, 9H), 7.65 and 7.77 (m, 1H).

IR (cm.$^{-1}$, KBr): 1650 (C=O).

MS (%): 528 (6, parent), 193 (100), 171 (65).

HRMS calc'd for C$_{32}$H$_{40}$N$_4$O$_3$: 528.3100. Found: 528.3051.

Anal. calc'd for C$_{32}$H$_{40}$N$_4$O$_3$·0.5H$_2$O: C, 71.48; H, 7.69; N, 10.42. Found: C, 71.61; H, 7.34; N, 10.27.

The title compounds of Examples 12–21 were prepared using a procedure analogous to that of Example 11.

EXAMPLE 12

3-(3-Tolylureido)-7-benzyl-(N-t-butoxycarbonylmethyl)hexahydroazepin-2-one

Prepared in 79% yield, M.P. 75°–86° C.

$^1$H-NMR ($\delta$, CDCl$_3$): 1.3–2.1 (series of multiplets, 6H), 1.44 (s, 9H), 2.29 (s, 3H), 2.7–3.2 (m, 2H), 4.05 (AB, J$_{AB}$=17, $\Delta$v=66, 2H), 4.2–4.3 (m, 1H), 5.05 (m, 1H), 6.8–7.5 (m, 11H).

$^{13}$C-NMR ($\delta$, CDCl$_3$): 21.5, 28.0, 30.4, 32.2, 39.7, 45.2, 52.3, 58.4, 81.9, 117.1, 120.8, 127.0, 128.8, 128.9, 137.1, 155, 168.7, 175, (not all aromatic carbons assigned in this scan).

MS (%): 465 (9, parent), 374 (17), 185 (66), 170 (61), 107 (100), 91 (64), 83 (43), 57 (58).

HRMS calc'd for C$_{26}$H$_{40}$N$_3$O$_4$: 465.2593. Found: 465.26576.

EXAMPLE 13

3-((3-Chlorophenyl)ureido)-7-cyclohexyl-(N-t-butoxycarbonylmethyl)-hexahydroazepin-2-one Prepared in 87% yield, mp 75°–84° C.

$^1$H-NMR ($\delta$, CDCl$_3$): 1.3–2.1 (series of multiplets, 6H), 1.44 (s, 9H), 2.7–3.2 (m, 2H), 4.06 (AB, J$_{AB}$=17, $\Delta\gamma$=62, 2H), 4.2–4.3 (m, 1H), 5.05 (m, 1H), 6.9–7.6 (m, 11H).

MS (%): 485 (1, parent), 394 (22), 338 (23), 303 (34), (100), 170 (76), 127 (90), 91 (73), 57 (74), 56 (80).

HRMS calc'd for C$_{26}$H$_{37}$N$_3$O$_4$F$_3$: 485.20929. Found: 485.20705.

EXAMPLE 14

3-((3-Chlorophenyl)ureido)-7-phenyl-(N-t-butoxycarbonylmethyl)-hexahydroazepin-2-one (more polar diastereomer)

Prepared in 55% yield, mp 201°–203° C.

$^1$H-NMR ($\delta$, CDCl$_3$): 1.38 (s, 9H), 1.6–2.4 (series of multiplets, 6H), 4.05 (AB, J$_{AB}$=17, $\Delta$v=357, 2H), 4.5–4.7 (m, 2H), 6.6–7.8 (m, 11H).

IR (cm.$^{-1}$, KBr): 1719, 1680, 1625 (C=O).

MS (%): 471 (14, parent), 415 (47), 345 (52), 289 (100), 127 (51), 83 (45), 55 (39).

Anal. calc'd for C$_{25}$H$_{30}$N$_3$O$_4$Cl: C, 63.62; H, 6.41; N, 8.90. Found: C, 63.74; H, 6.49; N, 8.62.

EXAMPLE 15

3-(3-Tolylureido)-7-phenyl-(N-t-butoxycarbonylmethyl)hexahydroazepin-2-one (more polar diastereomer)

Prepared in 44% yield, mp 181°–183° C.

$^1$H-NMR ($\delta$, CDCl$_3$): 1.38 (s, 9H), 1.6–2.4 (series of multiplets, 6H), 2.24 (s, 3H), 4.01 (AB, J$_{AB}$=17, $\Delta$v=381. 2H), 4.5–4.6 (m, 1H), 4.62 (t, J=7, 1H), 6.57 (m, 1H), 6.76 (m, 1H), 7.0–7.5 (m, 9H).

IR (cm.$^{-1}$, KBr): 1721, 1680, 1636 (C=O).

Anal. calc'd for C$_{26}$H$_{33}$N$_3$O$_4$·0.25H$_2$O: C 68.47, H 7.40, N 9.21. Found: C 68.71, H. 7.47, N 9.22.

EXAMPLE 16

3-((3-Methoxyphenyl)ureido)-7-phenyl-(N-t-butoxycarbonylmethyl)-hexahydroazepin-2-one (more polar diastereomer)

Prepared in 44% yield, mp 169°–170° C.

$^1$H-NMR ($\delta$, CDCl$_3$): 1.38 (s, 9H), 1.6–2.4 (series of multiplets, 6H), 3.71 (s, 3H), 4.02 (AB, J$_{AB}$=17, $\Delta$v=375, 2H), 4.5–4.7 (m, 2H), 6.47 (m, 1H), 6.50 (m, 1H), 6.81 (m, 1H), 7.0–7.6 (m, 8H).

IR (cm.$^{-1}$, KBr): 1727, 1628 (C=O).

Anal. calc'd for C$_{26}$H$_{33}$N$_3$O$_5$: C, 66.79; H, 7.11; N, 8.99. Found: C, 66.59; H, 7.12; N, 8.92.

EXAMPLE 17

3-((3-Methoxyphenyl)ureido)-7-phenyl -(N-t-butoxycarbonylmethyl)-hexahydroazepin-2-one (less polar diastereomer)

Prepared in 39% yield, mp 180°–90° C.

$^1$H-NMR ($\delta$, CDCl$_3$): 1.27 (s, 9H), 1.6–2.4 (series of multiplets, 6H), 3.69 (s, 3H), 3.57 (AB, J$_{AB}$=17, $\Delta$v=226, 2H), 5.01 (m, 1H), 5.08 (m, 1H), 6.45 (m, 1H), 6.8 (m, 2H), 7.0–7.6 (m, 8H).

IR (cm.$^{-1}$, KBr): 1741, 1640, 1605 (C=O).

MS (%): 467 (11, parent), 159 (32), 123 (100), 117 (25).

Anal. calc'd for C$_{26}$H$_{33}$N$_3$O$_5$·0.5H$_2$O: C, 65.53; H, 7.19; N, 8.82. Found: C, 65.44; H, 6.952; N, 8.84.

EXAMPLE 18

3-((3-Chlorophenyl)ureido)-7-phenyl-(N-t-butoxycarbonylmethyl)-hexahydroazepin-2-one (less polar diastereomer)

Prepared in 19% yield, as a foam.

$^1$H-NMR ($\delta$, CDCl$_3$): 1.26 (s, 9H), 1.6–2.4 (series of multiplets, 6H), 3.51 (AB, J$_{AB}$=17, $\Delta$v=195, 2H), 5.00 (m, 1H), 5.08 (m, 1H), 6.8–7.4 (m, 9H), 7.98 (broad s, 1H), 8.13 (broad s, 1H).

$^{13}$C-NMR ($\delta$, CDCl$_3$): 27.1, 27.8, 31.1, 31.8, 46.8, 52.7, 60.5, 61.9, 81.7, 117.2, 117.3., 117.4, 119.4, 122.5, 122.8, 128.7, 129.1, 129.79, 129.82, 134.4, 134.5, 138.1, 140.1, 140.5, 153.0, 155.2, 168.5, 175.2.

IR (cm.$^{-1}$, KBr): 1741, 1629, 1598 (C=O).

MS (%): 471 (3, parent), 345 (20), 129 (35), 127 (100), 117 (22), 83 (41).

HRMS calc'd for $C_{25}H_{30}N_3O_4Cl$: 471. 19411. Found: 471. 19455.

EXAMPLE 19

3-(3-Tolylureido)-7-phenyl-(N-t-adamantyl) carbonylmethyl)-hexahydroazepin-2-one Prepared in 42% yield, mp 120°–130° C.

$^1$H-NMR (δ, CDCl$_3$): 1.4–2.4 (series of multiplets, 20H), 2.23 (s, 3H), 3.71 (AB, $J_{AB}$=17, Δν=213, 2H), 4.75 (m, 1H), 5.04 (m, 1H), 5.1 (m, 1H), 6.75 (m, 2H), 7.0–7.6 (m, 9H).

IR (cm.$^{-1}$, KBr): 1750, 1650 (C=O).

MS (%): 529 (8, parent), 159 (46), 135 (49), 133 (47), 117 (31), 107 (100), 85 (39), 83 (39).

Anal. calc'd for $C_{32}H_{39}N_3O_4 \cdot 0.5H_2O$: : C, 71.35; H, 7.48; N, 7.80. Found: C, 71.72; H, 7.33; N, 7.80.

EXAMPLE 20

3-(3-Tolylureido)-7-phenyl-(N-(1-adamantyl) carbonylmethyl)-hexahydroazepin-2-one Prepared in 3% yield, as a foam.

$^1$H-NMR (δ, CDCl$_3$): 1.4–2.4 (series of multiplets, 20H), 2.26 (s, 3H), 3.57 (AB, $J_{AB}$=17, Δν=250, 2H), 5.02 (m, 1H), 5.1 (m, 1H), 6.7–6.8 (m, 2H), 7.1–7.4 (m, 9H). IR (cm.$^{-1}$, KBr): 1745, 1650 (C=O).

MS (%): 529 (14, parent), 378 (60), 159 (78), 135 (100), 107 (60).

HRMS calc'd for $C_{32}H_{39}N_3O_4$: 529.29403. Found: 529.2902.

EXAMPLE 21

3-(3-Tolylureido)-7-phenyl-(N-(1-adamantyl) carboxamidomethyl)-hexahydroazepin-2-one Prepared in 28% yield, mp 145°–154° C.

$^1$H-NMR (δ, CDCl$_3$): 1.4–2.4 (series of multiplets, 20H), 2.245 (s, 3H), 3.50 (AB, $J_{AB}$=16, Δν=174, 2H), 5.03 (m, 1H), 5.1 (m, 1H), 5.26 (s, 1H), 6.7–6.8 (m, 2H), 7.1–7.7 (m, 9H).

IR (cm.$^{-1}$, KBr): 1645 (very broad) (C=O)

MS (%): 528 (<1, parent), 203 (36), 133 (100), 132 (30), 117 (44), 107 (61), 104 (31).

Anal. calc'd for $C_{33}H_{40}N_4O_3 \cdot 0.5H_2O$: C, 71.48; H, 7.69; N, 10.42. Found: C, 71.37; H, 7.80; N, 10.29.

EXAMPLE 22

4-Phenyl-6-methyl-1,2,3,4-tetrahydronaphth-1-one

Prepared in analogy with a procedure in JACS, 69, 74 (1947) as shown in Scheme 4:

A. 3-Carboethoxy-(4-phenyl, 4-(3-methylphenyl))-but-3-enoic acid

To a 250 mL round-bottomed flask equipped with condenser and N$_2$ inlet were added 100 mL t-butanol, 12.57 g (112 mmol) potassium t-butoxide, 20 g (102 mmol) 3-methylbenzophenone, and 21.31 g (122 mmol) diethyl succinate. The reaction was refluxed for 14 hours, cooled, and acidified with HCl, then partitioned between water and ether. The organic layer was washed with 1N aqueous sodium hydroxide solution, which was then acidified and extracted into ether. The organic layer was dried and concentrated to an orange oil which was used directly.

B. (4-Phenyl, 4-(3-methylphenyl))-but-3-enoic acid

The above oil was heated to reflux in a solution of 60 mL acetic acid, 60 mL 48% hydrobromic acid, and 50 mL additional acetic acid for solubility for 14 hours. The brown oil that separated on cooling was isolated, dissolved in ethyl acetate, washed with water, then with 2% aqueous sodium hydroxide solution. The basic aqueous phase was acidified, extracted into ethyl acetate, dried, and concentrated. The product was a mixture of olefin isomers by NMR:

$^1$H-NMR (δ, CDCl$_3$): 2.27 and 2.29 (s, 3H), 3.19 (m, 2H), 6.18 (t, J=7, 1H), 6.8–7.4 (m, 9H).

C. (4-Phenyl, 4-(3-methylphenyl))-butanoic acid

The above oil (25.7 g) was hydrogenated at 30 p.s.i. hydrogen in ethyl acetate with 1.25 g 10% palladium-on-carbon for 2 hours. Filtration through Celite and concentration, followed by chromatography on silica gel using methanol/methylene chloride as eluant afforded an oil which was crystallized from heptane, 4.70 g (18%), M.P. 96°–100° C.

$^1$H-NMR (δ, CDCl$_3$): 2.35 (s, 3H), 2.2–2.3 (m, 4H), 3.95 (t, J=7, 1H), 7.0–7.4 (m, 9H).

$^{13}$C-NMR (δ, CDCl$_3$): 21.6, 30.3, 32.6, 50.4, 124.8, 126.5, 127.3, 127.9, 128.5, 128.6, 138.2, 143.9, 144.2, 180.3.

IR (cm.$^{-1}$, KBr): 1720 (C=O).

MS (%): 254 (parent, 23), 182 (100), 165 (23), 32 (36), 28 (100).

Anal. calc'd for $C_{17}H_{18}O_2$: C 80.28, H 7.13. Found: C 80.54, H 7.05.

D. 4-Phenyl-6-methyl-1,2,3,4-tetrahydronaphth-1-one:

To a 250 mL round-bottomed flask equipped with condenser and N$_2$ inlet were added 8.2 g (32.3 mmol) (4-phenyl, 4-(3-methylphenyl))-butanoic acid, 54 mL toluene, and 4.6 g (38.64 mmol) thionyl chloride. The reaction was refluxed for 1 hour, cooled, and concentrated. The oil was dissolved in 15 mL carbon disulfide, and added dropwise to a slurry of 29.98 g (225 mmol) aluminum chloride in 50 mL carbon disulfide which had been cooled to 0° C. The reaction was allowed to stand 16 hours, poured onto ice, and partitioned between water and ethyl acetate. The organic phase was washed with water, aqueous sodium bicarbonate solution, and water, then dried and evaporated. The oil was chromatographed on silica gel using hexane/ethyl acetate as eluant to afford an oil, 4.03 g (53%).

$^1$H-NMR (δ, CDCl$_3$): 2.28 (s, 3H), 2.2–2.7 (m, 4H), 4.24 (m, 1H), 6.8–7.4 (m, 7H), 8.02 (d, J=7, 1H).

$^{13}$C-NMR (δ, CDCl$_3$): 21.8, 31.9, 36.4, 36.5, 45.2, 126.8, 128.1, 128.5, 128.6, 129.9, 130.6, 143.8, 144.5, 146.2, 197.8.

IR (cm.$^{-1}$, KBr): 1680 (C=O).

MS (%): 236 (parent, 96), 208 (92), 194 (42), 166 (43).

E. 4-Phenyl-6-methyl-1,2,3,4-tetrahydronaphth-1-one oxime

To a 125 mL round-bottomed flask equipped with condenser and N$_2$ inlet were added 4.3 g (18.29 mmol) 4-phenyl-6-methyl-1,2,3,4-tetrahydronaphth-1-one, 46 mL methanol, 2.95 g (29.26 mmol) triethylamine, and 2.02 g (29.26 mmol) hydroxylamine hydrochloride. The reaction was stirred at room temperature for 3 days, evaporated, partitioned between ethyl acetate and water, and the aqueous layer extracted with fresh ethyl acetate. The combined organic layer was dried over sodium sulfate and evaporated to an oil, 4.57 g (100%).

$^1$H-NMR (d, CDCl$_3$): 2.1–2.3 (m, 2H), 2.28 (s, 3H), 2.8–3.0 (m, 2H), 4.17 (m, 1H), 6.8–7.4 (m, 7H), 7.95 (d, J=7, 1H).

$^{13}$C-NMR (d, CDCl$_3$): 21.1, 21.4, 29.6, 45.0, 126.5, 128.0, 128.1, 128.5, 129.2, 129.9, 139.7, 141.4, 144.0, 155.3.

IR (cm.$^{-1}$, KBr): 1610 (C=N).

MS (%): 251 (parent, 94), 234 (32), 156 (17), 91 (17).

HRMS: Calc'd. for $C_{17}H_{17}NO$: 251.1310. Found: 251.13022.

F. 5-phenyl-7-methyl-2,3,4,5-tetrahydro-1H-(1)benzazepin-2-one

To a 250 mL round-bottomed flask equipped with $N_2$ inlet were added 4.5 g (18.3 mmol) 4-phenyl-6-methyl-1,2,3,4-tetrahydronaphth-1-one oxime and 59.45 g polyphosphoric acid. The mixture was heated in a 130° C. oil bath for 25 minutes, then poured onto ice and stirred until homogeneous. The mixture was extracted with ethyl acetate, and the organic layer washed with water and brine, dried over sodium sulfate, and evaporated. The residue was chromatographed on silica gel using hexane/ethyl acetate as eluant to afford an oil, 2.20 g (49%), which could be crystallized from methylene chloride and isopropyl ether to afford a solid, mp 169°–173° C.

$^1$H-NMR (δ, CDCl$_3$): 2.16 (s, 3H), 2.4–2.6 (m, 4H), 4.40 (m, 1H), 6.6 and 7.0–7.4 (m, 8H), 9.15 (bs, 1H).

$^{13}$C-NMR (δ, CDCl$_3$): 21.1, 32.9, 33.9, 45.0, 121.9, 127.0, 127.9, 128.6, 129.0, 129.1, 135.0, 135.2, 136.5, 141.2, 175.8.

IR (cm.$^{-1}$, KBr): 1680 (C=O).

MS (%): 252 (parent+1, 100), 196 (10), 147 (10), 135 (14), 119 (13), 103 (12).

Anal. calc'd for $C_{17}H_{17}NO$: C 81.24, H 6.82, N 5.57. Found: C 81.04, H 6.69, N 5.47.

The remainder of the synthesis was carried out as described in Example 1:

G. 3-Bromo-5-phenyl-7-methyl-2,3,4,5-tetrahydro-1H-(1)benzazepin-2-one

M.P. 205°–211° C., 62% yield.

$^1$H-NMR (δ, CDCl$_3$): 2.13 (s, 3H), 2.83 (m, 1H), 3.09 (m, 1H), 4.42 (m, 1H), 4.62 (m, 1H), 6.6 and 7.0–7.4 (m, 8H), 8.99 (bs, 1H).

$^{13}$C-NMR (δ, CDCl$_3$): 21.1, 45.0, 46.1, 47.3, 122.5, 127.4, 128.3, 128.6, 128.8, 128.9, 133.5, 133.6, 135.8, 136.4, 139.3, 169.3.

IR (cm.$^{-1}$, KBr): 1678 (C=O).

MS (%): 330/332 (parent, Br$^{79}$/Br$^{81}$, 100/98), 251 (26), 137 (32), 119 (32), 85 (27).

Anal. calc'd for $C_{17}H_{16}NOBr$: C 61.83, H 4.88, N 4.24. Found: C 61.79, H 4.57, N 4.09.

H. N-t-Butyl 2-[3-bromo-2-oxo-5-phenyl-7-methyl-2,3,4,5,-tetrahydro-1H-(1)benzazepin-1-yl]ethanoic acid amide M.P. 129°–133° C., 93% yield.

$^1$H NMR (δ, CDCl$_3$): 1.33 (s, 9H), 2.14 (s, 3H), 2.83 (m, 1H), 3.01 (m, 1H), 4.3–4.5 (m, 2H), 4.59 (m, 1H), 4.66 (m, 1H), 6.14 (bs, 1H), 6.48 (bs, 1H), 7.0–7.4 (m, 8H). $^{13}$C-NMR (δ, CDCl$_3$): 21.2, 28.7, 43.9, 45.7, 47.3, 51.5, 54.8, 123.0, 127.3, 128.3, 128.7, 128.8, 128.9, 129.0, 137.4, 137.5, 138.4, 139.1, 167.1, 168.2.

IR (cm.$^{-1}$, KBr): 1662 (C=O).

MS (%): 443/445 (parent, Br$^{79}$/Br$^{81}$, 90/92), 370/372 (Br$^{79}$/Br$^{81}$, 100/98), 290 (50), 262 (45), 134 (65).

Anal. calc'd for $C_{23}H_{27}N_2O_2Br\cdot 1/3H_2O$: C 61.47, H 6.21, N 6.23. Found: C 61.20, H 6.12, N 5.96.

I. N-tert-butyl-2-[3-azido-2-oxo-5-phenyl-7-methyl-2,3,4,5-tetrahydro-1H-(1) benzazepin-1-yl]ethanoic acid amide Foam, mixture of diastereomers, 81% yield.

$^1$H-NMR (δ, CDCl$_3$): 1.27, 1.32 (s's, 9H), 2.12, 2.37 (s's, 3H), 2.78 (m, 1H), 2.95 (m, 1H), 2.98 (AB$_q$, J$_{AB}$=15, Δv=279, part of 2H), 3.82, 3.96, 4.06, and 4.64 (multiplets, 2H), 4.35 (s, rest of 2H), 6.17 (bs, 1H), 6.45 (bs, 1H), 7.0–7.4 (m, 8H).

$^{13}$C-NMR (δ, CDCl$_3$): 21.0, 21.2, 28.6, 28.7, 35.5, 39.8, 41.9, 43.7, 51.3, 51.5, 54.6, 58.3, 59.0, 60.4, 123.0, 125.6, 126.1, 126.5, 127.3, 127.33, 127.4, 128.2, 128.3, 128.4, 128.5, 128.6, 128.65, 128.7, 128.8, 128.9, 129.58, 129.64, 130.9, 137.2, 137.6, 137.7, 138.5, 139.4, 141.1, 167.1, 167.9, 169.9, 170.4.

IR (cm.$^{-1}$, KBr): 2098 (N$_3$), 1660 (C=O).

MS (%): 406 (parent+1, 74), 380 (43), 347 (41), 333 9100), 249 (45), 234 (62), 222 (77), 22o (74), 2o8 (79), 144 (51), 132 (41), 105 (47), 91 (90).

HRMS calc'd for $C_{23}H_{27}N_5O_2$: 405.2165. Found: 405.21622.

J. N-tert-butyl-2-[3-amino-2-oxo-5-phenyl-7-methyl-2,3,4,5-tetrahydro-1H-(1)benzazepin-1-yl]ethanoic acid amide M.P. 100°–110° C., mixture of diastereomers, 29% yield.

$^1$H-NMR (δ, CDCl$_3$): 1.24, 1.31 (s's, 9H), 2.11, 2.35 (s's, 3H), 2.62 (bs, 2H), 2.6–2.8 (m, 2H), 3.2–3.4 (m, 2H), 4.0–4.5 (m, 4H), 6.09 (bs, 1H), 6.4 (bs, 1H), 7.0–7.4 (m, 8H).

IR (cm.$^{-1}$, KBr): 1660 (C=O).

MS (%): 379 (parent, 2), 336 (17), 235 916), 202 (22), 32 (35), 28 (100).

HRMS calc'd. for $C_{23}H_{29}N_2O_2$: 379.2260. Found: 379.22848.

Anal. calc'd for $C_{23}H_{29}N_3O_2\cdot 2/3H_2O$: C 70.56, H 7.81, N 10.73. Found: C 70.64, H 7.47, N 10.04 (–0.69).

K. N-tert-butyl-2-[3-(3-(3-tolyl)ureido)-2-oxo-5-phenyl-7-methyl-2,3,4,5-tetra-hydro-1H-(1)benzazepin-1-yl]ethanoic acid amide Prepared as a mixture of diastereomers, one of which precipitated from the reaction mixture (more polar); the other was purified by chromatography (less polar).

More polar isomer, M.P. 280°–283° C., 45.5% yield.

$^1$H-NMR (δ, CDCl$_3$): 1.30 (s, 9H), 2.11 (s, 3H), 2.22 (s, 3H), 2.8–3.2 (m, 2H), 3.90 (m, 1H), 4.34 (AB$_q$, J$_{AB}$=16, Δv=59, 2H), 4.62 (m, 1H), 6.4–6.8 (multiplets, 3H), 7.0–7.4 (m, 12H).

IR (cm.$^{-1}$, KBr): 1640 broad (C=O).

FAB MS (%): 513 (parent+1, 7), 380 (98), 307 (53), 155 (51), 119 (100).

HRMS calc'd for $C_{31}H_{36}N_4O_3$: 512.27541. Found: 512.27528.

Anal. calc'd for $C_{31}H_{36}N_4O_3\cdot 2/3H_2O$: C 70.97, H 7.17, N 10.68. Found: C 70.80, H 6.71 (–0.46), N 10.39.

Less polar isomer, M.P. 130°–135° C., 42% yield.

$^1$H-NMR (d, CDCl$_3$): 1.26 (s, 9H), 2.21 (s, 3H), 2.38 (s, 3H), 2.77 (m, 1H), 3.01 (m, 1H), 3.22 (AB$_q$, J$_{AB}$=16, Δv=287, 2H), 4.15 (m, 1H), 4.60 (m, 1H), 5.89 (bs, 1H), 6.5–7.3 (m, 13H), 7.67 (bs, 1H).

$^{13}$C-NMR (d, CDCl$_3$): 21.0, 21.4, 28.6, 37.1, 44.4, 50.2, 51.6, 53.6, 116.7, 123.4, 123.5, 126.3, 126.4, 128.3, 128.6, 129.4, 131.39, 131.43, 137.7, 137.9, 138.5, 138.6, 139.1, 141.9, 155.4, 167.6, 173.0.

IR (cm.$^{-1}$, KBr): 1640 broad (C=O).

FAB MS (%): 513 (parent+1, 78), 440 (98), 380 (46), 305 (44), 251 (77), 234 (93), 222 (67), 220 (45), 208 (100), 144 (44), 107 (54).

HRMS calc'd. for $C_{31}H_{36}N_4O_3$: 512.27541. Found: 512.28240.

Anal. calc'd for $C_{31}H_{36}N_4O_3\cdot 1/2H_2O$: C 71.58, H 7.15, N 10.74. Found: C 71.55, H 7.10, N 10.33 (–0.41).

EXAMPLE 23

N-tert-butyl-2-[3-(3-(3-chlorophenyl)ureido)-2-oxo-5-phenyl-7-methyl-2,3,4,5-tetrahydro-1H-(1)benzazepin-1-yl]ethanoic acid amide Prepared as a mixture of diastereomers from the title compound of Example 22J, one of which precipitated from the reaction mixture (more polar); the other was purified by chromatography (less polar).

More polar isomer, M.P. 282°–285° C., 38% yield.

$^1$H-NMR (δ, CDCl$_3$): 1.28 (s, 9H), 2.10 (s, 3H), 2.8–3.2 (m, 2H), 3.90 (m, 1H), 4.32 (AB$_q$, J$_{AB}$=16, Δv=52, 2H), 4.57 (m, 1H), 6.42 (bs, 1H), 6.6–7.4 (m, 14H).

IR (cm.$^{-1}$, KBr): 1640 broad (C=O).

FAB MS (%): 533/535 (parent+1, Cl$^{35}$/Cl$^{37}$, 9/4), 380 (52), 307/309 (29/11), 155 (70), 135 (46), 119 (100), 103 (68).

Anal. calc'd for C$_{30}$H$_{33}$N$_4$O$_3$Cl•1/2H$_2$O: C 66.47, H 6.32, N 10.34. Found: C 66.17, H 6.25, N 10.04.

Less polar isomer, M.P. 155°–165° C., 46% yield.

$^1$H-NMR (δ, CDCl$_3$): 1.28 (s, 9H), 2.39 (s, 3H), 2.8–3.0 (m, 2H), 3.28 (AB$_q$, J$_{AB}$=16, Δv=281, 2H), 4.11 (m, 1H), 4.38 (m, 1H), 5.83 (bs, 1H), 6.6–7.2 (m, 12H), 7.57 (bs, 1H), 7.98 (bs, 1H).

$^{13}$C-NMR (δ, CDCl$_3$): 21.0, 28.7, 36.8, 44.4, 50.4, 51.8, 53.2, 116.9, 122.1, 126.3, 126.5, 128.3, 129.5, 131.5, 134.3, 137.7, 137.8, 137.9, 138.4, 140.7, 141.9, 155.1, 167.4, 173.3.

IR (cm.$^{-1}$, KBr): 1640 broad (C=O).

FAB MS (%): 533/535 (parent+1, Cl$^{35}$/Cl$^{37}$, 37/15), 460/462 (81/31), 380 (33), 307 (61), 251 (61), 234 (100), 222 (62), 208 (99), 91 (51).

Anal. calc'd for C$_{30}$H$_{33}$N$_4$O$_3$Cl: C 67.598, H 6.24, N 10.51. Found: C 67.50, H 6.18, N 10.14.

EXAMPLE 24

N-tert-butyl-2-[3-(3-(3-methoxyphenyl)ureido)-2-oxo-5-phenyl-7-methyl-2,3,4,5-tetrahydro-1H-(1)benzazepin-1-yl]ethanoic acid amide Prepared as a mixture of diastereomers from the title compound of Example 22J, one of which precipitated from the reaction mixture (more polar); the other was purified by chromatography (less polar).

More polar isomer, M.P. 283°–286° C., 47% yield.

$^1$H-NMR (δ, CDCl$_3$): 1.31 (s, 9H), 2.11 (s, 3H), 2.8–3.2 (m, 2H), 3.7 (singlets, 3H), 3.50 (m, 1H), 4.29 (AB$_q$, J$_{AB}$=15, Δv=138, 2H), 4.46 (m, 1H), 6.4–7.4 (multiplets, 15H).

IR (cm.$^{-1}$, KBr): 1640 broad (C=O).

FAB MS (%): 529 (parent+1, 7), 380 (100), 307 (92), 251 (47), 208 (42).

Anal. calc'd for C$_{31}$H$_{36}$N$_4$O$_4$•1/2H$_2$O: C 69.25, H 6.94, N 10.42. Found: C 69.22, H 6.59, N 10.24.

Less polar isomer, M.P. 120°–125° C., yield 37%.

$^1$H-NMR (δ, CDCl$_3$): 1.25 (s, 9H), 2.38 (s, 3H), 2.79 (m, 1H), 3.03 (m, 1H), 3.25 (AB$_q$, J$_{AB}$=16, Δvn=260, 2H), 3.68 (s, 3H), 4.17 (m, 1H), 4.62 (m, 1H), 5.84 (bs, 1H), 6.5–7.3 (m, 13H), 7.80 (bs, 1H).

13C-NMR (δ, CDCl$_3$): 21.0, 28.6, 37.2, 44.3, 50.1, 51.6, 53.6, 55.1, 104.7, 108.8, 111.5, 124.5, 126.3, 126.4, 128.3, 129.3, 129.4, 137.7, 138.0, 138.5, 140.6, 141.9, 155.2, 160.1, 167.5, 172.9.

IR (cm.$^{-1}$, KBr): 1640 broad (C=O).

FAB MS (%): 529 (parent+1, 83), 456 (100), 380 (44), 307 (70), 251 (52), 234 (67), 208 (65).

Anal. calc'd for C$_{31}$H$_{36}$N$_4$O$_4$•1/3H$_2$O: C 68.87, H 6.96, N 10.36. Found: C 68.94, H 6.67, N 10.00.

EXAMPLE 25

N-tert-butyl-2-[3-(3-(3-tolyl)ureido)-2-oxo-5-(3-chlorophenyl)-2,3,4,5-tetrahydro-1H-(1)benzazepin-1-yl]ethanoic acid amide A. 4-Phenyl-6-chloro-1,2,3,4-tetrahydronaphth-1-one Prepared in analogy with Example 22 above by treatment of (4-phenyl,4-(3-chlorophenyl))-butanoic acid (prepared in analogy with 4-phenyl, 4-(3-methylphenyl)-butanoic acid as described above in Example 22), with thionyl chloride in toluene followed by cyclization with aluminum chloride in carbon disulfide to afford the desired 4-(3-chlorophenyl)-1,2,3,4-tetrahydronaphth-1-one and the isomeric product 4-phenyl-6-chloro-1,2,3,4-tetrahydronaphth-1-one as an inseparable mixture in 53% yield, which was converted to the oximes and separated.

B. 4-(3-Chlorophenyl)-1,2,3,4-tetrahydronaphth-1-one oxime

M.P. 129°–131° C., 28% yield.

$^1$H-NMR (δ, CDCl$_3$): 1.56 (bs, 1H), 2.0–2.3 (m, 2H), 2.7–2.9 (m, 2H), 4.18 (m, 1H), 6.8–7.4 and 8.0 (m, 8H).

$^{13}$C-NMR (δ, CDCl$_3$): 21.2, 29.3, 44.8, 124.2, 126.7, 127.2, 128.6, 129.3, 129.8, 130.7, 134.5, 140.7, 146.0, 154.9.

IR (cm.$^{-1}$, KBr): 1598 (C=N).

MS (%): 271/273 (parent, Cl$^{35}$/Cl$^{37}$, 100/35), 254 (42), 217 (24), 190 (29).

Anal. calc'd for C$_{16}$H$_{14}$NOCl: C 70.72, H 5.19, N 5.15. Found: C 70.70, H 5.01, N 5.22.

C. 4-Phenyl-6-chloro-1,2,3,4-tetrahydronaphth-1-one oxime

Oil, 27% yield.

$^1$H-NMR (δ, CDCl$_3$): 2.0–2.3 (m, 2H), 2.77 (t, J=7, 2H), 4.07 (m, 1H), 6.8–7.3 and 7.86 (m, 8H).

(3-Chlorophenyl) compounds:

D. 5-(3-Chlorophenyl)-2,3,4,5-tetrahydro-1H-(1)benzazepin-2-one

Prepared as in Example 22, M.P. 174°–176° C., yield 51%.

Anal. calc'd for C$_{16}$H$_{14}$NOCl: C 70.72, H 5.19, N 5.15. Found: C 70.90, H 4.90, N 5.02.

E. 3-Bromo-5-(3-chlorophenyl)-2,3,4,5-tetrahydro-1H-(1)benzazepin-2-one

M.P. 154°–158° C., 51% yield.

Anal. calc'd for C$_{16}$H$_{13}$NOBrCl: C 54.81, H 3.74, N 3.99. Found: C 55.48 (+0.67), H 3.46, N 3.87.

F. N-t-Butyl 2-[3-bromo-2-oxo-5-(3-chlorophenyl)-2,3,4,5,-tetrahydro-1H-(1)benzazepin-1-yl]ethanoic acid amide M.P. 148°–152° C. (from cyclohexane), 57% yield.

Anal. calc'd for C$_{22}$H$_{24}$N$_2$O$_2$BrCl•1/2 cyclohexane: C 59.36, H 5.98, N 5.54. Found: C 59.26, H 6.16, N 5.54.

G. N-tert-butyl-2-[3-azido-2-oxo-5-(3-chlorophenyl)-2,3,4,5-tetrahydro-1H-(1)benzazepin-1-yl]ethanoic acid amide M.P. 132°–135° C., 72.5% yield.

Anal. calc'd for C$_{22}$H$_{24}$N$_5$O$_5$Cl: C 62.04, H 5.68, N 16.44. Found: C 62.12, H 5.56, N 16.51.

H. N-tert-butyl-2-[3-amino-2-oxo-5-(3-chlorophenyl)-2,3,4,5-tetrahydro-1H-(1)benzazepin-1-yl]ethanoic acid amide The reduction was carried out with 1 equivalent of triphenylphosphine and water in tetrahydrofuran overnight at room temperature to give a foam in 95% yield.

HRMS calc'd for C$_{22}$H$_{27}$N$_3$O$_2$Cl: 400.1786. Found: 400.17876.

I. N-tert-butyl-2-[3-(3-(3-tolyl)ureido)-2-oxo-5-(3-chlorophenyl)-2,3,4,5-tetrahydro-1H-(1)benzazepin-1-yl]ethanoic acid amide Prepared from a single diastereomer of the amino compound, which gave a diastereomer corresponding to the less polar isomer in Example 22K, M.P. 251°–253° C., 85% yield.

¹H-NMR (δ, CDCl₃, TFA): 1.33 (s, 9H), 2.33 (s, 3H), 2.79 (m, 1H), 2.96 (m, 1H), 3.33 (AB$_q$, J$_{AB}$=16, Δv=150, 2H), 4.22 (m, 1H), 4.58 (m, 1H), 6.7–7.5 (m, 15H).

¹³C-NMR (δ, CDCl₃, TFA): 20.7, 28.0, 36.3, 43.4, 50.5, 53.4, 53.5, 121.4, 124.2, 124.8, 125.1, 125.9, 127.2, 128.6, 129.5, 129.8, 130.0, 131.0, 134.1, 134.8, 137.2, 139.2, 140.6, 142.7, 158.2, 169.1, 173.6.

IR (cm.⁻¹, KBr): 1640 broad (C=O).

FAB MS (%): 533/535 (parent, Cl³⁵/Cl³⁷, 32/13) 155, (46), 119 (100), 103 (45).

Anal. calc'd for C₃₀H₃₃N₄O₃Cl·1/3H₂O: C 66.84, H 6.29, N 10.39. Found: C 66.90, H 6.25, N 10.32.

EXAMPLE 26

N-tert-butyl-2-[3-(3-(3-chlorophenyl)ureido)-2-oxo-5-(3-chlorophenyl)-2,3,4,5-tetrahydro-1H-(1)benzazepin-1-yl]ethanoic acid amide Prepared from a single diastereomer of the amino compound, which gave a diastereomer corresponding to the less polar isomer in Example 22K, M.P. 240°–243° C., 84% yield.

¹H-NMR (δ, CDCl₃, TFA): 1.33 (s, 9H), 2.79 (m, 1H), 3.02 (m, 1H), 3.34 (AB$_q$, J$_{AB}$=16, Δv=143, 2H), 4.25 (m, 1H), 4.59 (m, 1H), 6.7–7.5 (m, 15H).

¹³C-NMR (δ, CDCl₃, TFA): 27.8, 36.6, 43.3, 44.0, 50.3, 53.4, 53.5, 121.2, 123.4, 124.2, 124.7, 126.0, 126.8, 127.2, 129.9, 130.0, 130.7, 131.1, 134.8, 135.5, 136.4, 137.2, 139.2, 142.7, 157.3, 169.1, 173.9.

IR (cm.⁻¹, KBr): 1640 broad (C=O).

FAB MS (%): 553/554/555/556/557 (parent+1, Cl³⁵/Cl³⁷, 14/6/12/3/2), 309 (16), 155 (60), 135 (30), 119 (100), 103 (42).

Anal. calc'd for C₂₉H₃₀N₄O₃Cl₂·1/3H₂O: C 62.26, H 5.52, N 10.01. Found: C 62.32, H 5.38, N 9.77.

EXAMPLE 27

N-tert-butyl-2-[3-(3-(3-methoxyphenyl)ureido)-2-oxo-5-(3-chlorophenyl)-2,3,4,5-tetrahydro-1H-(1)benzazepin-1-yl]ethanoic acid amide Prepared from a single diastereomer of the amino compound, which gave a diastereomer corresponding to the less polar isomer in Example 22K, M.P. 224°–227° C., 80% yield.

¹H-NMR (δ, CDCl₃, TFA): 1.32 (s, 9H), 2.77 (m, 1H), 2.97 (m, 1H), 3.31 (AB$_q$, J$_{AB}$=16, Δv=157, 2H), 3.83 (s, 3H), 4.21 (m, 1H), 4.55 (m, 1H), 6.7–7.5 (m, 15H).

¹³C-NMR (δ, CDCl₃, TFA): 27.9, 36.4, 43.4, 50.4, 53.4, 55.5, 109.9, 112.7, 116.4, 124.2, 124.8, 126.0, 127.2, 129.4, 129.9, 130.0, 130.7, 131.1, 134.8, 136.1, 137.2, 139.3, 142.7, 157.7, 169.1, 173.8.

IR (cm.⁻¹, KBr): 1640 broad (C=O).

FAB MS (%): 549/551 (parent, Cl³⁵/Cl³⁷, 45/17), 476 (23), 400 (22), 327 (25), 155 (50), 135 (32), 119 (100), 103 (47).

Anal. calc'd for C₃₀H₃₃N₄O₄Cl: C 65.63, H 6.06, N 10.20. Found: C 65.73, H 6.03, N 9.89.

EXAMPLE 28

N-tert-butyl-2-[3-(3-(3-ethylphenyl)ureido)-2-oxo-5-(3-chlorophenyl)-2,3,4,5-tetrahydro-1H-(1)benzazepin-1-yl]ethanoic acid amide Prepared from a single diastereomer of the amino compound, which gave a diastereomer corresponding to the less polar isomer in Example 22K, M.P. 223°–228° C., 77% yield.

¹H-NMR (δ, CDCl₃, TFA): 1.21 (t, J=7, 3H), 1.32 (s, 9H), 2.63 (q, J=7, 2H), 2.77 (m, 1H), 2.98 (m, 1H), 3.31 (AB$_q$, J$_{AB}$=16, Δv=174, 2H), 4.23 (m, 1H), 4.58 (m, 1H), 6.7–7.5 (m, 15H).

¹³C-NMR (δ, CDCl₃, TFA): 14.9, 27.9, 28.5, 36.4, 43.4, 50.4, 53.3, 53.4, 121.4, 123.7, 124.2, 124.8, 126.0, 127.1, 127.2, 129.4, 129.9, 130.0, 131.0, 134.5, 134.8, 137.2, 139.4, 142.7, 146.8, 158.1, 169.0, 173.7.

IR (cm.⁻¹, KBr): 1640 broad (C=O).

FAB MS (%): 547/549 (parent, Cl³⁵/Cl³⁷, 92/35) 474 (60), 400 (55), 327 (72), 119 (100).

Anal. calc'd for C₃₁H₃₅N₄O₃Cl: C 68.06, H 6.45, N 10.24. Found: C 67.98, H 6.35, N 10.05.

EXAMPLE 29

A. 5-phenyl-7-chloro-2,3,4,5-tetrahydro-1H-(1)benzazepin-2-one

Prepared from the title compound of Example 25C as in Example 25D, M.P. 184°–186° C. 58% yield.

Anal. calc'd for C₁₆H₁₄NOCl: C 70.72, H 5.19, N 5.15. Found: C 71.00, H 4.86, N 5.07.

B. 3-Bromo-5-phenyl-7-chloro-2,3,4,5-tetrahydro-1H-(1)benzazepin-2-one

M.P. 220°–223° C. 56% yield.

Anal. calc'd for C₁₆H₁₃NOClBr: C 54.81, H 3.74, N 3.99. Found: C 61.79, H 4.57, N 4.09.

C. N-t-Butyl 2-[3-bromo-2-oxo-5-phenyl-7-chloro-2,3,4,5,-tetrahydro-1H-(1)benzazepin-1-yl]ethanoic acid amide M.P. 125°–130° C. (from cyclohexane), 64% yield.

Anal. calc'd for C₂₂H₂₄N₂O₂ClBr·1/3 cyclohexane: C 58.61, H 5.74, N 5.70. Found: C 58.72, H 5.50, N 5.58.

D. N-tert-butyl-2-[3-azido-2-oxo-5-phenyl-7-chloro-2,3,4,5-tetrahydro-1H-(1)benzazepin-1-yl]ethanoic acid amide M.P. 167°–170° C., 38% yield.

Anal. calc'd for C₂₂H₂₄N₅O₂Cl·1/3H₂O: C 61.18, H 5.76, N 16.21. Found: C 61.28, H 5.56, N 15.91.

E. N-tert-butyl-2-[3-amino-2-oxo-5-phenyl-7-chloro-2,3,4,5-tetrahydro-1H-(1)benzazepin-1-yl]ethanoic acid amide Foam, 65% yield.

HRMS calc'd for C₂₂H₂₇N₃O₂Cl: 400.1786. Found: 400.17952.

F. N-tert-butyl-2-[3-(3-(3-tolyl)ureido)-2-oxo-5-phenyl-7-chloro-2,3,4,5-tetrahydro-1H-(1)benzazepin-1-yl]ethanoic acid amide Prepared from a single diastereomer of the amino compound, which gave a diastereomer corresponding to the less polar isomer in Example 22K, M.P. 155°–160° C., 82% yield.

¹H-NMR (δ, CDCl₃): 1.24 (s, 9H), 2.22 (s, 3H), 2.78 (m, 1H), 3.03 (m, 1H), 3.18 (AB$_q$, J$_{AB}$=16, Δv=279, 2H), 4.18 (m, 1H), 4.57 (m, 1H), 5.76 (bs, 1H), 6.7–7.4 (m, 14H).

¹³C-NMR (δ, CDCl₃): 21.5, 28.5, 36.9, 44.2, 50.1, 51.7, 53.5, 116.9, 120.7, 123.8, 126.2, 126.7, 128.5, 128.7, 129.0, 130.5, 133.1, 138.8, 139.7, 140.1, 141.0, 155.3, 167.2, 172.6.

IR (cm.⁻¹, KBr): 1640 broad (C=O).

FAB MS (%): 533/535 (parent, Cl³⁵/Cl³⁷, 100/39), 460 (74), 400 (56), 327 (72), 119 (68), 107 (72), 91 (67).

Anal. calc'd for C₃₀H₃₃N₄O₃Cl·1/3H₂O: C 66.84, H 6.29, N 10.39. Found: C 66.87, H 6.19, N 10.13.

EXAMPLE 30

N-tert-butyl-2-[3-(3-(3-chlorophenyl)ureido)-2-oxo-5-phenyl-7-chloro-2,3,4,5-tetrahydro-1H-(1)benzazepin-1-yl]ethanoic acid amide Prepared from a single diastereomer of the amino compound, which gave a diastereomer corresponding to the less polar isomer in Example 22K, M.P. 234°–236° C., 83% yield.

¹H-NMR (δ, CDCl₃): 1.27 (s, 9H), 2.8–3.0 (m, 2H), 3.24 (AB_q, J_AB=16, Δv=274, 2H), 4.21 (m, 1H), 4.55 (m, 1H), 5.76 (bs, 1H), 6.8–7.5 (m, 13H), 7.92 (bs, 1H).

¹³C-NMR (δ, CDCl₃): 28.7, 36.6, 44.3, 50.3, 52.0, 53.1, 53.5, 117.0, 119.1, 122.4, 125.8, 126.2, 126.9, 128.5, 129.0, 129.6, 130.7, 133.2, 134.3, 139.6, 140.0, 140.5, 140.9, 155.0, 167.0, 173.0.

IR (cm.⁻¹, KBr): 1640 broad (C=O). FAB MS (%): 553/554/555/556/557/558 (parent, Cl³⁵/Cl³⁷, 75/32/54/19/10), 400 (100), 327 (82), 254 (83), 228 (73).

Anal. calc'd for C₂₉H₃₀N₄O₃Cl₂·1/3H₂O: C 62.26, H 5.52, N 10.01. Found: C 62.49, H 5.40, N 9.70.

EXAMPLE 31

N-tert-butyl-2-[3-(3-(3-tolyl)ureido)-2-oxo-5-(4-fluorophenyl)-2,3,4,5-tetrahydro-1H-(1)benzazepin-1-yl]ethanoic acid amide A. 4-(4-Fluorophenyl)-1,2,3,4-tetrahydronaphth-1-one oxime Prepared as in Example 22 above from the known 4-(4-fluorophenyl)-1,2,3,4-tetrahydronaphth-1-one (see Koptyug, V. A. and Andreeva, T. P., Zh. Organich. Khim., 7, 2398–2403 (1971)) as shown in Scheme 5 in 93% yield, M.P. 154°–158° C. (from ethyl acetate/hexane).

¹H-NMR (δ, CDCl₃): 2.0–2.3 (m, 2H), 2.84 (m, 2H), 4.13 (m, 1H), 6.9–7.3 (m, 7H), 7.97 (m, 1H), 9.36 (bs, 1H).

¹³C-NMR (δ, CDCl₃): 21.3, 29.5, 44.3, 115.2, 115.5, 124.1, 127.1, 129.2, 129.6, 129.8, 129.9, 130.7, 139.4, 141.4, 155.1, 163.2.

IR (cm.⁻¹, KBr): 1602 (C=N).

MS (%): 255 (parent, 100), 238 (42), 183 (23).

HRMS calc'd for C₁₆H₁₄NOF: 255. 10595. Found: 255.10679.

B. 5-(4-Fluorophenyl)-2,3,4,5-tetrahydro-1H-(1)benzazepin-2-one

Prepared from the title compound of Example 31A as in Example 22F in 48% yield, M.P. 209–212° C. (from 2-propanol).

¹H-NMR (δ, CDCl₃): 2.4–2.6 (m, 4H), 4.2 (m, 1H), 6.75 and 7.0–7.3 (m, 8H), 8.41 (bs, 1H).

¹³C-NMR (δ, CDCl₃): 32.7, 33.9, 44.3, 115.3, 115.6, 122.0, 125.7, 127.4, 128.5, 130.2, 130.4, 136.6, 136.7, 137.3, 160.2, 160.4, 175.2.

IR (cm.⁻¹, KBr): 1680 (C=O).

MS (%): 255 (parent, 83), 213 (29), 200 (100), 198 (55), 183 (22).

Anal. calc'd for C₁₆H₁₄NOF: C 75.28, H 5.53, N 5.49. Found: C 75.20, H 5.50, N 5.35.

The remainder of the synthesis was carried out as described in Example 1:

C. 3-Bromo-5-(4-fluorophenyl)-2,3,4,5-tetrahydro-1H-(1)benzazepin-2-one

M.P. 170°–180° C. (from methylene chloride/hexane), 58% yield, mixture of diastereomers.

¹H-NMR (δ, CDCl₃): 2.8–3.2 (m, 2H), 4.50 (m, 1H), 4.65 (m, 1H), 6.7–7.4 (m, 8H), 8.97 and 9.23 (singlets, 1H).

¹³C-NMR (δ, CDCl₃): 43.8, 44.1, 44.3, 45.1, 46.2, 46.9, 115.4, 115.6, 115.7, 115.9, 122.7, 126.6, 127.9, 128.1, 128.2, 129.1, 129.6, 129.7, 129.8, 130.3, 130.5, 134.9, 135.0, 135.8, 136.2, 136.6, 160.4, 163.7, 169.3, 170.2.

IR (cm.⁻¹, KBr): 1690 (C=O).

MS (%): 333/335 (parent, Br⁷⁹/Br⁸¹, 46/50), 254 (100), 226 (100), 200 (60), 198 (77), 109 (60).

HRMS calc'd for C₁₆H₁₃NOFBr: 333. 01466. Found: 333.01409.

D. N-t-Butyl 2-[3-bromo-2-oxo-5-(4-fluorophenyl)-2,3,4,5,-tetrahydro-1H-(1)benzazepin-1-yl]ethanoic acid amide M.P. 215°–220° C. (from cyclohexane), 59% yield.

¹H-NMR (δ, CDCl₃): 1.32 (s, 9H), 2.8–3.0 (m, 2H), 4.2–4.6 (m, 3H), 4.77 (m, 1H), 6.04 (bs, 1H), 6.6 and 7.0–7.4 (m, 8H).

¹³C-NMR (δ, CDCl₃): 28.7, 43.1, 45.8, 47.0, 51.6, 54.6, 115.4, 115.7, 123.2, 127.5, 127.6, 128.1, 130.3, 130.4, 130.5, 134.9, 135.0, 137.7, 140.9, 163.6, 166.9, 167.9.

IR (cm.⁻¹, KBr): 1660 (C=O).

FAB MS (%): 447/449 (parent, Br⁷⁹/Br⁸¹, 21/23), 374/376 (100/94), 346/348 (48/46), 266 (93), 238 (44).

Anal. calc'd for C₂₂H₂₄N₂O₂BrF: C 59.07, H 5.41, N 6.26. Found: C 59.05, H 5.15, N 6.20.

E. N-tert-butyl-2-[3-azido-2-oxo-5-(4-fluorophenyl)-2,3,4,5-tetrahydro-1H-(1)benzazepin-1-yl]ethanoic acid amide M.P. 75°–85° C., mixture of diastereomers, 92% yield.

¹H-NMR (δ, CDCl₃): 1.28, 1.32 (s's, 9H), 2.4–2.9 (m, 2H and part of a 2H signal), 3.6, 3.77, 3.91, 4.12, 4.32, and 4.69 (multiplets for 2H and the remaining 2H signal), 6.0 (broad singlets, 1H), 6.6 and 6.8–7.4 (m, 8H).

¹³C-NMR (δ, CDCl₃): 28.6, 35.9, 39.9, 41.1, 43.2, 51.6, 53.6, 54.5, 58.2, 58.9, 115.1, 115.4, 115.7, 123.2, 125.9, 127.3, 127.5, 127.6, 127.7, 127.8, 127.9, 128.0, 129.3, 129.5, 130.2, 130.3, 130.4, 135.1, 137.5, 138.0, 140.2, 141.0, 166.9, 167.6, 169.8, 170.2.

IR (cm.⁻¹, KBr): 2100 (N₃), 1670 (C=O).

MS (%): 410 (parent+1, 55), 384 (35), 311 (19), 155 (50), 119 (100), 103 (40).

HRMS calc'd for C₂₂H₂₄N₅O₂F: 409. 1914. Found: 409. 1903.

F. N-tert-butyl-2-[3-amino-2-oxo-5-(4-fluorophenyl)-2,3,4,5-tetrahydro-1H-(1)benzazepin-1-yl]ethanoic acid amide The mixture of diastereomers was separated into an ethyl acetate insoluble, M.P. 290°–295° C., 32% yield, isomer A and an isopropyl ether insoluble, mp 215°–225° C., 32% yield, isomer B.

Isomer A:

¹H-NMR (δ, CDCl₃): 1.26 (s, 9H), 2.48 (m, 1H), 2.7 (broad s, 2H), 3.03 (m, 1H), 3.90 (m, 1H), 4.17 (AB_q, J_AB=16, Dn=20, 2H), 4.87 (m, 1H), 6.6 and 7.0–7.4 (m, 8H).

IR (cm.⁻¹, KBr): 1680 (C=O).

MS (%): 384 (parent+1, 100), 311 (44), 255 (19), 119 (20).

Isomer B:

¹H-NMR (δ, CDCl₃): 1.26 (s, 9H), 2.5 (m, 1H), 3.0–3.4 (m, 2H), 2.61 (m, 1H), 4.1–4.3 (m, 2H), 6.12 (broad s, 1H), 6.8–7.4 (m, 8H), 8.78 (broad s, 2H).

¹³C-NMR (d, CDCl₃): 22.8, 28.8, 43.2, 50.3, 51.8, 53.3, 115.1, 115.4, 125.2, 128.1, 128.2, 129.4, 130.7, 136.6, 137.8, 140.1, 159.7, 162.9, 167.5, 168.7.

IR (cm.⁻¹, KBr): 1680 (C=O).

MS (%): 383 (parent, 10), 340 (94), 267 (65), 261 (79), 255 (62), 239 (81), 224 (65), 212 (100), 188 (86), 57 (80).

Anal. calc'd for C₂₂H₂₆N₃O₂F·H₂CO₃: C 62.01, H 6.33, N 9.43. Found: C 62.00, H 6.61, N 9.37.

G. N-tert-butyl-2-[3-(3-(3-tolyl)ureido)-2-oxo-5-(4-fluorophenyl)-2,3,4,,5-tetrahydro-1H-(1)benzazepin-1-yl] ethanoic acid amide Prepared from each of the above isomers:

From isomer B, M.P. 302°–307° C. 69% yield.

¹H-NMR (δ, CDCl₃, TFA): 1.34 (s, 9H), 2.34 (s, 3H), 2.85 (m, 1H), 3.03 (m, 1H), 3.34 (AB_q, J_AB=16, Δv=147, 2H), 4.27 (m, 1H), 4.62 (m, 1H), 6.8–7.6 (m, 15H).

¹³C-NMR (δ, CDCl₃, TFA): 20.4, 27.5, 36.6, 42.9, 50.6, 53.4, 53.6, 115.2, 115.5, 121.5, 124.7, 125.3, 127.3, 127.4, 128.9, 129.5, 129.8, 131.0, 133.7, 136.1, 137.6, 139.1, 140.8, 160.0, 169.2, 173.5.

IR (cm.$^{-1}$, KBr): 1650 broad (C=O).

FAB MS (%): 516 (parent, 17), 340 (100), 267 (70), 239 (58), 212 (46).

Anal. calc'd for $C_{30}H_{33}N_4O_3F\cdot1/3H_2O$: C 68.95, H 6.49, N 10.72. Found: C 68.89, H 6.31, N 10.59.

From isomer A, M.P. 310°–315° C., 55% yield.

$^1$H-NMR (δ, CDCl$_3$, TFA): 1.35 (s, 9H), 2.32 (s, 3H), 2.93 (m, 2H), 4.4–4.7 (m, 4H), 6.8 and 7.0–7.5 (m, 15H).

$^{13}$C-NMR (δ, CDCl$_3$, TFA): 20.5, 27.7, 40.9, 41.2, 51.5, 53.5, 53.8, 115.5, 115.8, 121.7, 122.6, 125.4, 128.1, 128.9, 129.8, 129.9, 130.1, 130.2, 133.6, 133.7, 133.8, 137.4, 138.3, 140.8, 158.3, 160.6, 163.9, 169.0, 173.8.

IR (cm.$^{-1}$, KBr): 1650 broad (C=O).

FAB MS (%): 517 (parent+1, 2), 309 (15), 185 (20), 155 (58), (45), 119 (100), 103 (57).

Anal. calc'd for $C_{30}H_{33}N_4O_3F\cdot H_2CO_3$: C 65.81, H 6.34, N 10.07. Found: C 65.63, H 6.07, N 10.36.

EXAMPLE 32

N-tert-butyl-2-[3-(3-(3-chlorophenyl)ureido)-2-oxo-5-(4-fluorophenyl)-2,3,4,5-tetrahydro-1H-(1)benzazepin-1-yl]ethanoic acid amide Prepared from each of the above isomers in Example 31F:
From isomer B, M.P. 271°–273° C., 78% yield.

$^1$H-NMR (δ, CDCl$_3$,TFA): 1.35 (s, 9H), 2.84 (m, 1H), 3.05 (m, 1H), 3.35 (AB$_q$, J$_{AB}$=16, Δν=139, 2H), 4.30 (m, 1H), 4.64 (m, 1H), 6.8–7.6 (m, 15H).

$^{13}$C-NMR (δ, CDCl$_3$,TFA): 27.5, 36.8, 43.0, 50.5, 53.4, 53.8, 115.3, 115.5, 121.5, 123.7, 124.7, 127.1, 127.3, 127.4, 129.5, 129.8, 130.7, 131.0, 135.5, 136.0, 137.7, 139.1, 157.5, 160.0, 163.3, 169.3, 173.9.

IR (cm.$^{-1}$, KBr): 1650 broad (C=O).

FAB MS (%): 536 (parent, 5.5), 340 (76), 267 (65), 239 (100), 212 (76), 127 (71).

Anal. calc'd for $C_{29}H_{30}N_4O_3FCl\cdot1/3H_2O$: C 64.14, H 5.69, N 10.32. Found: C 64.31, H 5.70, N 9.92.

From isomer A, M.P. 324°–328° C., 28% yield.

$^1$H-NMR (δ, CD$_3$SOCD$_3$): 1.20 (s, 9H), 2.03 (m, 1H), 2.75 (m, 1H), 4.18 (m, 1H), 4.46 (AB$_q$, J$_{AB}$=16, Δν=146), 2H), 5.16 (m, 1H), 6.5–7.7 and 9.17 (m, 15H).

IR (cm.$^{-1}$, KBr): 1650 broad (C=O).

FAB MS (%): 537 (parent, 10), 309 (12), 233 (25), 155 (71), 135 (68), 119 (100), 103 (83).

HRMS calc'd for $C_{29}H_{30}N_4O_3FCl$: 537.2062. Found: 537.2056.

Anal. calc'd for $C_{29}H_{30}N_4O_3FCl\cdot2H_2CO_3$: C 56.32, H 5.18, N 8.48. Found: C 56.87 (+0.55), H 4.98, N 8.86.

EXAMPLE 33

N-tert-butyl-2-[3-(3-(3-methoxyphenyl)ureido)-2-oxo-5-(4-fluorophenyl)-2,3,4,5-tetrahydro-1H-(1)benzazepin-1-yl]ethanoic acid amide Prepared from each of the above isomers in Example 31F:
From isomer B, M.P. 275°–284° C., 60% yield.

$^1$H-NMR (δ, CDCl$_3$, TFA): 1.33 (s, 9H), 2.82 (m, 1H), 3.01 (m, 1H), 3.34 (AB$_q$, J$_{AB}$=16, Δν=150, 2H), 3.87 (s, 3H), 4.26 (m, 1H), 4.61 (m, 1H), 6.8–7.5 (m, 15H).

$^{13}$C-NMR (δ, CDCl$_3$, TFA): 27.6, 36.6, 43.0, 50.5, 53.3, 53.7, 55.6, 115.2, 115.5, 124.7, 127.3, 127.4, 129.4, 129.8, 130.7, 131.0, 136.1, 137.7, 139.1, 157.8, 160.0, 163.2, 169.2, 173.7.

IR (cm.$^{-1}$, KBr): 1650 broad (C=O).

MS (%): 532 (parent, 10), 340 (100), 267 (91), 239 (92), 212 (84).

Anal. calc'd for $C_{30}H_{33}N_4O_4F\cdot1/3H_2O$: C 66.90, H 6.30, N 10.40. Found: C 67.09, H 6.08, N 10.27.

From isomer A, M.P. 317°–320° C., 21% yield.

$^1$H-NMR (δ, CD$_3$SOCD$_3$): 1.20 (s, 9H), 2.16 (m, 1H), 2.91 (m, 1H), 3.66 (s, 3H), 4.22 (m, 1H), 4.47 (AB$_q$, J$_{AB}$=16, Δν=146, 2H), 5.10 (m, 1H), 6.4–6.8, 7.0–7.5, 7.73, and 8.91 (m, 15H).

IR (cm.$^{-1}$, KBr): 1650 broad (C=O).

MS (%): 532 (parent, 5), 340 (68), 267 (77), 239 (86), (66), 188 (44), 149 (100), 123 (72).

HRMS calc'd for $C_{30}H_{34}N_4O_4F$: 533.2556. Found: 533.2518.

Anal. calc'd for $C_{30}H_{33}N_4O_4F\cdot2H_2CO_3$: C 57.14, H 5.54, N 8.33. Found: C 57.47, H 5.25, N 8.89 (+0.56).

EXAMPLE 34

N-tert-butyl-2-[3-(3-(3-tolyl)ureido)-2-oxo-5-(2-fluorophenyl)-2,3,4,5-tetrahydro-1H-(1)benzazepin-1-yl]ethanoic acid amide A. 4-(2-Fluorophenyl)-1,2,3,4-tetrahydronaphth-1-one oxime Prepared as in Example 31 above from the known 4-(2-fluorophenyl)-1,2,3,4-tetrahydronaphth-1-one (see Koptyug, V. A. and Andreeva, T. P., Zh. Organich. Khim., 7, 2398–2403 (1971)) in 90% yield, M.P. 118°–122° C. (from ethyl acetate/hexane).

Anal. calc'd for $C_{16}H_{14}NOF$: C 75.28, H 5.53, N 5.49. Found: C 74.84, H 5.25, N 5.71.

B. 5-(2-Fluorophenyl)-2,3,4,5-tetrahydro-1H-(1)benzazepin-2-one

Prepared from the title compound of Example 34A as in Example 31 above in 43% yield, M.P. 210°–213° C. (from 2-propanol).

Anal. calc'd for $C_{16}H_{14}NOF$: C 75.28, H 5.53, N 5.49. Found: C 75.30, H 5.53, N 5.41.

The remainder of the synthesis was carried out as described in Example 1:

C. 3-Bromo-5-(2-fluorophenyl)-2,3,4,5-tetrahydro-1H-(1)benzazepin-2-one

M.P. 208°–214° C. (from methylene chloride/hexane), 48% yield, mixture of diastereomers.

Anal. calc'd for $C_{16}H_{13}NOFBr$: C 57.51, H 3.92, N 4.19. Found: C 57.60, H 3.66, N 4.35.

D. N-t-Butyl 2-[3-bromo-2-oxo-5-(2-fluorophenyl)-2,3,4,5,-tetrahydro-1H-(1)benzazepin-1-yl]ethanoic acid amide M.P. 85°–90° C. (from isopropyl ether/hexane), 100% yield.

HRMS calc'd for $C_{22}H_{24}BrFN_2O_2$: 446.0999. Found: 446.10136.

E. N-tert-butyl-2-[3-azido-2-oxo-5-(2-fluorophenyl)-2,3,4,5-tetrahydro-1H-(1)benzazepin-1-yl]ethanoic acid amide Mixture of diastereomers, 80% yield.

HRMS calc'd for $C_{22}H_2N_5O_{24}F$: 409.1914. Found: 409.19362.

F. N-tert-butyl-2-[3-amino-2-oxo-5-(2-fluorophenyl)-2,3,4,5-tetrahydro-1H-(1)benzazepin-1-yl]ethanoic acid amide From the mixture of diastereomers, one isomer was isolated by crystallization from ethyl acetate, M.P. 190°–195° C., in 22% yield.

Anal. calc'd for $C_{22}H_{26}N_3O_2F$: C 68.91, H 6.83, N 10.96. Found: C 68.93, H 6.81, N 10.90.

G. N-tert-butyl-2-[3-(3-(3-tolyl)ureido)-2-oxo-5-(2-fluorophenyl)-2,3,4,5-tetrahydro-1H-(1)benzazepin-1-yl]ethanoic acid amide One isomer was obtained from the title compound of example 34F, M.P. 285°–300° C., 79% yield.

$^1$H-NMR (δ, CDCl$_3$,TFA): 1.35 (s, 9H), 2.34 (s, 3H), 2.71 (m, 1H), 3.02 (m, 1H), 3.44 (AB$_q$, J$_{AB}$=17, Δv=230, 2H), 4.48 (m, 1H), 4.62 (m, 1H), 6.8–7.6 (m, 15H).

$^{13}$C-NMR (d, CDCl$_3$): 20.5, 27.6, 37.0, 39.5, 50.8, 53.6, 53.7, 116.1, 116.4, 121.4, 123.7, 124.0, 125.1, 126.2, 127.9, 128.7, 129.1, 129.2, 129.3, 129.5, 129.8, 131.7, 136.1, 138.8, 140.7, 169.2, 173.7.

IR (cm.$^{-1}$, KBr): 1650 broad (C=O).

FAB MS (%): 517 (parent+1, 56), 311 (55), 255 (47), 212 (42), 119 (100).

Anal. calc'd for C$_{30}$H$_{33}$N$_4$O$_3$F: C 70.33, H 6.44, N 10.85. Found: C 70.30, H 6.28, N 10.85.

EXAMPLE 35

N-tert-butyl-2-[3-(3-(3-chlorophenyl)ureido)-2-oxo-5-(2-fluorophenyl)-2,3,4,5-tetrahydro-1H-(1) benzazepin-1-yl]ethanoic acid amide One isomer was obtained, M.P. 270°–283° C. 82% yield.

$^1$H-NMR (δ, CDCl$_3$, TFA): 1.36 (s, 9H), 2.72 (m, 1H), 3.04 (m, 1H), 3.55 (AB$_q$, J$_{AB}$=17, Δv=219, 2H), 4.50 (m, 1H), 4.64 (m, 1H), 6.8–7.6 (m, 15H).

$^{13}$C-NMR (δ, CDCl$_3$,TFA): 27.6, 37.2, 39.6, 50.7, 53.6, 53.8, 116.2, 116.5, 121.2, 123.4, 123.8, 124.0, 126.3, 126.3, 126.8, 128.0, 129.1, 129.2, 129.3, 129.5, 130.6, 131.7, 135.5, 136.2, 138.9, 157.4, 169.3, 174.1.

IR (cm.$^{-1}$, KBr): 1650 broad (C=O).

FAB MS (%): 537 (parent+1, 14), 311 (17), 238 (16), 195 (17), 155 (55), 110 (100).

Anal. calc'd for C$_{29}$H$_{30}$N$_4$O$_3$FCl: C 64.86, H 5.63, N 10.43. Found: C 64.90, H 5.38, N 10.20.

EXAMPLE 36

N-tert-butyl-2-[3-(3-(3-methoxyphenyl)ureido)-2-oxo-5-(2-fluorophenyl)-2,3,4,5-tetrahydro-1H-(1) benzazepin-1-yl]ethanoic acid amide One isomer was obtained from the title compound of Example 34F, mp 265°–280° C., 83% yield.

$^1$H-NMR (δ, CDCl$_3$, TFA): 1.35 (s, 9H), 2.74 (m, 1H), 3.02 (m, 1H), 3.61 (AB$_q$, J$_{AB}$=16, Δv=229, 2H), 3.87 (s, 3H), 4.52 (m, 1H), 4.64 (m, 1H), 6.8–7.5 (m, 15H).

$^{13}$C-NMR (δ, CDCl$_3$): 27.6, 37.0, 39.5, 50.7, 53.5, 53.8, 55.6, 116.4, 122.7, 123.7, 124.0, 126.2, 127.9, 129.1, 129.2, 129.3, 129.5, 130.7, 131.7, 138.8, 157.7, 169.3, 174.0.

IR (cm.$^{-1}$, KBr): 1650 broad (C=O).

MS (%): 533 (parent+1,15), 311 (18), 195 (60), 155 (59), 135 (64), 110 (100), 103 (85).

Anal. calc'd for C$_{30}$H$_{33}$N$_4$O$_4$F•1/4H$_2$O: C 67.09, H 6.29, N 10.43. Found: C 67.12, H 6.02, N 10.42.

EXAMPLE 37

N-tert-butyl-2-[3-(3-(3-tolyl)ureido)-2-oxo-5-(4-chlorophenyl)-2,3,4,5-tetrahydro-1H-(1)benzazepin-1-yl]ethanoic acid amide A. 4-(4-Chlorophenyl)-1,2,3,4-tetrahydronaphth-1-one oxime Prepared as in Example 31 above from the known 4-(4-chlorophenyl)-1,2,3,4-tetrahydronaphth-1-one (see Koptyug, V. A. and Andreeva, T. P., Zh. Organich. Khim., 7, 2398–2403 (1971)) in 79% yield, M.P. 150°–154° C. (from ethyl acetate/hexane).

Anal. calc'd for C$_{16}$H$_{14}$NOCl: C 70.72, H 5.19, N 5.15. Found: C 70.70, H 5.37, N 5.08.

B. 5-(4-Chlorophenyl)-2,3,4,5-tetrahydro-1H-(1) benzazepin-2-one

Prepared from the title compound of Example 37A as in Example 31 above in 31% yield, M.P. 209°–212° C. (from ethyl acetate/hexane).

Anal. calc'd for C$_{16}$H$_{14}$NOCl: C 70.72, H 5.19, N 5.15. Found: C 71.01, H 5.10, N 5.22.

The remainder of the synthesis was carried out as described in Example 1:

C. 3-Bromo-5-(4-chlorophenyl)-2,3,4,5-tetrahydro-1H-(1) benzazepin-2-one

M.P. 194°–198° C. (from methylene chloride/hexane), 20% yield, mixture of diastereomers.

Anal. calc'd for C$_{16}$H$_{13}$NOClBr•H$_2$O: C 52.13, H 4.10, N 3.80. Found: C 52.24, H 4.10 (+0.66), N 3.81.

D. N-t-Butyl 2-[3-bromo-2-oxo-5-(4-chlorophenyl)-2,3,4,5,-tetrahydro-1H-(1)benzazepin-1-yl]ethanoic acid amide M.P. 120°–130° C. (from cyclohexane), 75% yield.

Anal. calc'd for C$_{22}$H$_{24}$N$_2$O$_2$BrCl•2/3H$_2$O: C 55.54, H 5.37, N 5.89. Found: C 55.45, H 4.82 (–0.55), N 5.93.

E. N-tert-butyl-2-[3-azido-2-oxo-5-(4-chlorophenyl)-2,3,4,5-tetrahydro-1H-(1)benzazepin-1-yl]ethanoic acid amide M.P. 158°–168° C., mixture of diastereomers, 75% yield.

Anal. calc'd for C$_{22}$H$_{24}$N$_5$O$_2$Cl•1/3H$_2$O: C 61.18, H 5.76, N 16.21. Found: C 61.03, H 5.59, N 15.81.

F. N-tert-butyl-2-[3-amino-2-oxo-5-(4-chlorophenyl)-2,3,4,5-tetrahydro-1H-(1)benzazepin-1-yl]ethanoic acid amide The mixture of diastereomers was separated into an ethyl acetate insoluble, 13% yield, isomer A and an ethyl acetate soluble foam, 82% yield, isomer B.

Isomer B:

HRMS calc'd for C$_{22}$H$_{26}$N$_3$O$_2$Cl: 399.1708. Found: 399.16959.

G. N-tert-butyl-2-[3-(3-(3-tolyl)ureido)-2-oxo-5-(4-chlorophenyl)-2,3,4,5-tetrahydro-1H-(1)benzazepin-1-yl] ethanoic acid amide One isomer was obtained from isomer B above, M.P. 303°–310° C, 88% yield.

$^1$H-NMR (δ, CDCl$_3$): 1.33 (s, 9H), 2.33 (s, 3H), 2.89 (m, 1H), 3.00 (m, 1H), 3.35 (AB$_q$, J$_{AB}$=16, Δv=159, 2H), 4.23 (m, 1H), 4.59 (m, 1H), 6.8–7.6 (m, 15H).

$^{13}$C-NMR (δ, CDCl$_3$): 20.5, 27.7, 36.6, 43.1, 50.5, 53.5, 121.4, 124.7, 125.2, 129.1, 128.7, 129.0, 129.4, 129.8, 129.9, 131.0, 133.1, 137.3, 139.0, 139.2, 140.7, 158.1, 169.0, 173.5.

IR (cm.$^{-1}$, KBr): 1650 broad (C=O).

FAB MS (%): 356 (56), 261 (67), 188 (70), 133 (100), 57 (77), 28 (96).

Anal. calc'd for C$_{30}$H$_{33}$N$_4$O$_3$Cl: C 67.60, H 6.24, N 10.51. Found: C 67.68, H 6.19, N 10.41.

EXAMPLE 38

N-tert-butyl-2-[3-(3-(3-chlorophenyl)ureido)-2-oxo-5-(4-chlorophenyl)-2,3,4,5-tetra-hydro-1H-(1) benzazepin-1-yl]ethanoic acid amide One isomer was obtained from isomer B in Example 37F, M.P. 304°–307° C., 36% yield.

$^1$H-NMR (δ, CDCl$_3$, TFA): 1.32 (s, 9H), 2.87 (m, 1H), 3.02 (m, 1H), 3.41 (AB$_q$, J$_{AB}$=16, Δv=151, 2H), 4.23 (m, 1H), 4.58 (m, 1H), 6.8–7.6 (m, 15H).

$^{13}$C-NMR (δ, CDCl$_3$, TFA): 27.8, 43.1, 50.4, 53.5, 124.7, 127.2, 128.7, 129.0, 129.4,129.9, 130.7, remaining carbons not visible in this scan.

IR (cm.$^{-1}$, KBr): 1650 broad (C=O).

FAB MS (%): 356 (48), 261 (43), 188 (44), 153 (100), 125 (45), 90 (52), 57 (63), 28 (47).

Anal. calc'd for $C_{29}H_{30}N_4O_3Cl_2 \cdot 1/2H_2O$: C 61.92, H 5.55, N 9.96. Found: C 61.95, H 5.31, N 9.90.

EXAMPLE 39

N-tert-butyl-2-[3-(3-(3-methoxyphenyl)ureido)-2-oxo-5-(4-chlorophenyl)-2,3,4,5-tetrahydro-1H-(1)benzazepin-1-yl]ethanoic acid amide One isomer was obtained from isomer B in Example 37F, M.P. 303°–307° C., 65% yield.

$^1$H-NMR (δ, CDCl$_3$,TFA): 1.32 (s, 9H), 2.85 (m, 1H), 3.00 (m, 1H), 3.35 (AB$_q$, J$_{AB}$=16, Δv=161, 2H), 3.85 (s, 3H), 4.20 (m, 1H), 4.55 (m, 1H), 6.8–7.5 (m, 15H).

$^{13}$C-NMR (δ, CDCl$_3$): 27.7, 36.6, 41.3, 43.1, 50.5, 53.4, 55.6, 122.7, 124.7, 127.1, 128.7, 129.0, 129.4, 129.9, 130.7, 131.0, 133.1, 137.4, 139.0, 139.2, 169.1, 173.9, 174.1.

IR (cm.$^{-1}$, KBr): 1650 broad (C=O).

MS (%): 548 (parent-1,2), 356 (32), 283 (37), 255 (34), 23 (100).

Anal. calc'd for $C_{30}H_{33}N_4O_4Cl \cdot 1/3H_2O$: C 64.92, H 6.14, N 10.04. Found: C 65.19, H 5.93, N 9.99.

EXAMPLE 40

N-tert-butyl-2-[3-(3-(3-tolyl)ureido)-2-oxo-5-(4-methylphenyl)-2,3,4,5-tetrahydro-1H-(1)benzazepin-1-yl]ethanoic acid amide A. 4-[4-Methylphenyl)-1,2,3,4-tetrahydronaphth-1-one oxime Prepared as in Example 31 above from the title compound of Example 40A from the known 4-(4-methylphenyl)-1,2,3,4-tetrahydronaphth-1-one (see Koptyug, V. A. and Andreeva, T. P., Zh. Organich. Khim., 7, 2398–2403 (1971)) in 94% yield, M.P. 97°–101° C. (from ethyl acetate/hexane).

Anal. calc'd for $C_{17}H_{17}NO$: C 81.24, H 6.82, N 5.57. Found: C 81.03, H 6.63, N 5.57.

B. 5-[4-Methylphenyl)-2,3,4,5-tetrahydro-1H-(1)benzazepin-2-one

Prepared from the title compound of Example 40A as in Example 31 above in 41% yield, M.P. 178°–181° C. (from ethyl acetate/hexane).

Anal. calc'd for $C_{17}H_{17}NO$: C 81.24, H 6.82, N 5.57. Found: C 80.80 (–0.44), H 6.63, N 5.51.

The remainder of the synthesis was carried out as described in Example 1:

C. 3-Bromo-5-(4-methylphenyl)-2,3,4,5-tetrahydro-1H-(1)benzazepin-2-one

M.P. 168°–176° C., 68% yield, mixture of diastereomers.

D. N-t-Butyl 2-[3-bromo-2-oxo-5-(4-methylphenyl)-2,3,4,5,-tetrahydro-1H-(1)benzazepin-1-yl]ethanoic acid amide M.P. 128°–138° C. (from hexane), 56% yield.

Anal. calc'd for $C_{23}H_{27}N_2O_2Br$: C 62.31, H 6.14, N 6.32. Found: C 62.49, H 6.21, N 6.28.

E. N-tert-butyl-2-[3-azido-2-oxo-5-[4-methylphenyl)-2,3,4,5-tetrahydro-1H-(1)benzazepin-1-yl]ethanoic acid amide M.P. 55°–65° C., mixture of diastereomers, 75% yield.

Anal. calc'd for $C_{23}H_{27}N_5O_2 \cdot 1/3H_2O$: C 67.13, H 6.78, N 17.02. Found: C 67.09, H 6.67, N 16.81.

F. N-tert-butyl-2-[3-amino-2-oxo-5-(4-methylphenyl)-2,3,4,5-tetrahydro-1H-(1)benzazepin-1-yl]ethanoic acid amide The mixture of diastereomers was separated into an ethyl acetate insoluble, mp 292°–295° C., 5.4% yield, isomer A and an isopropyl ether insoluble, M.P. 150°–170° C., 12% yield, Isomer B.

Isomer A:
HRMS calc'd for $C_{23}H_{29}N_3O_2$: 379.2253. Found: 379.22664
Isomer B:
HRMS calc'd for $C_{23}H_{29}N_3O_2$: 379.2253. Found: 379.22455.

G. N-tert-butyl-2-[3-(3-(3-tolyl)ureido)-2-oxo-5-(4-methylphenyl)-2,3,4,5-tetrahydro-1H-(1)benzazepin-1-yl]ethanoic acid amide Prepared from each of the above isomers of Example 40F: From isomer B, M.P. 230°–238° C., 29% yield.

$^1$H-NMR (δ, CDCl$_3$): 1.27 (s, 9H), 2.21 (s, 3H), 2.80 (m, 1H), 3.00 (m, 1H), 3.21 (AB$_q$, J$_{AB}$=16, Δv=296, 2H), 4.22 (m, 1H), 4.58 (m, 1H), 6.07 (bs, 1H), 6.30 (bs, 1H), 6.8–7.4 (m, 12H), 7.64 (bs, 1H).

$^{13}$C-NMR (δ, CDCl$_3$): 21.4, 28.5, 37.1, 44.3, 50.1, 51.6, 53.7, 116.6, 123.2, 123.5, 127.1, 127.7, 128.6, 128.8, 128.9, 129.0, 137.9, 138.2, 138.7, 139.0, 141.1, 155.4, 167.9, 173.0.

IR (cm.$^{-1}$, KBr): 1650 broad (C=O).

FAB MS (%): 513 (parent+1, 82), 440 (92), 234 9100), 208 (96), 119 (85).

HRMS calc'd for $C_{31}H_{36}N_4O_3$: 512.27514. Found: 512.27474.

From isomer A, M.P. 298°–305° C., 68% yield.

$^1$H-NMR (δ, CD$_3$SOCD$_3$): 1.22 (s, 9H), 2.03 (m, 1H), 2.21 (s, 3H), 2.31 (s, 3H), 2.82 (m, 1H), 4.45 (AB$_q$, J$_{AB}$=16, Δv=135, 2H), 4.24 (m, 1H), 4.99 (m, 1H), 6.5–7.3 (m, 13H), 7.66 (bs, 1H), 8.67 (bs, 1H).

$^{13}$C-NMR (δ, CD$_3$SOCD$_3$): 21.2, 28.5, 41.2, 49.6, 50.3, 51.1, 114.7, 118.1, 122.0, 123.0, 125.9, 126.4, 126.5, 127.0, 127.6, 128.4, 128.5, 129.4, 137.6, 137.8, 139.0, 140.1, 140.5, 154.4, 167.0, 171.1.

IR (cm.$^{-1}$, KBr): 1650 broad (C=O).

FAB MS (%): 513 (parent+1, 10), 380 (100), 307 (56), 155 (46), 119 (98).

Anal. calc'd for $C_{31}H_{36}N_4O_3 \cdot 5/4H_2O$: C 69.57, H 7.25, N 10.47. Found: C 69.55, H 7.05, N 10.42.

EXAMPLE 41

N-tert-butyl-2-[3-(3-(3-chlorophenyl)ureido)-2-oxo-5-(4-methylphenyl)-2,3,4,5-tetrahydro-1H-(1)benzazepin-1-yl]ethanoic acid amide Prepared from each of the above isomers in Example 40F: From isomer B, M.P. 235°–238° C., 65% yield.

$^1$H-NMR (δ, CDCl$_3$): 1.30 (s, 9H), 2.21 (s, 3H), 3.0 (m, 2H), 3.36 (AB$_q$, J$_{AB}$=16, Δv=291, 2H), 4.30 (m, 1H), 4.64 (m, 1H), 6.7–7.5 (m, 13H), 7.57 (bs, 1H), 8.06 (bs, 1H).

$^{13}$C-NMR (δ, CDCl$_3$): 21.5, 28.7, 36.8, 44.5, 50.5, 51.9, 53.2, 116.9, 119.0, 122.1, 123.4, 124.2, 126.1, 127.1, 127.2, 127.3, 127.8, 128.1, 128.2, 129.0, 129.5, 130.9, 137.9, 138.3, 140.7, 141.1, 141.6, 155.2, 167.4, 173.3.

IR (cm.$^{-1}$, KBr): 1650 broad (C=O).

FAB MS (%): 533 (parent+1, 35), 460 (67), 262 (37), 234 (100), 208 (85), 105 (36).

Anal. calc'd for $C_{30}H_{33}N_4O_3Cl$: C 67.60, H 6.24, N 10.51. Found: C 67.50, H 6.59, N 10.34.

From isomer A, M.P. 253°–263° C., 68% yield.

$^1$H-NMR (δ, CD$_3$SOCD$_3$): 1.21 (s, 9H), 2.03 (m, 1H), 2.31 (s, 3H), 2.75 (m, 1H), 4.20 (m, 1H), 4.44 (AB$_q$, J$_{AB}$=16, Δv=116), 2H), 4.96 (m, 1H), 6.5–7.3 (m, 13H), 7.59 (bs, 1H), 8.17 (bs, 1H).

$^{13}$C-NMR (δ, CD$_3$SOCD$_3$): 21.2, 28.4, 106.9, 115.5, 115.6, 120.7, 122.9, 125.8, 126.4, 127.0, 127.1, 128.3, 129.4, 129.9, 133.3, 137.5, 139.2, 140.3, 140.4, remaining carbons not visible in this scan.

IR (cm.$^{-1}$, KBr): 1650 broad (C=O).

FAB MS (%): 533 (parent+1, 12), 335 (15), 234 920), 169 (67), 155 (33), 135 940), 119 (100), 103 (57).

HRMS calc'd for $C_{29}H_{30}N_4O_3FCl$: 532.2319. Found: 532.2312.

EXAMPLE 42

N-tert-butyl-2-[3-(3-(3-methoxyphenyl)ureido)-2-oxo-5-(4-methylphenyl)-2,3,4,5-tetrahydro-1H-(1) benzazepin-1-yl]ethanoic acid amide Prepared from isomer B from Example 40F, M.P. 233°–236° C., 60% yield.

$^1$H-NMR (δ, CDCl$_3$,TFA): 1.27 (s, 9H), 2.20 (s, 3H), 2.85 (m, 1H), 3.10 (m, 1H), 3.28 (AB$_q$, J$_{AB}$=16, Δν=294, 2H), 3.68 (s, 3H), 4.24 (m, 1H), 4.65 (m, 1H), 6.8–7.5 (m, 14H), 7.82 (bs, 1H).

$^{13}$C-NMR (δ, CDCl$_3$): 21.5, 28.6, 37.3, 44.4, 50.2, 51.7, 53.6, 55.1, 104.9, 108.8, 111.6, 123.3, 124.7, 126.1, 127.1, 127.2, 127.7, 127.8, 128.2, 128.9, 129.0, 129.4, 130.8, 137.9, 138.3, 140.6, 141.2, 155.2, 160.2, 167.5, 173.0.

IR (cm.$^{-1}$, KBr): 1650 broad (C=O).

FAB MS (%): 529 (parent+1,50), 456 (68), 307 (50), 262 (50), 234 9100), 208 (92).

Anal. calc'd for $C_{31}H_{36}N_4O_4$: C 70.43, H 6.86, N 10.60. Found: C 70.23, H 7.22, N 10.36.

EXAMPLE 43

N-tert-butyl-2-[3-(3-(3-ethylphenyl)ureido)-2-oxo-5-(4-methylphenyl)-2,3,4,5-tetrahydro-1H-(1) benzazepin-1-yl]ethanoic acid amide Prepared from isomer B from Example 40F, M.P. 210°–214° C., 55% yield $^1$H-NMR (δ, CDCl$_3$): 114 (t, J=7, 3H), 1.26 (s, 9H), 2.20 (s, 3H), 2.52 (q, J=7, 2H), 2.85 (m, 1H), 3.07 (m, 1H), 3.31 (AB$_q$, J$_{AB}$=16, Δν=293, 2H), 4.23 (m, 1H), 4.64 (m, 1H), 5.90 (bs, 1H), 6.54 (bs, 1H), 6.8–7.4 (m, 12H), 7.76 (bs, 1H).

$^{13}$C-NMR (δ, CDCl$_3$): 16.0, 20.9, 21.5, 28.6, 37.2, 44.4, 50.3, 51.6, 53.6, 117.0, 119.4, 122.3, 123.3, 124.6, 126.2, 127.2, 127.7, 128.2, 128.7, 129.0, 130.8, 137.9, 138.3, 139.2, 141.2, 141.8, 145.2, 155.4, 167.6, 173.0.

IR (cm.$^{-1}$, KBr): 1650 broad (C=O)

FAB MS (%): 527 (parent+1, 40), 454 (47), 380 (45), 307 (60), 262 (53), 234 (100), 208 (60).

Anal. calc'd for $C_{32}H_{38}N_4O_3$: C 72.98, H 7.27, N 10.64. Found: C 72.97, H 7.74 (+0.47), N 10.39.

HRMS calc'd for $C_{32}H_{38}N_4O_3$: 526.2877. Found: 526.28695.

EXAMPLE 44

N-tert-butyl-2-[3-(3-(3-tolyl)ureido)-2-oxo-5-(3,4-dichlorophenyl)-2,3,4,5-tetrahydro-1H-(1) benzazepin-1-yl]ethanoic acid amide A. 4-(3,4-Dichlorophenyl)-1,2,3,4-tetrahydronaphth-1-one oxime Prepared as in Example 31A above from the known 4-(3,4-dichlorophenyl)-1,2,3,4-tetrahydronaphth-1-one (see Quallich, G. J., Williams, M. T., Friedmann, R. C. J. Org. Chem., 55, 4971–4973 (1991)) in 70% yield, M.P. 159°–162° C. (from methylene chloride/cyclohexane).

Anal. calc'd for $C_{16}H_{13}NOCl_2$: C 62.76, H 4.28, N 4.57. Found: C 62.41, H 4.04, N 4.44.

B. 5-(3,4-Dichlorophenyl)-2,3,4,5-tetrahydro-1H-(1) benzazepin-2-one

Prepared from the title compound of Example 44A as in Example 31B above in 89% yield, M.P. 191°–194° C.

Anal. calc'd for $C_{16}H_{13}NOCl_2$: C 62.76, H 4.28, N 4.57. Found: C 62.56, H 4.14, N 4.59.

The remainder of the synthesis was carried out as described in Example 1:

C. 3-Bromo-5-(3,4-dichlorophenyl)-2,3,4,5-tetrahydro-1H-(1)benzazepin-2-one

M.P. 183°–188° C. (from ethyl acetate/hexane), 73% yield, mixture of diastereomers.

HRMS calc'd for $C_{16}H_{12}NOBrCl_2$: 382.9477. Found: 382.9480.

D. N-t-Butyl 2-[3-bromo-2-oxo-5-(3,4-dichlorophenyl)-2,3,4,5,-tetrahydro-1H-(1)benzazepin-1-yl]ethanoic acid amide M.P. 85–95, 92% yield.

HRMS calc'd for $C_{22}H_{23}N_2O_2BrCl_2$: 496.0315. Found: 496.03341.

E. N-tert-butyl-2-[3-azido-2-oxo-5-(3,4-dichlorophenyl)-2,3,4,5-tetrahydro-1H-(1)benzazepin-1-yl]ethanoic acid amide M.P. 79°–99° C., mixture of diastereomers, 91% yield.

HRMS calc'd for $C_{22}H_{23}N_5O_2Cl_2$: 459.1225. Found: 459.12421.

F. N-tert-butyl-2-[3-amino-2-oxo-5-(3,4-dichlorophenyl)-2,3,4,5-tetrahydro-1H-(1)benzazepin-1-yl]ethanoic acid amide Prepared by reduction with triphenylphosphine in aqueous tetrahydrofuran as a mixture of diastereomers, which was separated into an isopropyl ether insoluble, M.P. 185°–190° C., 31% yield, isomer A and a chloroform insoluble, M.P. 140°–150° C., 1.5% yield, isomer B. Isomer A:

Anal. calc'd for $C_{22}H_{25}N_3O_2Cl_2$: C 60.83, H 5.80, N 9.67. Found: C 60.91, H 5.71, N 9.46.

G. N-tert-butyl-2-(3-(3-(3-tolyl)ureido)-2-oxo-5-(3,4-dichlorophenyl)-2,3,4,5-tetrahydro-1H-(1)benzazepin-1-yl] ethanoic acid amide Prepared from each of the above isomers from Example 44F:

From isomer B, M.P. 299°–301° C., 58% yield.

$^1$H-NMR (δ, CD$_3$SOCD$_3$): 1.23 (s, 9H), 2.21 (s, 3H), 2.92 (m, 1H), 3.4 (m, 1H), 3.42 (AB$_q$, J$_{AB}$=16, Δν=229, 2H), 4.35 (m, 1H), 4.58 (m, 1H), 6.6–7.6 (m, 14H), 8.75 (bs, 1H).

$^{13}$C-NMR (δ, CDCl$_3$): 21.2, 28.5, 42.8, 48.7, 50.3, 51.9, 60.3, 72.3, 114.8, 118.2, 122.0, 124.4, 126.9, 127.2, 128.4, 128.5, 128.6, 129.1, 130.2, 130.8, 136.6, 137.8, 140.1, 141.7, 144.0, 154.1, 166.8, 170.3.

IR (cm.$^{-1}$, KBr): 1650 broad (C=O).

FAB MS (%): 566/568 (parent, Cl$^{35}$Cl$^{37}$, 4/2) 390 (25), 289/291 (42/40), 261 (50), 188 (60), 133 (100), 57 (65).

HRMS calc'd for $C_{30}H_{32}N_4O_3Cl_2$: 566. 1845. Found: 566.1861.

From isomer A, M.P. 331°–334° C., 90% yield.

$^1$H-NMR (δ, CD$_3$SOCD$_3$): 1.20 (s, 9H), 2.10 (m, 1H), 2.20 (s, 3H), 2.82 (m, 2H), 4.12 (m, 1H), 4.46 (AB$_q$, J$_{AB}$=16, Δν=150, 2H), 5.04 (m, 1H), 6.5–6.7 and 7.0–7.8 (m, 14H), 8.68 (bs, 1H).

IR (cm.$^{-1}$, KBr): 1650 broad (C=O)

FAB MS (%): 567 (parent, 1), 309 (6), 233 (17), 157 (100), 135 (23), 119 (58), 103 (28).

Anal. calc'd for $C_{30}H_{32}N_4O_3Cl_2$: C 63.49, H 5.68, N 9.87. Found: C 63.82, H 5.60, N 9.60.

EXAMPLE 45

N-tert-butyl-2-[3-(3-(3-chlorophenyl)ureido)-2-oxo-5-(3,4-dichlorophenyl)-2,3,-4,5-tetrahydro-1H-(1) benzazepin-1-yl]ethanoic acid amide Prepared from isomer A in Example 44F, M.P. 329°–332° C., 86% yield.

¹H-NMR (δ, CD₃SOCD₃): 1.20 (s, 9H), 2.08 (m, 1H), 2.80 (m, 1H), 4.20 (m, 1H), 4.47 (AB_q, J_AB=16, Δν=147), 2H), 5.10 (m, 1H), 6.5–7.8 (m, 14H), 8.99 (bs, 1H).

¹³C-NMR (δ, CD₃SOCD₃): 28.9, 49.9, 50.8, 51.4, 56.1, 60.7, 72.7, 85.2, 116.4, 117.4, 121.3, 123.7, 127.18, 122.22, 128.0, 129.6, 130.1, 130.7, 131.18, 131.22, 133.6, 138.5, 140.7, 142.1, 142.3, 154.6, 167.5, 171.3.

IR (cm.⁻¹, KBr): 1650 broad (C=O).

FAB MS (%): 385 (35), 233 (18), 155 (56), 135 (35), 119 (100), 103 (44).

Anal. calc'd for C₂₉H₂₉N₄O₃Cl₃: C 59.24, H 4.97, N 9.53. Found: C 59.52, H 4.92, N 9.23.

EXAMPLE 46

N-tert-butyl-2-[3-(3-(3-methoxyphenyl)ureido)-2-oxo-5-(3,4-dichlorophenyl)-2,3,4,5-tetrahydro-1H-(1)benzazepin-1-yl]ethanoic acid amide Prepared from isomer A in Example 44F, M.P. 324°–327° C., 92% yield.

¹H-NMR (δ, CD₃SOCD₃): 1.20 (s, 9H), 2.08 (m, 1H), 2.83 (m, 1H), 3.67 (s, 3H), 4.22 (m, 1H), 4.47 (AB_q, J_AB=16, Δν=149, 2H), 5.14 (m, 1H), 6.4–7.7 (m, 14H), 8.77 (bs, 1H).

¹³C-NMR (δ, CD₃SOCD₃): 28.9, 49.8, 50.8, 51.4, 55.3, 60.7, 72.7, 103.7, 107.3, 110.3, 123.6, 123.7, 127.1, 127.2, 128.0, 129.6, 129.9, 130.0, 131.1, 131.2, 131.7, 138.6, 40.8, 141.8, 142.4, 154.7, 160.1, 167.5, 171.4.

IR (cm.⁻¹, KBr): 1650 broad (C=O)

MS (%): 583 (parent, 1), 456 921), 293 925), 279 (27), 233 939), 157 (100), 156 (94), 154 (53), 135 (60), 119 (100), 103 (90).

Anal. calc'd for C₃₀H₃₂N₄O₄Cl₂: C 61.75, H 5.53, N 9.60. Found: C 61.81, H 5.35, N 9.37.

EXAMPLE 47

N-tert-butyl-2-[3-(3-(3-tolyl)ureido)-2-oxo-5-phenyl-8-methyl-2,3,4,5-tetrahydro-1H-(1)benzazepin-1-yl]ethanoic acid amide A. 8-Methyl-1-naphthol Prepared from the known (J. Chem. Soc., C, (1966) 523) 8-hydroxymethyl-1-naphthol by hydrogenolysis using 0.1 equiv. of 20% palladium hydroxide on carbon (Pearlmann's catalyst) in ethanol at 45 psi hydrogen for 4 hours in quantitative yield, M.P. 56°–59° C.

B. 4-Phenyl-7-methyl-1,2,3,4-tetrahydronaphth-1-one and 4-phenyl-8-methyl-1,2,3,4-tetrahydronaphth-1-one Prepared from 8-methyl-1-naphthol using the procedure described above in Example 31 from Koptyug, V. A. and Andreeva, T. P., Zh. Organich. Khim., 7, 2398–2403 (1971) The products were separated by chromatography on silica gel using hexane/ethyl acetate as eluant and crystallized separately from methanol. X-ray analysis of single crystals of both compounds, grown in methanol, established the structures of the two isomers.

7-Methyl isomer, M.P. 72°–74° C.

¹H-NMR (δ, CDCl₃): 2.2–2.8 (m, 4H), 2.36 (s, 3H), 4.25 (m, 1H), 6.8–7.4 and 7.90 (m, 8H).

¹³C-NMR (δ, CDCl₃): 21.0, 32.0, 36.8, 45.0, 126.7, 126.9, 127.2, 128.4, 128.6, 129.5, 132.6, 134.6, 143.5, 143.9, 198.4.

IR (cm.⁻¹, KBr): 1681 (C=O).

MS (%): 236 (parent, 100), 194 (70), 165 (50).

Anal. calc'd for C₁₇H₁₆O: C 86.40, H 6.82. Found: C 86.39, H 6.76.

8-Methyl isomer, M.P. 60°–63° C.

¹H-NMR (δ, CDCl₃): 2.2–2.7 (m, 4H), 2.68 (s, 3H), 4.28 (m, 1H), 6.8–7.3 (m, 8H).

¹³C-NMR (δ, CDCl₃): 23.4, 31.2, 38.1, 46.1, 126.6, 126.8, 127.8, 128.6, 131.0, 131.6, 132.4, 141.2, 144.1, 147.3, 200.0.

IR (cm.⁻¹, KBr): 1680 (C=O).

MS (%): 236 (parent, 100), 208 (85), 165 (50). Anal. calc'd for C₁₇H₁₆O: C 86.40, H 6.82. Found: C 86.77, H 6.66.

Preparation of 5-phenyl-8-methyl-2,3,4,5-tetrahydro-1H-(1)benzazepin-2-one:

C. 4-Phenyl-7-methyl-1,2,3,4-tetrahydronaphth-1-one oxime

Prepared from 4-phenyl-7-methyl-1,2,3,4-tetrahydroaphth-1-one.

M.P. 143°–146° C., yield 72%.

Anal. calc'd for C₁₇H₁₇NO: C 81.24, H 6.82, N 5.57. Found: C 81.11, H 7.02, N 5.51.

D. 5-phenyl-8-methyl-2,3,4,5-tetrahydro-1H-(1)benzazepin-2-one

M.P. 230°–234° C., yield 28.5%.

Anal. calc'd for C₁₇H₁₇NO: C 81.24, H 6.82, N 5.57. Found: C 81.25, H 6.89, N 5.54.

The remainder of the synthesis was carried out as described in Example 1:

E. 3-Bromo-5-phenyl-8-methyl-2,3,4,5-tetrahydro-1H-(1)benzazepin-2-one

M.P. 228°–232° C., 46% yield.

Anal. calc'd for C₁₇H₁₆NOBr·1/4H₂O: C 61.00, H 4.97, N 4.18. Found: C 61.07, H 5.01, N 4.38.

F. N-t-Butyl 2-[3-bromo-2-oxo-5-phenyl-8-methyl-2,3,4,5,-tetrahydro-1H-(1)benzazepin-1-yl]ethanoic acid amide M.P. 227°–230° C., 36% yield.

HRMS calc'd for C₂₃H₂₇N₂O₂Br: 442.1249. Found: 442.12321.

G. N-tert-butyl-2-[3-azido-2-oxo-5-phenyl-8-methyl-2,3,4,5-tetrahydro-1H-(1)benzazepin-1-yl]ethanoic acid amide M.P. 112°–115° C., 56% yield as a single diasteromer.

Anal. calc'd for C₂₃H₂₇N₅O₂: C 68.13, H 6.71, N 17.27. Found: C 68.40, H 6.82, N 17.12.

H. N-tert-butyl-2-[3-amino-2-oxo-5-phenyl-8-methyl-2,3,4,5-tetrahydro-1H-(1)benzazepin-1-yl]ethanoic acid amide:

Prepared as a single diastersomer corresponding to isomer B of Example 44F. M.P. 170°–180° C., 75% yield.

HRMS calc'd for C₂₃H₂₉N₃O₂: 379.2253. Found: 379.2267.

I. N-tert-butyl-2-[3-(3-(3-tolyl)ureido)-2-oxo-5-phenyl-8-methyl-2,3,4,5-tetrahydro-1H-(1)benzazepin-1-yl]ethanoic acid amide M.P. 232°–238° C., 72% yield.

¹H-NMR (δ, CDCl₃): 1.26 (s, 9H), 2.21 (s, 3H), 2.30 (s, 3H), 2.64 (m, 1H), 2.92 (m, 1H), 3.12 (AB_q, J_AB=16, Δν=283, 2H), 4.15 (m, 1H), 4.50 (m, 1H), 6.10 (bs, 1H), 6.2–7.2 (m, 14H).

¹³C-NMR (δ, CDCl₃): 21.0, 21.4, 28.5, 36.8, 43.8, 49.9, 51.5, 53.6, 116.3, 120.0, 123.4, 125.2, 126.2, 126.3, 128.2, 128.3, 128.6, 130.5, 135.1, 138.6, 139.0, 140.8, 141.9, 155.4, 168.0, 173.0.

IR (cm.⁻¹, KBr): 1640 broad (C=O).

FAB MS (%): 512 (parent, 77), 440 (100), 307 (72), 208 (68).

Anal. calc'd for C₃₁H₃₆N₄O₃: C 72.63, H 7.08, N 10.93. Found: C 72.29, H 6.85, N 10.78.

EXAMPLE 48

N-tert-butyl-2-[3-(3-(3-chlorophenyl)ureido)-2-oxo-5-phenyl-8-methyl-2,3,4,5-tetrahydro-1H-(1)benzazepin-1-yl]ethanoic acid amide Prepared from Example 47H, M.P. 155°–165° C., 68% yield.

¹H-NMR (δ, CDCl₃): 1.29 (s, 9H), 2.33 (s, 3H), 2.8–3.0 (m, 2H), 3.32 (AB$_q$, J$_{AB}$=16, Δv=285, 2H), 4.20 (m, 1H), 4.56 (m, 1H), 6.6–7.3 (m, 13H), 7.56 (bs, 1H), 8.00 (bs, 1H).

¹³C-NMR (δ, CDCl₃): 21.1, 28.7, 36.8, 44.0, 50.5, 51.9, 53.1, 60.4, 116.9, 118.9, 122.0, 124.8, 126.3, 126.4, 126.5, 128.3, 128.4, 129.5, 130.7, 134.2, 135.0, 139.1, 140.7, 40.8, 142.0, 155.2, 167.4, 173.4.

IR (cm.⁻¹, KBr): 1640 broad (C=O).

FAB MS (%): 533/535 (parent+1, Cl³⁵/Cl³⁷, 69/26), 460 (100), 307 (52), 234 (60), 208 (70).

Anal. calc'd for C₃₀H₃₃N₄O₃Cl: C 67.60, H 6.24, N 10.51. Found: C 67.27, H 6.06, N 10.23.

EXAMPLE 49

5-Phenyl-9-methyl-2,3,4,5-tetrahydro-1H-(1)benzazepin-2-one

Prepared as in Example 31 from 4-phenyl-8-methyl-1,2,3,4-tetrahydronaphth-1-one.

A. 4-Phenyl-8-methyl-1,2,3,4-tetrahydronaphth-1-one oxime

M.P. 130°–136° C., 73% yield.

Anal. calc'd for C₁₇H₁₇NO: C 81.24, H 6.82, N 5.57 Found: C 81.19, H 6.61, N 5.51.

B. 5-phenyl-9-methyl-2,3,4,5-tetrahydro-1H-(1)benzazepin-2-one

M.P. 154°–157° C., 81% yield.

Anal. calc'd for C₁₇H₁₇NO: C 81.24, H 6.82, N 5.57. Found: C 81.09, H 6.52, N 5.45.

The remainder of the synthesis was carried out as described in Example 1.

C. 3-Bromo-5-phenyl-9-methyl-2,3,4,5-tetrahydro-1H-(1)benzazepin-2-one

As a mixture of diastereomers, one of which had M.P. 240°243° C., 44% yield.

Anal. calc'd for C₁₇H₁₆NOBr: C 61.83, H 4.88, N 4.24. Found: C 61.79, H 4.57, N 4.09.

The remaining material, 26% yield, was obtained as a mixture of diastereomers, and was combined with the above diastereomer in the next step.

D. N-t-Butyl 2-[3-bromo-2-oxo-5-phenyl-9-methyl-2,3,4,5,-tetrahydro-1H-(1)benzazepin-1-yl]ethanoic acid amide The diastereomers were separated by chromatography on silica gel using hexane/ethyl acetate as eluant, then crystallized from methylene chloride/hexane:

Isomer A, M.P. 199°–202° C., 15% yield.

Anal. calc'd for C₂₃H₂₇N₂O₂Br: C 62.31, H 6.14, N 6.32. Found: C 62.60, H 5.87, N 6.12.

Isomer B, M.P. 227°–230° C., 63% yield.

Anal. calc'd for C₂₃H₂₇O₂Br: C 62.31, H 6.14, N 6.32. Found: C 62.83 (+0.52), H 6.48, N 6.22.

E. N-tert-butyl-2-[3-azido-2-oxo-5-phenyl-9-methyl-2,3,4,5-tetrahydro-1H-(1)-benzazepin-1-yl]ethanoic acid amide Obtained as a mixture of diastereomers, which were separated by chromatography on silica gel using hexane/ethyl acetate as eluant.

Isomer A, oil, 18% yield.

HRMS calc'd for C₂₃H₂₇N₅O₂: 405.2159. Found: 405.21724.

Isomer B, M.P. 160°–164° C., 76% yield.

Anal. calc'd for C₂₃H₂₇N₅O₂: C 68.13, H 6.71, N 17.27. Found: C 68.09, H 6.71, N 17.08.

F. N-tert-butyl-2-[3-amino-2-oxo-5-phenyl-9-methyl-2,3,4,5-tetrahydro-1H-(1)-benzazepin-1-yl]ethanoic acid amide Each isomer from Example 49E was hydrogenated separately.

Isomer A, oil.

HRMS calc'd for C₂₃H₂₇N₅O₂: 380.2331. Found: 380.23462. Isomer B, oil, 13% yield.

HRMS calc'd for C₂₃H₂₇N₅O₂: 380.2331. Found: 380.23276.

G. N-tert-butyl-2-[3-(3-(3-tolyl)ureido)-2-oxo-5-phenyl-9-methyl-2,3,4,5-tetrahydro-1H-(1)benzazepin-1-yl]ethanoic acid amide Prepared from isomer A above, M.P. 221°–223 ° C., 84% yield.

¹H-NMR (δ, CDCl₃): 1.21 (s, 9H), 2.24 (s, 3H), 2.28 (s, 3H), 2.74 (AB$_q$, J$_{AB}$=16, Δv=135, 2H), 2.82 (m, 1H), 2.95 (m, 1H), 4.14 (m, 1H), 4.51 (m, 1H), 6.54 (bs, 1H), 6.8–7.3 (m, 13H), 7.78 (bs, 1H).

¹³C-NMR (δ, CDCl₃): 18.8, 21.5, 28.5, 35.8, 44.6, 50.0, 51.2, 53.5, 55.2, 116.9, 120.6, 123.7, 126.3, 126.7, 128.4, 128.7, 128.8, 131.6, 135.8, 138.8, 139.1, 139.3, 139.9, 141.3, 155.4, 168.0, 174.7.

IR (cm.⁻¹, KBr): 1640 broad (C=O).

FAB MS (%): 513 (parent+1, 27), 440 (100), 251 (37), 234 (65), 208 (50).

Anal. Calc'd for C₃₁H₃₆N₄O₃: C 72.63, H 7.08, N 10.93. Found: C 72.89, H 7.02, N 10.90.

EXAMPLE 50

N-tert-butyl-2-[3-(3-(3-methoxyphenyl)ureido)-2-oxo-5-phenyl-9-methyl-2,3,4,5-tetrahydro-1H-(1)benzazepin-1-yl]ethanoic acid amide Prepared from isomer A in Example 49F, M.P. 162°–167° C., yield.

¹H-NMR (δ, CDCl₃): 1.20 (s, 9H), 2.27 (s, 3H), 2.72 (AB$_q$, J$_{AB}$=16, Δv=141, 2H), 2.75 (m, 1H), 2.92 (m, 1H), 3.71 (s, 3H), 4.2o (m, 1H), 4.48 (m, 1a), 6.5–7.8 (m, 15H).

¹³C-NMR (δ, CDCl₃): 18.8, 28.5, 36.0, 44.5, 50.0, 51.2, 53.4, 55.2, 105.3, 109.2, 112.0, 126.3, 126.7, 128.4, 128.5, 128.7, 129.7, 131.6, 135.8, 139.3, 139.8, 140.3, 141.2, 155.2, 160.3, 168.1, 174.6.

IR (cm.⁻¹, KBr): 1640 broad (C=O).

FAB MS (%): 529 (parent+1, 35), 456 (100), 307 (44), (62), 208 (54).

Anal. calc'd for C₃₁H₃₆N₄O₄·3/4H₂O: C 68.68, H 6.97, N 10.33. Found: C 68.74, H 6.89, N 10.09.

EXAMPLE 51

N-tert-but 1-2-3-3-3-chlorophenyl)ureido)-2-oxo-5-phenyl-9-methyl-2,3,4,5-tetrahydro-1H-(1)benzazepin-1-yl]ethanoic acid amide:

Prepared from isomer A in Example 49F, M.P. 260°–262° C., 77% yield.

¹H-NMR (δ, CDCl₃): 1.20 (s, 9H), 2.30 (s, 3H), 2.80 (AB$_q$, J$_{AB}$=16, Δv=98, 2H), 2.8–3.0 (m, 2H), 4.26 (m, 1H), 4.48 (m, 1H), 6.17 (bs, 1H), 6.8–7.3 (m, 12H), 7.56 (bs, 1H), 7.96 (m, 1H).

¹³C-NMR (δ, CDCl₃): 18.9, 28.5, 35.6, 44.7, 50.2, 51.5, 54.4, 117.1, 119.2, 122.4, 126.4, 126.7, 128.4, 128.5, 128.8, 129.7, 131.7, 134.4, 135.6, 139.3, 139.8, 140.6, 141.3, 155.1, 167.4, 174.7.

IR (cm.⁻¹, KBr): 1640 broad (C=O).

FAB MS (%): 533/535 (parent, Cl³⁵/Cl³⁷, 23/8), 460 (100), 408 (68), 234 (85), 208 (75).

Anal. calc'd for C₃₁H₃₆N₄O$^{Cl:\ C}$ 67.60, H 6.24, N 10.51. Found: C 67.59, H 6.25, N 10.18.

EXAMPLE 52

N-tert-butyl-2-[3-(3-(3-ethylphenyl)ureido)-2-oxo-5-phenyl-9-methyl-2,3,4,5-tetrahydro-1H-(1)benzazepin-1-yl]ethanoic acid amide Prepared from isomer A in Example 49F, M.P. 222°–224° C., 88% yield.

¹H-NMR (δ, CDCl₃): 1.17 (t, J=7, 3H), 1.20 (s, 9H), 2.28 (s, 3H), 2.55 (q, J=7, 2H), 2.72 (AB$_q$, J$_{AB}$=16, Δv=136, 2H), 2.76 (m, 1H), 2.92 (m, 1H), 4.20 (m, 1H), 4.50 (m, 1H), 6.60 (bs, 1H), 6.8–7.3 (m, 14H).

¹³C-NMR (δ, CDCl₃): 15.6, 18.8, 28.5, 28.9, 36.0, 44.5, 50.0, 51.2, 55.4, 117.4, 119.8, 122.8, 126.3, 126.7, 128.4, 128.5, 128.7, 128.9, 131.6, 135.8, 138.9, 139.3, 139.9, 141.2, 145.4, 155.3, 168.1, 174.6.

IR (cm.⁻¹, KBr): 1640 broad (C=O).

FAB MS (%): 527 (parent+1, 37), 454 (100), 307 (45), 234 (54), 208 (47).

Anal. calc'd for C₃₂H₃₈N₄O₃: C 72.98, H 7.27, N 10.64. Found: C 72.77, H 7.24, N 10.27.

EXAMPLE 53

N-Methyl, tert-butyl-2-[3-(3-(3-tolyl)ureido)-2-oxo-5-(phenyl)-2,3,4,5-tetrahydro-1H-(1)benzazepin-1-yl]ethanoic acid amide Prepared from N-methyl, N-tert-butyl-2-[3-amino-2-oxo-5-(phenyl)-2,3,4,5-tetrahydro-1H-(1)benzazepin-1-yl]ethanoic acid amide as in Example 1, M.P. 140°–150° C., 83% yield.

¹H-NMR (δ, CDCl₃): 1.30 (s, 9H), 2.19 (s, 3H), 2.31 (s, 3H), 2.88 (m, 1H), 3.15 (m, 1H), 3.32 (AB$_q$, J$_{AB}$=16, Δv=297, 2H), 4.20 (m, 1H), 4.68 (m, 1H), 6.6–7.4 (m, 14H), 7.72 (bs, 1H).

¹³C-NMR (δ, CDCl₃): 21.5, 28.1, 30.5, 38.1, 44.4, 49.8, 53.0, 57.4, 116.9, 120.7, 123.0, 124.9, 126.0, 126.6, 127.5, 128.2, 128.3, 128.6, 128.7, 130.4, 138.3, 138.9, 139.5, 141.4, 142.7, 154.9, 166.9, 172.3.

IR (cm.⁻¹, KBr): 1650 broad (C=O).

FAB MS (%): 513 (parent+1, 40), 426 (100), 293 (42), 220 (46), 194 (50).

Anal. calc'd for C₃₁H₃₆N₄O₃: C 72.63, H 7.08, N 10.93. Found: C 72.83, H 7.16, N 10.84.

EXAMPLE 54

N-Methyl, tert-butyl-2-[3-(3-(3-chlorophenyl)ureido)-2-oxo-5-(phenyl)-2,3,4,5-tetrahydro-1H-(1)benzazepin-1-yl]ethanoic acid amide Prepared from N-methyl, N-tert-butyl-2-[3-amino-2-oxo-5-(phenyl)-2,3,4,5-tetrahydro-1H-(1)benzazepin-1-yl]ethanoic acid amide as in Example 1, M.P. 155°–162° C., 97% yield.

¹H-NMR (δ, CDCl₃): 1.32 (s, 9H), 2.50 (s, 3H), 2.84 (m, 1H), 3.02 (m, 1H), 3.40 (AB$_q$, J$_{AB}$=16, Δv=288), 2H),4.26 (m, 1H), 4.62 (m, 1H), 6.8–7.6 (m, 14H), 7.96 (bs, 1H).

¹³C-NMR (δ, CDCl₃): 28.2, 30.7, 38.0, 44.5, 49.6, 53.1, 57.5, 117.4, 118.9, 121.5, 124.7, 126.2, 126.6, 127.5, 128.2, 128.8, 129.3, 130.5, 133.8, 138.7, 141.1, 141.3, 142.6, 154.6, 167.0, 172.8.

IR (cm.⁻¹, KBr): 1650 broad (C=O).

FAB MS (%): 533 (parent+1, 14), 446 (80), 293 (54), 237 (52), 220 (98), 194 (100).

Anal. calc'd for C₃₀H₃₃N₄O₃Cl: C 67.60, H 6.24, N 10.51. Found: C 67.78, H 6.26, N 10.40.

EXAMPLE 55

N-benzyl, tert-butyl-2-(3-(3-(3-tolyl)ureido)-2-oxo-5-(phenyl)-2,3,4,5-tetrahydro-1H-(1)benzazepin-1-yl]ethanoic acid amide Prepared from N-benzyl, N-tert-butyl-2-[3-amino-2-oxo-5-(phenyl)-2,3,4,5-tetrahydro-1H-(1)benzazepin-1-yl]ethanoic acid amide as in Example 1, M.P. 226°–230° C., 63.5% yield.

¹H-NMR (δ, CDCl₃): 1.33 (s, 9H), 2.18 (s, 3H), 2.88 (m, 1H), 3.10 (m, 1H), 3.18 (AB$_q$, J$_{AB}$=16, Δv=243, 2H), 4.0–4.3 (m, 3H), 4.75 (m, 1H), 6.6–7.6 (m, 14H), 8.75 (bs, 1H).

¹³C-NMR (δ, CDCl₃): 21.5, 28.5, 37.9, 44.4, 47.7, 49.5, 53.2, 58.3, 116.8, 120.4, 122.9, 125.5, 125.9, 126.0, 126.3, 127.0, 127.1, 127.6, 127.9, 128.0, 128.3, 128.7, 128.8, 128.9, 130.2, 138.2, 139.2, 139.4, 141.5, 142.3, 155.0, 168.3, 172.8.

IR (cm.⁻¹, KBr): 1650 broad (C=O).

FAB MS (%): 589 (parent+1, 10), 426 (54), 293 (41), 220 (40), 91 (100).

Anal. calc'd for C₃₇H₄₀N₄O₃: C 75.48, H 6.85, N 9.52. Found: C 75.09, H 6.88, N 9.30.

EXAMPLE 56

N-Benzyl, tert-butyl-2-[3-(3-(3-chlorophenyl)ureido)-2-oxo-5-(phenyl)-2,3,4,5-tetrahydro-1H-(1)benzazepin-1-yl]ethanoic acid amide Prepared from N-benzyl, N-tert-butyl-2-[3-amino-2-oxo-5-(phenyl)-2,3,4,5-tetrahydro-1H-(1)benzazepin-1-yl]ethanoic acid amide as in Example 1, M.P. 239°–243° C., 68% yield.

¹H-NMR (δ, CDCl₃): 1.32 (s, 9H), 2.98 (m, 2H), 3.22 (AB$_q$, J$_{AB}$=16, δv=204), 2H), 4.27 (AB$_q$, J$_{AB}$=17, Δv=61), 2H), 4.31 (m, 1H), 5.26 (m, 1H), 6.8–7.6 (m, 14H), 7.79 (bs, 1H).

¹³C-NMR (δ, CDCl₃): 28.6, 37.7, 44.4, 47.7, 49.4, 53.5, 58.5, 117.1, 121.5, 125.5, 125.7, 126.1, 126.2, 126.3, 127.0, 127.6, 127.7, 127.9, 128.7, 128.8, 128.9, 129.2, 130.2, 133.8, 138.1, 139.2, 140.9, 141.4, 142.2, 154.8, 168.1, 173.5.

IR (cm.⁻¹, KBr): 1650 broad (C=O).

FAB MS (%): 609 (parent+1, 8), 446 (56), 293 (37), 220 (57), 194 (44), 91 (100).

Anal. calc'd for C₃₆H₃₇N₄O₃Cl: C 70.98, H 6.12, N 9.20. Found: C 70.68, H 6.30, N 8.95.

EXAMPLE 57

N-Benzyl, tert-butyl-2-[3-(3-(3-methoxyphenyl)ureido]-2-oxo-5-(phenyl)-2,3,4,5-tetrahydro-1H-(1)benzazepin-1-yl]ethanoic acid amide Prepared from N-benzyl, N-tert-butyl-2-[3-amino-2-oxo-5-(phenyl)-2,3,4,5-tetrahydro-1H-(1)benzazepin-1-yl]ethanoic acid amide as in Example 1, M.P. 222°–226° C., 62% yield.

¹H-NMR (δ, CDCl₃): 1.33 (s, 9H), 2.90 (m, 1H), 3.09 (m, 1H), 3.17 (AB$_q$, J$_{AB}$=16, Δv=236, 2H), 3.65 (S, 3H), 4.1–4.3 (m, 3H), 4.77 (m, 1H), 6.4–7.4 (m, 14H), 7.55 (bs, 1H).

¹³C-NMR (δ, CDCl₃): 28.5, 37.9, 44.4, 47.7, 49.4, 53.3, 55.1, 58.3, 104.2, 109.0, 111.6, 125.5, 125.8, 126.2, 126.9, 127.0, 127.6, 127.7, 127.9, 128.0, 128.6 128.8, 129.1, 130.2, 138.3, 139.2, 140.8, 141.4, 142.3, 154.8, 159.9, 168.2, 172.8.

IR (cm.⁻¹, KBr): 1650 broad (C=O)

MS (%): 605 (parent+1, 10, 442 (72), 293 (55), 220 (59), 194 (56), 91 (100).

Anal. calc'd for C₃₇H₄₀N₄O₄·1.5H₂O: C 70.34, H 6.86, N 8.87. Found: C 70.40, H 6.48, N 8.65.

EXAMPLE 58

N-tert-Amyl 2-[3-(3-(3-tolyl)ureido)-2-oxo-5-(phenyl)-2,3,4,5-tetrahydro-1H-(1)benzazepin-1-yl] ethanoic acid amide Prepared from N-tert-amyl 2-[3-amino-2-oxo-5-(phenyl)-2,3,4,5-tetrahydro-1H-(1)benzazepin-1-yl]ethanoic acid amide as in Example 1, M.P. 226°–229° C., 70% yield.

¹H-NMR (δ, CDCl₃): 0.73 (t, J=7, 3H), 1.21 (s, 9H), 1.63 (q, J=7, 2H), 2.23 (s, 3H), 2.88 (m, 1H), 3.04 (m, 1H), 3.26 (AB$_q$, J$_{AB}$=16, Δv=282, 2H), 4.11 (m, 1H), 4.60 (m, 1H), 5.80 (bs, 1H), 6.5–7.4 (m, 13H), 7.70 (bs, 1H).

¹³C-NMR (δ, CDCl₃): 8.3, 21.4, 26.2, 32.8, 37.1, 44.4, 50.2, 53.6, 54.4, 116.7, 120.4, 120.5, 123.5, 124.8, 126.3, 126.5, 127.7, 128.3, 128.6, 129.0, 130.8, 138.3, 138.7, 139.1, 141.2, 141.8, 155.4, 167.5, 173.0.

IR (cm.⁻¹, KBr): 1650 broad (C=O)

FAB MS (%): 513 (parent+1, 65), 426 (50), 119 (100), 103 (48).

Anal. calc'd for C₃₁H₃₆N₄O₃: C 72.63, H 7.08, N 10.93. Found: C 72.57, H 6.78, N 10.67.

EXAMPLE 59

N-tert-Amyl 2-[3-(3-(3-chlorophenyl)ureido)-2-oxo-5-(phenyl)-2,3,4,5-tetrahydro-1H-(1)benzazepin-1-yl]ethanoic acid amide Prepared from N-tert-amyl 2-[3-amino-2-oxo-5-(phenyl)-2,3,4,5-tetrahydro-1H-(1)benzazepin-1-yl]ethanoic acid amide as in Example 1, M.P. 219°–222° C., 73% yield.

¹H-NMR (δ, CDCl₃): 0.74 (t, J=7, 3H), 1.23 (s, 9H), 1.64 (q, J=7, 2H), 2.94 (m, 1H), 3.01 (m, 1H), 3.32 (AB$_q$, J$_{AB}$=16, Δv=274, 2H), 4.15 (m, 1H), 4.59 (m, 1H), 5.73 (bs, 1H), 6.5–7.4 (m, 12H), 7.57 (bs, 1H), 7.97 (bs, 1H).

¹³C-NMR (δ, CDCl₃): 8.4, 26.2, 32.9, 36.9, 44.5, 50.4, 53.2, 54.7, 117.0, 118.9, 119.0, 122.1, 124.3, 124.4, 126.3, 126.4, 126.6, 127.8, 128.3, 129.1, 129.5, 130.9, 134.3, 138.2, 140.7, 141.1, 141.8, 155.1, 167.2, 173.2.

IR (cm.⁻¹, KBr): 1650 broad (C=O)

FAB MS (%): 533/535 (parent+1, Cl³⁵/Cl³⁷ 34/13), 446 (75), 293 (60), 220 (86), 194 (100).

Anal. calc'd for C₃₀H₃₃N₄O₃Cl: C 67.60, H 6.24, N 10.26. Found: C 67.25, H 6.06, N 10.27.

EXAMPLE 60

Trans-1-(t-Butylacetamido)-3-(3-tolylureido)-5,7-diphenylhexahydroazepin-2-one

A. 2,4-Diphenylcyclohexanone

Prepared in analogy with a method in Hussey, A. S. and Herr, R. R., J. Org. Chem., 24, 843, (1959). To a 500 mL round-bottomed flask equipped with N₂ inlet were added 37 g (0.212 mol) of 4-phenylcyclohexanone and 80 mL carbon tetrachloride. To the stirring solution was added dropwise over 30 minutes a solution of 20.5 mL (0.255 mol) sulfuryl chloride in 10 mL carbon tetrachloride. The reaction was stirred 14 hours at room temperature and poured into saturated aqueous sodium bicarbonate solution. The organic layer was separated, washed again with saturated aqueous sodium bicarbonate solution, dried over sodium sulfate, and evaporated to a yellow oil, 34.8 g (78%) which was used directly in the next step.

¹H-NMR (δ, CDCl₃): (mixture of diastereomers) 1.9–3.6 (series of multiplets, 7H), 4.7 and 5.3 (multiplets, 1H), 7.2–7.4 (m, 5H).

IR (cm.⁻¹, KBr): 1735 (C=O)

MS (%): 208/210 (parent, Cl³⁵/Cl³⁷, 36/12), 145 (49), 117 (88), 115 (83), 104 (100), 101 (88), 91 (82), 55 (67).

The oil was dissolved in 400 mL benzene and added dropwise over 40 minutes to 83 mL (250 mmol) of a 3.0M solution of phenylmagnesium bromide in ether, cooling so the temperature did not rise above 10° C. The reaction was then allowed to warm and heated to reflux for 14 hours. It was then cooled, quenched with aqueous ammonium chloride solution, then washed with water and brine, dried over sodium sulfate, and evaporated. The yield was 53.9 g (approximately theoretical), and the crude oil was used directly in the next step.

¹H-NMR (δ, CDCl₃): (mixture of diastereomers) 1.9–3.3 (series of multiplets, 7H), 3.9 (m, 1H), 7.1–7.6 (m, 10H).

B. 2,4-Diphenylcyclohexanone oxime

The above oil was dissolved in 200 mL methanol, and a solution of 18.6 g (0.267 mol) hydroxylamine hydrochloride and 37.2 mL (0.267 mol) triethylamine in 100 mL methanol added. The solution was decanted off the oily precipitate which separated and stirred at room temperature for 1.5 hours. The white precipitate was filtered and dried to give 13.6 g (31%) of a white solid, mp 214°–215° C.

C. 5,7-diphenylhexahydroazepin-2-one

To a 250 mL round-bottomed flask equipped with N₂ inlet were added 8.52 g (32.15 mmol) 2,4-diphenylcyclohexanone oxime and 110 mL pyridine. Once the solid had dissolved, the solution was cooled to 0° C., and 12.3 g (64.3 mmol) p-toluenesulfonyl chloride was added. The reaction was allowed to stir for 16 hours while the ice bath melted and the reaction warmed to room temperature. It was then poured into 300 mL 3N HCl, extracted into ethyl acetate, and the organic layer washed with additional HCl and brine, dried over sodium sulfate, and evaporated. The residue was chromatographed on silica gel using methanol/methylene chloride as eluant to afford 2.4 g (28%) of an oil which was crystallized from isopropanol to give mp 171°–173.5° C.

¹H-NMR (δ, CDCl₃): 2.0 (m, 1H), 2.1 (m, 3H), 2.75 (m, 2H), 2.95 (m, 1H), 4.60 (m, 1H), 5.78 (bs, NH, 1H), 7.1–7.5 (m, 10H).

¹³C-NMR (δ, CDCl₃): 30.3, 36.3, 45.3, 48.6, 58.1, 126.3, 126.6, 128.4, 128.7, 129.2, 142.1, 146.1, 176.5.

IR (cm.⁻¹, KBr): 1662 (C=O).

MS (%): 265 (parent, 82), 266 (85), 160 (47), 106 (100), 104 (87).

Anal. calc'd for C₁₈H₁₉NO: C 81.48, H 7.21, N 5.27. Found C 81.32, H 7.41, N 5.28.

D. 3-Bromo-5,7-diphenylhexahydroazepin-2-one

To a 250 mL round-bottomed flask equipped with addition funnel and N₂ inlet were added 1.51 g (7.27 mmol) phosphorus pentachloride and 25 mL dry methylene chloride. The mixture was cooled with stirring to 0° C., and a solution of 1.93 g (7.27 mmol) 5,7-diphenylhexahydroazepin-2-one and 1.18 mL (14.5 mmol) pyridine in 50 mL methylene chloride was added dropwise over 20 minutes. The reaction was stirred 5 minutes at 0° C., then 0.82 mL (16.0 mmol) bromine in 5 mL methylene chloride was added dropwise over 5 minutes. The reaction was stirred 5 minutes at 0° C., then 1.8 hours at room temperature. The reaction was evaporated, taken up in 40 mL of 1:1 tetrahydrofuran:water, and stirred for 1.2 hours. The reaction was then poured into water and extracted into ethyl acetate. The organic layer was washed with aqueous sodium bisulfite solution and brine, dried over sodium sulfate, and evaporated to an oil.

The oil was taken up in 20 mL methylene chloride and 20 mL ethanol, and hydrogenated under 42 psi hydrogen in the presence of 0.30 g 10% palladium-on-carbon and 3 drops of quinoline for 1 hour. Tlc showed mostly desired monobromo product at R$_f$=0.4, with a little dibromo precursor at R$_f$=0.7 and starting lactam at R$_f$=0.15, in 1/1-ethyl acetate/hexane. The reaction was filtered through Celite with ethanol and methylene chloride, evaporated, and chromatographed on silica gel using 2/1-hexane/ethyl acetate as eluant to afford 2.06 g (82%) of a foam M.P. 70°–78° C.

¹H-NMR (δ, CDCl₃): (mixture of diastereomers) 1.9–2.7 (m, 4H), 3.12 and 3.52 (multiplets, 1H), 4.52 and 4.76 (multiplets, 1H), 5.01 (m, 1H), 5.79 and 5.89 (broad singlets, 1H, NH), 7.1–7.4 (m, 10H).

¹³C-NMR (δ, CDCl₃): 42.4, 44.0, 48.0, 50.5, 57.6, 126.3, 126.6, 126.9, 127.1, 128.7, 128.9, 129.3, 129.4, 169.6.

IR (cm.⁻¹, KBr): 1667 (C=O).

MS (%): 343/345 (11/10, parent for Br⁷⁹/⁸¹), 236 (32), 117 (32), 106 (100), 91 (39), 55 (31).

Anal. calc'd for C₁₈H₁₈NOBr: C 62.80, H 5.27, N 4.07. Found: C 62.86, H 5.26, N 3.98.

E.  1-(t-Butylacetamido)-3-bromo-5,7-diphenylhexahydroazepin-2-one

To a 100 mL 3-necked round-bottomed flask equipped with addition funnel and N₂ inlet were added 0.32 g (6.59 mmol) sodium hydride, which was then washed with hexane, and 4 mL dry tetrahydrofuran. To the stirring suspension was added a solution of 2.06 g (5.99 mmol) 3-bromo-5,7-diphenylhexahydroazepin-2-one and 1.59 g (6.59mmol) t-butyl iodoacetamide. The reaction was stirred at room temperature for 60 hours, quenched with ammonium chloride solution, then poured into water, extracted twice into ethyl acetate, washed with brine, dried over sodium sulfate, and evaporated. The residue was chromatographed on silica gel using 2/1-hexane/ethyl acetate as eluant to afford 1.585 g (58%) of an oil, R$_f$=0.4 (1/1-hexane ethyl acetate).

¹H-NMR (δ, CDCl₃): (mixture of diastereomers) 1.22 and 1.25 (singlets, 9H, ratio 35/65), 2.0–2.7 (m, 4H), 3.08 and 3.21 (multiplets, 1H), 3.5–3.9 (m, 2H), 5.01 and 5.4–5.7 (m, 2H), 7.1–7.4 (m, 10H).

¹³C-NMR (δ, CDCl₃): 14.2, 26.9, 28.7, 40.6, 43.9, 51.1, 60.3, 61.7, 126.8, 127.0, 128.2, 128.4, 128.7, 128.9, 139.5, 144.6, 167.5, 170.0.

IR (cm.⁻¹, KBr): 1675 and 1632 (C=O).

MS (%): 377 (parent-Br, 39), 304 (42), 219 (21), 144 (25), 118 (31), 117 (33), 115 (42), 104 (21), 91 (100), 57 (50), 55 (34).

F.  1-(t-Butylacetamido)-3-azido-5,7-diphenylhexahydroazepin-2-one

To a 100 mL round-bottomed flask equipped with N₂ inlet were added 1.58 g (3.46 mmol) 1-(t-butylacetamido)-3-bromo-5,7-diphenylhexahydroazepin-2-one, 5 mL dry dimethylformamide, and 0.27 g (4.15 mmol) sodium azide. The reaction was heated at 80° C. for 3.5 days, cooled, poured into water, and extracted into ethyl acetate. The organic layer was washed with water and brine, dried over sodium sulfate, and evaporated. The residue was chromatographed on silica gel using 40% ethyl acetate in hexane as eluant to afford 1.09 g (75%) of an oil, which was found to be an 8/3 mixture of diastereomers, R$_f$=0.4–0.5 in 1/1-ethyl acetate/hexane.

1H-NMR (δ, CDCl₃): 1.21 and 1.31 (singlets, 9H), 2.17 and 2.58 (multiplets, 4H), 3.05 and 3.32 (multiplets, 1H), 3.57 (AB$_q$, J$_{AB}$=16, Δv=213 for one isomer of the 2 proton signal CH₂CONHt-butyl), 4.4–5.0 (multiplets, 2H), 5.68 and 6.17 (singlets, 1H, NH), 7.0–7.3 (m, 10H).

IR (cm.⁻¹, KBr): 2105 (N₃), 1647 (C=O).

MS (%): 377 (parent-N₃, <1), 319 (parent-(CONHt-butyl), 4), 235 (21), 146 (43), 115 (47), 104 (73), 103 (40), 91 (100), 84 (32), 57 (46).

G.  1-(t-Butylacetamido)-3-amino-5,7-diphenylhexahydroazepin-2-one

A solution of 1.09 g (2.60 mmol) 1-(t-butylacetamido)-3-azido-5,7-diphenylhexahydroazepin-2-one in 30 mL ethanol and 15 mL methylene chloride was hydrogenated at 42 psi in the presence of 0.40 g 10% palladium-on-carbon for 36 hours. The reaction showed R$_f$=0.30/0.15 iodoplatinate positive, in 30% methanol in ethyl acetate. It was filtered through Celite with ethanol and methylene chloride, evaporated, and chromatographed on silica gel using 30% methanol in ethyl acetate as eluant to afford 300 mg (29%) of the less polar diastereomer as an oil and 420 mg (41%) of the more polar diastereomer as an oil.

Less polar diastereomer:

¹H-NMR (δ, CDCl₃): 1.25 (singlet, 9H), 2.18, 2.50 and 3.23 (multiplets, 7H), 4.52 and 4.90 (multiplets, 2H), 6.5 (broad singlet, 1H, NH), 7.0–7.4 (m, 10H).

¹³C-NMR (δ, CDCl₃): 28.8, 37.7, 40.5, 51.3, 51.7, 52.7, 60.3, 64, 125.6, 126.5, 126.8, 127.8, 128.7, 129.1, 140.7, 145.4, 167.9, 171.

IR (cm.⁻¹, KBr): 1655 (C=O).

More polar diastereomer:

¹H-NMR (δ, CDCl₃): 1.20 (singlet, 9H), 1.9–2.5 (multiplets, 4H), 3.10 (m, 1H), 3.56 (AB$_q$, J$_{AB}$=16, Δv=213, 2H), 4.12 (d, J=16, 1H), 4.99 (d, J=10, 1H), 5.68 (broad singlet, 1H, NH), 7.1–7.4 (m, 10H).

¹³C-NMR (δ, CDCl₃): 28.6, 39.4, 41.8, 46.6, 48.3, 50.8, 53.2, 60.7, 126.7, 126.8, 128.5, 128.6, 128.8, 129.5, 138.4, 145.5, 168.0, 177.4.

IR (cm.⁻¹, KBr): 1645 and 1670 (shoulder) (C=O).

MS (%): 393 (parent, 1.4), 265 (17), 193 (24), 132 (100), 91 (27).

H.  trans-1-(t-Butylacetamido)-3-(3-tolylureido)-5,7-diphenylhexahydroazepin-2-one To a 35 mL round-bottomed flask equipped with N₂ inlet were added 150 mg (0.382 mmol) 1-(t-butylacetamido)-3-amino-5,7-diphenylhexahydroazepin-2-one (less polar diastereomer), 4 mL 1,2-dichloroethane, and 49 mL (0.382 mmol) 3-tolylisocyanate. The reaction was stirred at room temperature for 2.7 hours, diluted with 10 volumes of diisopropyl ether, stirred 30 minutes, filtered, washed with diisopropyl ether, and dried to a white solid, M.P. 245°–246° C., 109 mg (54%).

¹H-NMR (δ, CDCl₃): 1.26 (singlet, 9H), 1.7–2.6 (multiplets, 5H), 2.23 (s, 3H), 3.64 (m, 1H), 3.80 (AB$_q$, J$_{AB}$=16, Δv=399, 2H), 4.14 and 4.6–4.8 (multiplets, 2H), 6.57 (d, J=9, 1H), 6.70 (d, J=7, 1H), 7.0–7.6 (m, 10H), 8.33 (broad singlet, 1H).

IR (cm.⁻¹, KBr): 1673 and 1640 (C=O).

MS (%): 526 (parent, <1), 235 (73), 234 (82), 193 (36), 132 (100), 57 (32), 43 (46), 41 (32).

Anal. calc'd for C₃₂H₃₈N₄O₃•1.75 H₂O: C 68.86, H 7.49, N 10.04. Found: C 68.90, H 7.25, N 9.86.

EXAMPLE 61 trans-1-(t-Butylacetamido)-3-(3-methoxyphenylureido)-5,7-diphenylhexahydroazepin-2-one Prepared from the less polar amine diastereomer in Example 60G in 49% yield, mp 242°–244° C.

¹H-NMR (δ, CDCl₃): 1.26 (singlet, 9H), 1.7–2.6 (multiplets, 5H), 3.64 (m, 1H), 3.69 (s, 3H), 3.81 (AB$_q$, J$_{AB}$=16, Δv=401, 2H), 4.14 and 4.6–4.8 (multiplets, 2H), 6.6–6.9 (multiplets, 2H), 7.0–7.6 (m, 10H), 8.34 (broad singlet, 1H).

IR (cm.⁻¹, KBr): 1673 and 1640 (C=O)

MS (%): 542 (parent, 0.9), 348 (16), 305 (68), 235 (58), 234 (65), 149 (100), 132 (89), 123 (33), 91 (39), 57 (39), 44 (47).

Anal. calc'd for C₃₂H₃₈N₄O₄•1.5 H₂O: C 67.47, H 7.25, N 9.83. Found: C 67.52, H 7.17, N 9.60.

EXAMPLE 62 cis-1-(t-Butylacetamido)-3-(3-tolylureido)-5,7-diphenylhexahydroazepin-2-one

Prepared from the more polar amine diastereomer in Example 60G in 68% yield, M.P. 253°–253.5° C.

$^1$H-NMR ($\delta$, CDCl$_3$): 1.15 (singlet, 9H), 1.9–2.7 (multiplets, 4H), 2.22 (s, 3H), 3.27 (m, 1H), 3.50 (AB$_q$, J$_{AB}$=16, $\Delta v$=224, 2H), 5.09 (dd, J=1,5, 1H), 5.29 (d, J=10, 1H), 6.69 (d, J=7, 1H), 6.83 (d, J=6, 1H), 7.0–7.6 (m, 11H).

IR (cm.$^{-1}$, KBr): 1660 (broad, C=O)

MS (%): 526 (parent, 0.8), 320 (32), 319 (38), 235 (44), 234 (44), 133 (100), 132 (91), 57 (41), 44 (36), 41 (38), 39 (33).

Anal. calc'd for C$_{32}$H$_{38}$N$_4$O$_3$: C 72.98, H 7.27, N 10.64. Found: C 72.94, H 7.31, N 10.45.

EXAMPLE 63

1-(t-Butylacetamido)-3-(3-methoxyphenylureido)-5,7-diphenylhexahydroazepin-2-one Prepared from the more polar amine diastereomer in Example 60G in 43% yield, mp 166°–173° C.

$^1$H-NMR ($\delta$, CDCl$_3$): 1.15 (singlet, 9H), 1.9–2.7 (multiplets, 4H), 3.25 (m, 1H), 3.52 (AB$_q$, J$_{AB}$=16, $\Delta v$=225, 2H), 3.69 (s, 3H), 5.09 (m, 1H), 5.29 (d, J=10, 1H), 6.45 (d, J=8, 1H), 6.84 (broad s, 1H), 7.0–7.6 (m, 11H).

IR (cm.$^{-1}$, KBr): 1645 (broad, C=O).

MS (%): 542 (parent, <1), 265 (15), 235 (37), 234 (340), 193 (18), 149 (100), 123 915), 91 (41), 78 (18), 57 (16).

Anal. calc'd for C$_{32}$H$_{38}$N$_4$O$_4$: C 70.83, H 7.06, N 10.32. Found: C 70.66, H 6.80, N 10.32.

EXAMPLE 64

1-(t-Butylacetamido)-3-(3-chlorophenylureido)-5,7-diphenylhexahydroazepin-2-one

Prepared from the more polar amine diastereomer in Example 60G in 36% yield, M.P. 78°–185° C.

$^1$H-NMR ($\delta$, CDCl$_3$): 1.15 (singlet, 9H), 1.9–2.7 (multiplets, 4H), 3.27 (m, 1H), 3.51 (AB$_q$, J$_{AB}$=16, $\Delta v$=226, 2H), 5.09 (dd, J=1,5, 1H), 5.29 (d, J=10, 1H), 6.9–7.6 (m, 12H), 7.68 (s, 1H).

IR (cm.$^{-1}$, KBr): 1665 and 1642 (and shoulder at 1682) (C=O).

MS (%): 546/548 (parent, Cl$^{35/37}$, <1), 265 (14), 193 (21), 153/155 (100/34, Cl$^{35/37}$), 115 (21), 91 (28), 90 (25), 58 (29).

Anal. calc'd for C$_{31}$H$_{35}$N$_4$O$_3$Cl: C 68.06, H 6.45, N 10.24. Found: C 67.73 H 6.13, N 10.07.

HRMS calc'd for C$_{31}$H$_{35}$N$_4$O$_3$Cl$^{35}$: 546.23895. Found: 546.23581.

EXAMPLE 65

1-(t-Butylacetamido)-3-(3-ethylphenylureido)-5,7-diphenylhexahydroazepin-2-one

Prepared from the more polar amine diastereomer of Example 60G in 46% yield, M.P. 233°–234° C.

$^1$H-NMR ($\delta$, CD$_3$SOCD$_3$): 1.14 (t, J=7, 3H), 1.15 (singlet, 9H), 1.8–2.1 (m, 3H), 2.49 (m, 2H), 2.5–2.7 (m, 1H), 3.23 (m, 1H), 3.51 (AB$_q$, J$_{AB}$=16, $\Delta v$=225, 2H), 5.07 (m, 1H), 5.28 (d, J=10, 1H), 6.72 (d, J=8, 1H), 6.82 (d, J=5, 1H), 7.0–7.6 (m, 14H), 8.94 (bs, 1H).

$^{13}$C-NMR ($\delta$, CD$_3$SOCD$_3$): 15.6, 22.8, 28.5, 45.0, 47.0, 49.9, 51.5, 59.4, 120.6, 126.8, 128.5, 129.4, 139.2, 140.5, 144.2, 146.3, 154.1, 167.3, 173.3.

IR (cm.$^{-1}$, KBr): 1660 (broad, C=O).

MS (%): 540 (parent, 2), 3235 (21), 147 (32), 132 (100), 121 (48), 91 (31).

Anal. calc'd for C$_{33}$H$_{40}$N$_4$O$_3$•1/2H$_2$O: C 72.10, H 7.52, N 10.19. Found: C 72.15, H 7.16, N 9.74 (–0.45).

EXAMPLE 66

1-(t-Butylacetamido)-3-(3-trifluoromethylphenylureido)-5,7-diphenylhexahydroazepin-2-one Prepared from the more polar amine diastereomer of Example 60G in 36% yield, M.P. 263°–264° C.

$^1$H-NMR ($\delta$, CD$_3$SOCD$_3$): 1.15 (singlet, 9H), 1.8–2.1 (m, 3H), 2.58 (m, 1H), 3.23 (m, 1H), 3.51 (AB$_q$, J$_{AB}$=16, $\Delta v$=227, 2H), 5.10 (dd, J=1,5, 1H), 5.30 (d, J=10, 1H), 6.95 (d, J=5, 1H), 7.02 (s, 1H), 7.1–7.5 (m, 13H), 8.00 (bs, 1H), 9.41 (bs, 1H).

$^{13}$C-NMR ($\delta$, CD$_3$SOCD$_3$): 28.5, 44.9, 47.0, 50.0, 51.6, 59.4, 126.3, 126.8, 128.1, 128.4, 128.5, 129.4, 129.8, 139.2, 141.3, 146.2, 154.0, 167.2, 173.1.

IR (cm.$^{-1}$, KBr): 1660 (broad, C=O).

MS (%): 580 (parent, 5), 262 (50), 193 (62), 187 (65), 132 9100), 91 (87), 57 (99).

Anal. calc'd for C$_{32}$H$_{35}$N$_4$O$_3$F$_3$•1/2H$_2$O: C 65.18, H 6.15, N 9.50. Found: C 62.25, H 5.93, N 9.18.

EXAMPLE 67

1-(t-Butylacetamido)-3-(3-methylthiophenylureido)-5,7-diphenylhexahydroazepin-2-one Prepared from the more polar amine diastereomer of Example 60G of 49% yield, M.P. 170°–176° C.

$^1$H-NMR ($\delta$, CD$_3$SOCD$_3$): 1.15 (singlet, 9H), 1.9–2.1 (m, 3H), 2.41 (s, 3H), 2.62 (m, 1H), 3.27 (m, 1H), 3.52 (AB$_q$, J$_{AB}$=16, $\Delta v$=226, 2H), 5.11 (dd, J=1,5, 1H), 5.30 (d, J=10, 1H), 6.77 (d, J=5, 1H), 6.85 (d, J=5, 1H), 7.0–7.6 (m, 14H), 9.06 (bs, 1H).

$^{13}$C-NMR ($\delta$, CD$_3$SOCD$_3$): 14.6, 28.5, 44.9, 47.0, 49.9, 51.5, 59.4, 114.0, 114.4, 118.5, 126.3, 126.8, 126.9, 128.5, 128.6, 129.2, 129.4, 138.5, 139.2, 141.1, 146.2, 154.0, 167.3, 173.2.

IR (cm.$^{-1}$, KBr): 1660 (broad, C=O).

FAB MS (%): 559 (parent+1, 10), 394 (12), 233 913), 193 914), 155 (97), 135 924), 119 (100), 103 (38).

Anal. calc'd for C$_{32}$H$_{38}$N$_4$O$_3$S: C 68.79, H 6.85, N 10.03. Found: C 68.91, H 6,948, N 9.96.

EXAMPLE 68

1-(t-Butylacetamido)-3-(3-carboxamidophenylureido)-5,7-diphenylhexahydroazepin-2-one Prepared from the more polar amine diastereomer of Example 60G in 18% yield, M.P. 155°–165° C.

$^1$H-NMR ($\delta$, CDCl$_3$): 1.145 (singlet, 9H), 2.00 (m, 1H), 2.2–2.5 (m, 3H), 3.32 (m, 1H), 3.66 (AB$_q$, J$_{AB}$=16, $\Delta v$=73, 2H), 5.25 (bs, 2H), 5.28 (m, 1H), 5.76 (m, 1H), 7.1–7.4 (m, 13H), 7.67 (d, J=7, 1H), 7.80 (s, 1H), 8.18 (bs, 1H), 9.09 (bs, 1H).

$^{13}$C-NMR (δ, CDCl$_3$): 28.6, 38.0, 39.2, 45.7, 47.9, 51.4, 56.7, 61.0, 112.7, 118.4, 126.6, 126.8, 127.0, 128.1, 128.2, 128.3, 128.5, 128.6, 128.7, 128.8, 129.0, 129.4, 129.5, 129.6, 129.7, 137.8, 139.3, 145.0, 167.0, 174.8, 179.9.

IR (cm.$^{-1}$, KBr ): 1660 (broad, C=O).

FAB MS (%): 555 (parent, 62), 481 (15), 424 (23), 193 (56), 155 (23), 119 (100), 103 (38).

Anal. calc'd for C$_{32}$H$_{37}$N$_5$O$_4$·1/3H$_2$O: C 68.43, H 6.76, N 12.47. Found: C 68.47, H 6.47, N 12.44.

EXAMPLE 69

1-(t-Butylacetamido)-3-(4-tolylureido)-5,7-diphenylhexahydroazepin-2-one

Prepared from the more polar amine diastereomer in Example 60G in 25% yield, M.P. 156°–165° C.

$^1$H-NMR (δ, CD$_3$SOCD$_3$): 1.15 (singlet, 9H), 1.9–2.1 (m, 3H), 2.20 (s, 3H), 2.61 (m, 1H), 3.27 (m, 1H), 3.51 (AB$_q$, J$_{AB}$=16, Δν=225, 2H), 5.08 (m, 1H), 5.29 (d, J=10, 1H), 6.78 (d, J=5, 1H), 7.0 and 7.2–7.4 (m, 15H), 8.87 (bs, 1H).

$^{13}$C-NMR (δ, CD$_3$SOCD$_3$): 20.3, 28.5, 45.0, 47.0, 49.9, 51.5, 59.4, 117.6, 126.3, 126.8, 128.5, 128.7, 129.1, 129.2, 129.3, 129.4, 129.5, 129.7, 138.0, 139.3, 146.3, 154.2, 167.3, 173.4.

IR (cm.$^{-1}$, KBr): 1660 (broad, C=O).

FAB MS (%): 527 (parent+1, 30), 454 (6), 313 (12), 235 910), 157 (100).

Anal. calc'd for C$_{32}$H$_{38}$O$_3$·2/3H$_2$O: C 71.35, H 7.36, N 10.40. Found: C 71.20, H 7.26, N 10.23.

EXAMPLE 70

Resolution of 1-(N-t-butylacetamido)-3-(3-tolylureido)-5,7-diphenyl-hexahydroazepin-2-one Carried out in analogy with a procedure developed by Bock, M. G., et al., J. Org. Chem., 52, 3232–3239 (1987) using L-phenylalanine as the resolving agent:

A. 1-(N-t-Butylacetamido)-3-(2-(t -butoxycarbonylamino)-3-phenylpropionamido)-5,7-diphenylhexahydroazepin-2-one To a 100 mL round-bottomed flask equipped with N$_2$ inlet were added 650 mg (1.65 mmol) of the more polar isomer of 1-(t-butylacetamido)-3-amino-5,7-diphenylhexahydroazepin-2-one, 439 mg (1.65 mmol) t-BOC-L-phenylalanine, 253 mg (1.65 mmol) N-hydroxybenzotriazole, 13 mL dry methylene chloride, 317 mg (1.65 mmol) ethyl(dimethylaminopropyl) carbodiimide, and 0.415 mL (2.98 mmol) triethylamine. The reaction was stirred at room temperature for 14 hr, poured into water, and extracted into ethyl acetate. The organic layer was washed with 1N HCl, water, saturated aqueous sodium bicarbonate solution, and brine, dried over sodium sulfate, and evaporated. TLC showed one spot of R$_f$=0.30 in 1/1-ethyl acetate/hexane for the product, which was a foam, 950 mg (90%), α$_D$=−5.77° (C=0.8, CH$_2$Cl$_2$).

$^1$H-NMR (δ, CDCl$_3$): 1.20 (singlet, 9H), 1.28 (s, 9H), 1.9–2.2 (m, 3H), 2.43 and 2.57 (multiplets for the two diastereomers, 1H), 2.8–3.0 (m, 3H), 3.53 and 3.54 (two AB$_q$ patterns for each diastereomer, J$_{AB}$=15 and 15, Δν=198 and 195, 2H), 4.18 and 4.32 (multiplets for the two diastereomers, 1H), 5.0–5.2 (m, 2H), 5.48 and 5.66 (broad singlets for each diastereomer, 1H), 7.0–7.4 (m, 17H).

$^{13}$C-NMR (δ, CDCl$_3$): (pairs of peaks were observed because of the two diastereomers) 28.2 and 28.6, 38.6 and 39.0, 45.8 and 45.9, 48.0 and 48.2, 50.9 and 51.0, 51.4 and 51.5, 55.2 and 55.8, 60.3, 61.1 and 61.2, 126.7, 126.8, 126.9, 128.6, 128.8, 128.9, 129.3, 129.5, 129.6, 129.7, 129.8, 130.0, 138.0, 138.2, 145.0, 145.2, 167.3 and 167.4, 170.2 and 170.5, 171.0 and 171.05, 173.0 and 173.1.

IR (cm.$^{-1}$, KBr): 1723, 1667, and 1635 (C=O).

MS (%): 640 (parent, 0.35), 452 (27), 376 (32), 264 (26), 193 (46), 120 (100), 91 (92).

B. 1-(N-t-Butylacetamido)-3-(2-amino-3-phenylpropionamido)-5,7-diphenyl-hexahydroazepin-2-one To a 125 mL round-bottomed flask equipped with N$_2$ inlet were added 950 mg (1.49 mmol) 1-(N-t-butylacetamido)-3-(2-(t-butoxycarbonylamino)-3-phenylpropionamido)-5,7-diphenylhexahydroazepin-2-one (mixture of diastereomers) and 40 mL ethyl acetate. The solution was cooled to 0° C., saturated with HCl gas, and stirred at 0° C. for 20 minutes, then at room temperature for 40 minutes. The reaction was poured into aqueous sodium bicarbonate solution, diluted with ethyl acetate, and the organic layer washed with additional aqueous sodium bicarbonate solution and brine, dried over sodium sulfate, and evaporated. The diastereomeric products were separated by chromatography on silica gel using ethyl acetate/methanol as eluant to afford each diastereomer as an oil.

Less polar diastereomer (R$_f$=0.4 in 10% methanol in ethyl acetate): α$_D$=−28.2° (C=1.5, CH$_2$Cl$_2$), 50% yield.

$^1$H-NMR (δ, CDCl$_3$): 1.24 (singlet, 9H), 1.8–2.6 (series of multiplets, 4H), 3.1 (m, 3H), 3.58 (AB$_q$, J$_{AB}$=16, Δν=202, 2H), 3.59 (m, 1H), 4.18 and 4.32 (multiplets for the two diastereomers, 1H), 5.12 (d, J=10, 1H), 5.17 (m, 1H), 5.49 (bs, 1H), 7.0–7.4 (m, 15H), 8.49 (d, J=7, 1H).

$^{13}$C-NMR (δ, CDCl$_3$): 28.7, 39.2, 41.1, 46.0, 48.1, 51.0, 56.5, 60.3, 61.2, 126.7, 126.8, 127.0, 128.4, 128.6, 128.9, 129.0, 129.3, 129.5, 137.8, 138.1, 145.2, 167.5, 173.5.

IR (cm.$^{-1}$, KBr): 1665 and 1635 (C=O)

MS (%): 540 (parent, 3), 449 (32), 376 (41), 264 (35), 193 (38), 120 (100), 91 (43).

More polar diastereomer (R$_f$=0.2 in 10% methanol in ethyl acetate): α$_D$=−32.2° (C=1.5, CH$_2$Cl$_2$), 50% yield.

$^1$H-NMR (δ, CDCl$_3$): 1.23 (singlet, 9H), 1.8–2.6 (series of multiplets, 4H), 3.1 (m, 3H), 3.55 (m, 1H), 3.58 (AB$_q$, J$_{AB}$=16, Δν=220, 2H), 4.18 and 4.32 (multiplets for the two diastereomers, 1H), 5.10 (d, J=10, 1H), 5.17 (m, 1H), 5.49 (bs, 1H), 7.0–7.4 (m, 15H), 8.30 (d, J=7, 1H).

$^{13}$C-NMR (δ, CDCl$_3$): 28.7, 39.2, 41.2, 46.0, 48.1, 51.0, 56.9, 60.3, 61.2, 126.7, 126.8, 127.0, 128.4, 128.6, 128.9, 129.0, 129.3, 129.5, 138.1, 138.2, 145.1, 167.5, 173.5.

IR (cm.$^{-1}$, KBr): 1665 and 1635 (C=O)

MS (%): 540 (parent, 2), 449 (37), 376 (53), 264 (35), 193 (35), 120 (100), 91 (42).

C. (−)-1-(N-t-butylacetamido)-3-amino-5,7-diphenylhexahydroazepin-2-one

To a 100 mL round-bottomed flask equipped with N$_2$ inlet and condenser were added 0.40 g (0.745 mmol) 1-(N-t-butylacetamido)-3-(2-amino-3-phenylpropionamido)-5,7-diphenyl-hexahydroazepin-2-one (more polar isomer from above), 8 mL 1,2-dichloroethane, and 0.093 mL (0.782 mmol) phenylisothiocyanate. The reaction was refluxed for 1 hr, cooled, and evaporated. The residue was taken up in 10 mL trifluoroacetic acid and heated at 70°–80° C. for 2 hr. The reaction was cooled, and the product precipitated as a salt with ether and hexane. The precipitate was collected, dissolved in ethyl acetate, washed with aqueous sodium bicarbonate solution and brine, dried over sodium sulfate, and evaporated. The oil solidified from chloroform to give mp 204°–205° C., 0.30 g (100%), α$_D$=−3.72° (C=0.5, TFA). $^1$H-NMR and $^{13}$C-NMR spectra match those of the racemate.

D. (+)-1-(N-t-butylacetamido)-3-amino-5,7-diphenylhexahydroazepin-2-one

Prepared as above from 1-(N-t-butylacetamido)-3-(2-amino-3-phenylpropionamido)-5,7-diphenylhexahydroazepin-2-one (less polar isomer) as an oil in 92% yield, $\alpha_D$=+3.21° (c=0.8, ethyl acetate). The $^1$H-NMR spectrum matches that of the racemate.

E. (−)-1-(N-t-butylacetamido)-3-(3-tolylureido)-5,7-diphenylhexahydroazepin-2-one To a 35 mL round-bottomed flask equipped with $N_2$ inlet and condenser were added 293 mg (0.745 mmol) (−)-1-(N-t-butylacetamido)-3-amino-5,7-diphenylhexahydroazepin-2-one, 10 mL ethyl acetate, and 0.096 mL (0.745 mmol) m-tolylisocyanate. The reaction was refluxed for 2.5 hr, cooled, and evaporated. The residue was chromatographed on silica gel using hexane/ethyl acetate as eluant to afford an oil which was crystallized from methylene chloride/isopropyl ether to a give mp 140°–150° C., 71 mg (18%), $\alpha_D$=−18.6° (c=1, $CH_2Cl_2$). The $R_f$ value on TLC and $^1$H-NMR spectrum match those of the racemate.

Anal. calc'd for $C_{32}H_{38}N_4O_3 \cdot 1/2H_2O$: C 71.75, H 7.34, N 10.46. Found: C 71.66, H 6.75 (−0.59), N 10.29.

F. (+)-1-(N-t-butylacetamido)-3-(3-tolylureido)-5,7-diphenyl-hexahydroazepin-2-one Prepared as above from (+)-1-(N-t-butylacetamido)-3-amino-5,7-diphenyl-hexahydroazepin-2-one as an oil in 30% yield, which was crystallized from methylene chloride/isopropyl ether to a give mp 140°–150° C., in 15% yield, $\alpha_D$=+18.2° (c=1, $CH_2Cl_2$). The $R_f$ value on TLC and $^1$H-NMR and $^{13}$C-NMR spectra match those of the racemate.

Anal. calc'd for $C_{32}H_{38}N_4O_3 \cdot 1/2H_2O$: C 71.75, H 7.34, N 10.46. Found: C 71.65, H 6.89 (−0.45), N 10.49.

EXAMPLE 71

(1-t-Butoxycarbonylmethyl)-3-(3-tolylureido)-7-cyclohexylhexahydroazepin-2-one

Prepared from (1-t-butoxycarbonylmethyl)-3-amino-7-cyclohexyl-hexahydroazepin-2-one as in Example 11 in 31% yield, M.P. 108°–110° C.

$^1$H-NMR ($\delta$, $CDCl_3$): 0.8–1.0 (m, 2H), 1.1–1.3 (m, 4H), 1.37 (s, 9H), 1.6–1.9 (m, 10H), 2.08 (m, 1H), 2.25 (s, 3H), 3.42 (t, J=7, 1H), 3.88 ($AB_q$, $J_{AB}$=17, $\Delta v$=180, 2H), 5.01 (m, 1H), 6.65 and 7.1–7.4 (m, 6H (includes broad singlets for 2 NH signals)).

$^{13}$C-NMR ($\delta$, $CDCl_3$): 21.5, 25.7, 25.9, 26.0, 26.2, 27.2, 28.0, 30.1, 31.7, 32.2, 39.4, 45.6, 51.5, 63.4, 81.8, 123.6, 128.7, 138.7, 139.1, 155.2, 168.4.

IR (cm.$^{-1}$, KBr): 1730 ($CO_2R$) and 1640 (CONR)

MS (%): 457 (2, parent), 295 (23), 185 (23), 107 (100).

HRMS calc'd for $C_{26}H_{40}N_3O_4$: 458.2984. Found: 458.3057.

EXAMPLE 72

1-t-Butoxycarbonylmethyl)-3-((3-trifluoromethylphenyl)ureido)-7-cyclohexylhexahydroazepin-2-one Prepared from (1-t-butoxycarbonylmethyl)-3-amino-7-cyclohexyl-hexahydroazepin-2-one as in Example 11 in 36% yield, M.P. 114°–117° C.

$^1$H-NMR ($\delta$, $CDCl_3$): 0.8–1.0 (m, 2H), 1.1–1.3 (m, 4H), 1.34 (s, 9H), 1.6–1.9 (m, 10H), 2.0 (m, 1H), 3.48 (t, J=7, 1H), 3.90 ($AB_q$, $J_{AB}$=17, $\Delta v$=160, 2H), 5.04 (m, 1H), 6.8–8.0 (series of multiplets, 6H).

$^{13}$C-NMR ($\delta$, $CDCl_3$): 25.7, 25.8, 26.0, 26.1, 27.1, 27.9, 30.1, 31.56, 31.63, 39.5, 45.7, 51.3, 63.5, 82.0, 129.1, 140.2, 154.8, 168.3, 175.9 (not all aromatic carbons could be assigned).

IR (cm.$^{-1}$, KBr): 1730 ($CO_2R$) and 1638 (CONR).

MS (%): 511 (<1, parent), 295 (82), 195 (28), 185 (99), 161 (100), 57 (97).

HRMS calc'd for $C_{26}H_{37}N_3O_4F_3$: 512.2732. Found: 512.2751.

EXAMPLE 73

(1-t-Butoxycarbonylmethyl)-3-(3-tolylureido)-5,7-diphenylhexahydroazepin-2-one

Prepared from (1-t-butoxycarbonylmethyl)-3-amino-5,7-diphenyl-hexahydroazepin-2-one as in Example 60 as a foam in 6.3% yield.

$^1$H-NMR ($\delta$, $CDCl_3$): 1.2–1.4 (m, 2H), 1.29 (s, 9H), 2.0–2.2 and 2.4–2.6 (m, 2H), 2.25 (s, 3H), 3.21 (m, 1H), 3.60 ($AB_q$, $J_{AB}$=18, $\Delta v$=160 (2H), 5.15 (m, 1H), 5.22 (m, 1H), 6.8 and 7.0–7.4 (m, 16H).

IR (cm.$^{-1}$, KBr): 1723 ($CO_2R$) and 1638 (CONR).

MS (%): 527 (15, parent), 235 (30), 133 (100)

HRMS calc'd for $C_{32}H_{37}N_3O_4$: 527.2822. Found: 527.2742.

EXAMPLE 74

(1-t-Butoxycarbonylmethyl)-3-(3-tolylureido)-5-phenyl-7-benzylhexahydroazepin-2-one A. 2-Benzyl-4-phenylcyclohexanone Prepared in analogy with a procedure developed by Stork, G. and Dowd, S. J. Am. Chem. Soc., 85, 2178 (1963). To a 250 mL round-bottomed flask equipped with $N_2$ inlet, Dean-Stark trap, and condenser were added 8.71 g (50 mmol) 4-phenylcyclohexanone, 5.72 mL (50 mmol) cyclohexylamine, and 100 mL benzene. The solution was refluxed until water removal was complete (12 hours). Twenty mL of this solution, upon cooling, was added to 10.0 mL of a 1.0M solution of ethyl magnesium bromide in tetrahydrofuran, and the reaction heated to 60°–70° C. for 30 minutes. The solution was cooled, and 1.43 mL (12 mmol) benzyl bromide added, producing an immediate color change. The reaction was refluxed 3.5 hours, cooled, and evaporated. The residue was taken up in 40 mL 1N HCl, stirred at room temperature 18 hours, and extracted into ethyl acetate, which was washed with water and brine, dried over sodium sulfate, and evaporated. The crude yellow oil was used without further purification, 3.2 g (100%).

$^1$H-NMR (d, $CDCl_3$): 1.62 (m, 1H), 1.95 (m, 1H), 2.20 (m, 2H), 2.41 (dd, J=8.5, 14, 1H), 2.55 (m, 2H), 2.77 (m, 1H), 3.01 (m, 1H), 3.34 (dd, J=4, 14, 1H), 7.0–7.4 (m, 10H).

IR (cm.$^{-1}$, KBr): 1715 (C=O).

MS (%): 264 (parent, 38), 235 (10), 159 (16), 146 (28), 145 (26), 131 (31), 104 (35), 91 (100).

B. 5-Phenyl-7-benzylhexahydroazepin-2-one

To a 250 mL round-bottomed flask equipped with condenser and $N_2$ inlet were added 2.64 g (10 mmol) of 2-benzyl-4-phenylcyclohexanone, 1.70 g (15 mmol) hydroxylamine-O-sulfonic acid, and 50 mL formic acid. The reaction was refluxed 5.5 hours, cooled, and poured into 3N NaOH. The mixture was extracted into ethyl acetate, washed with brine, dried, and evaporated. The residue was chromatographed on silica gel using methanol/methylene chloride, collecting the product spot at $R_f$=0.30 as an oil, 1.8 g (64%).

¹H-NMR (d, CDCl₃): 1.6–2.0 (m, 4H), 2.57 (m, 1H), 2.7–2.9 (m, 4H), 3.76 (m, 1H), 5.6 and 5.75 (broad singlets, NH, 1H), 7.0–7.4 (m, 10H).

IR (cm.⁻¹, KBr): 1660 (C=O)

MS (%): 279 (parent, 13), 235 (24), 188 (40), 91 (100), 44 (31).

The remaining steps were carried out as described in Example 60:

C. 3-Bromo-5-phenyl-7-benzylhexahydroazepin-2-one

Oil, mixture of 4 diastereomers, 27% yield.

¹H-NMR (δ, CDCl₃): 1.7–3.2 (series of multiplets, 5H), 2.86 (m, 2H), 3.8 and 4.2 (multiplets, 1H), 4.58 and 4.88 (multiplets, 1H), 6.28, 6.55, 6.68 and 6.80 (broad singlets, N H, 1H), 7.0–7.4 (m, 10H).

¹³C-NMR (δ, CDCl₃): the 4 diastereomers gave many overlapping peaks; 3 of the 4 lactam carbonyls appeared at 170.35, 170.54, and 170.65.

IR (cm.⁻¹, KBr): 1670 (C=O).

MS (%): 358/360 (parent, Br⁷⁹/Br⁸¹ 2/2), 266/268 (98/100), 222 (20), 158 (45), 144 (53).

D. 1-(t-Butylcarbonylmethyl)-3-bromo-5-phenyl-7-benzylhexahydroazepin-2-one

Oil, mixture of 2 diastereomers in a 2/1 ratio, 97% yield.

¹H-NMR (d, CDCl₃): 1.44 and 1.45 (singlets, 9H), 1.8–4.3 (series of multiplets, 8H), 4.9 to 5.4 (multiplets, 1H), 7.0–7.4 (m, 10H).

IR (cm.⁻¹, KBr): 1745 and 1650 (C=O).

MS (%): 392 (parent-Br, 2), 372 (30), 255 (100), 200 (70), 180 (98).

E. 1-(t-Butylcarbonylmethyl)-3-azido-5-phenyl-7-benzylhexahydroazepin-2-one

Oil, mixture of 2 diastereomers in a 7/3 ratio, 87% yield.

¹H-NMR (δ, CDCl₃): 1.45 and 1.46 (singlets, 9H), 1.8–4.6 (series of multiplets, 9H), 7.0–7.4 (m, 10H).

IR (cm.⁻¹, KBr): 2107 (N₃), 1739 and 1659 (C=O).

MS (%): 406 (parent-N₂, 2), 350 (10), 259 (13), 91 (17), 57 (16), 32 (100).

F. 1-(t-Butylcarbonylmethyl)-3-amino-5-phenyl-7-benzylhexahydroazepin-2-one

Oil, predominantly one diastereomer, 67% yield.

¹H-NMR (δ, CDCl₃): 1.42 and 1.46 (singlets, 9H), 1.5–2.0 (m, 4H), 2.32 and 2.71 (multiplets, 1H), 3.08 (m, 2H), 3.25 (m, 1H), 4.1 (m, 1H), 4.10 (AB_q, J_{AB}=17, Δν=75), 7.0–7.4 (m, 10H).

¹³C-NMR (δ, CDCl₃): (one diastereomer) 28.1, 39.1, 39.3, 44.7, 51.8, 54.3, 55.4, 63.3, 81.6, 126.7, 126.9, 127.2, 128.5, 128.8, 137.3, 144.6, 169.1, 176.0.

MS (%): 409 (parent+1, 2), 262 (42), 132 (100), 91 (30).

G. (1-t-Butoxycarbonylmethyl)-3-(3-tolylureido)-5-phenyl-7-benzylhexahydroazepin-2-one 9% yield, M.P. 100°–110° C.

¹H-NMR (δ, CDCl₃): 1.41 (s, 9H), 1.5–3.2 (series of multiplets, 7H), 4.15 (AB_q, J_{AB}=17, Δν=139), 4.28 (m, 1H), 5.24 (m, 1H), 6.8 and 7.0–7.4 (m, 16H).

¹³C-NMR (δ, CDCl₃): 21.5, 28.0, 38.2, 39.3, 39.35, 39.4, 44.5, 50.4, 55.6, 81.9, 127.0, 127.3, 128.5, 128.6, 128.7, 128.9, 129.0, 136.7, 138.9, 144.4, 155.3, 168.6, 173.

IR (cm.⁻¹, KBr): 1740 (CO₂R) and 1640 (CONR).

MS (%): 541 (parent, 2), 261 (30), 132 (100), 91 (47).

Anal. calc'd for C₃₃H₃₉N₃O₄: C 73.17, H 7.26, N 7.76. Found: C 72.82, H 7.28, N 7.71.

EXAMPLE 75

(1-t-Butoxycarbonylmethyl)-3-(3-methoxyphenylureido)-5-phenyl-7-benzylhexahydro-azepin-2-one Prepared from the title compound of Example 74F in analogy with the procedure of Example 60, in 27% yield, M.P. 95°–105° C.

¹H-NMR (δ, CDCl₃): 1.40 (s, 9H), 1.5–3.2 (series of multiplets, 7H), 3.72 (s, 3H), 4.10 (AB_q, J_{AB}=17, Δν=135), 4.28 (m, 1H), 5.24 (m, 1H), 6.5, 6.8 and 7.0–7.6 (m, 16H).

¹³C-NMR (δ, CDCl₃): 28.0, 38.2, 39.2, 39.3, 39.4, 44.5, 50.4, 55.2, 55.7, 82.0, 105.4, 109.2, 112.2, 126.9, 127.0, 127.2, 127.3, 128.5, 128.6, 128.7, 128.9, 129.1, 129.2, 129.3, 129.5, 129.6, 136.7, 140.4, 144.4, 155.2, 160.2, 168.6, 172.9.

IR (cm.⁻¹, KBr): 1740 (CO₂R) and 1640 (CONR).

MS (%): 557 (parent, 1), 261 (35), 149 (100), 132 (98), 123 (53), 91 (52).

Anal. calc'd for C₃₃H₃₉N₃O₅: C 71.07, H 7.05, N 7.53. Found: C 71.30, H 7.10, N 7.34.

EXAMPLE 76

(1-t-Butoxycarbonylmethyl)-3-(3-chlorophenylureido)-5-phenyl-7-benzylhexahydroazepin-2-one Prepared from the title compound of Example 74F in analogy with the procedure of Example 60 in 33% yield, M.P. 95°–110° C.

¹H-NMR (δ, CDCl₃): 1.38 (s, 9H), 1.5–3.2 (series of multiplets, 7H), 4.10 (AB_q, J_{AB}=17, Δν=138), 4.38 (m, 1H), 5.28 (m, 1H), 6.8–7.8 (m, 16H).

¹³C-NMR (δ, CDCl₃): 28.0, 37.5, 39.1, 39.2, 39.5, 50.3, 55.7, 60.4, 82.1, 117.3, 119.4, 122.3, 122.4, 126.5, 126.7, 127.0, 127.1, 127.2, 128.5, 128.6, 128.8, 128.9, 129.2, 129.3, 129.7, 134.4, 136.6, 140.6, 144.2, 155.0, 168.5, 173.6.

IR (cm.⁻¹, KBr): 1740 (CO₂R) and 1640 (CONR).

MS (%): 562 (parent, 1), 261 (50), 153 (80), 132 (100), 91 (40).

HRMS calc'd for C₃₂H₃₇N₃O₄Cl: 562.24765. Found: 562.24970.

Anal. calc'd for C₃₂H₃₆N₃O₄Cl: C 68.38, H 6.46, N 7.48. Found: C 68.37, H 6.76, N 7.02 (−0.46).

EXAMPLE 77

(1-t-Butoxycarbonylmethyl)-3-(3-tolylureido)-5-phenyl-7-cyclohexylmethyl-hexahydroazepin-2-one Prepared from (1-t-butoxycarbonylmethyl)-3-amino-5-phenyl-7-cyclohexylmethylhexahydroazepin-2-one by a procedure analogous to that of Example 74 in 47% yield as a foam, mixture of diastereomers.

¹H-NMR (δ, CDCl₃): 1.37 (s, 9H), 0.8–2.3 and 2.64 (series of multiplets, 7H), 3.18 (m, 1H), 3.95 and 4.0 (AB_q's, J_{AB}=17 and 17, Δν=139 and 150), 4.0–4.1 (m, 1H), 5.12 and 5.23 (multiplets, 1H), 6.8 and 7.0–7.5 (m, 16H).

¹³C-NMR (δ, CDCl₃): (one diastereomer) 21.5, 26.1, 28.0, 33.3, 33.5, 34.6, 39.2, 39.3, 39.9, 41.5, 44.9, 46.0, 51.9, 54.2, 81.8, 117.1, 120.8, 123.6, 123.8, 126.3, 126.4, 126.9, 127.2, 128.5, 128.7, 138.7, 139.1, 144.8, 145.6, 155.1, 168.5, 173.3.

IR (cm.⁻¹, KBr): 1740 (CO₂R) and 1640 (CONR).

MS (%): 547 (parent, 1), 243 (15), 184 (50), 141 (30), 136 (100).

Anal. calc'd for C₃₃H₄₅N₃O₄: C 72.36, H 8.28, N 7.67. Found: C 72.21, H 8.35, N 7.44.

EXAMPLE 78

(1-t-Butoxycarbonylmethyl)-3-(3-tolylureido)-5-phenyl-7-cyclohexylhexahydroazepin-2-one Prepared from (1-t-butoxycarbonylmethyl-3-amino-5-phenyl-7-cyclohexylhexahydroazepin-2-one by a procedure analogous to that of Example 74 in 6% yield as a 3/1 mixture of diastereomers, foam.

$^1$H-NMR (δ, CDCl$_3$): 0.8–2.3 (m, 15H), 1.37 (s, 9H), 2.26 (s, 3H), 3.02 and 3.22 (multiplets, 1H), 3.6 (m, 1H), 4.01 and 4.1 (AB$_q$'s, J$_{AB}$=17 and 17, Δv=216 and 230, 2H), 4.92 and 5.13 (multiplets, 1H), 6.7–7.4 (m, 11H).

$^{13}$C-NMR (d, CDCl$_3$): (one diastereomer) 21.5, 25.86, 25.90, 26.1, 28.0, 31.5, 39.4, 39.9, 45.8, 46.6, 51.6, 63.1, 81.9, 117.2, 120.8, 120.9, 123.6, 123.8, 126.4, 126.9, 127.0, 128.5, 128.6, 128.7, 128.8, 138.8, 139.0, 145.9, 155.1, 168.2, 175.5.

IR (cm.$^{-1}$, KBr): 1730 (CO$_2$R) and 1640 (CONR).

MS (%): 533 (parent, 2), 240 (25), 133 (100), 107 (70), 91 (40).

HRMS calc'd for C$_{32}$H$_{43}$N$_3$O$_4$: 533.3243. Found: 533.32941.

EXAMPLE 79

(1-t-Butoxycarbonylmethyl)-3-(3-methoxyphenylureido)-5-phenyl-7-cyclohexyl-hexahydroazepin-2-one Prepared from (1-t-butoxycarbonylmethyl)-3-amino-5-phenyl-7-cyclohexylhexahydroazepin-2-one by a procedure analogous to that of Example 74 in 14% yield, as a mixture of diastereomers, foam.

$^1$H-NMR (δ, CDCl$_3$): 0.8–2.3 (m, 15H), 1.37 (s, 9H), 2.6 (m, 1H), 3.0–3.4 (m, 1H), 3.74 (s, 3H), 3.97 and 4.1 (AB$_q$'s, J$_{AB}$=17 and 17, Δv=213 and 240, 2H), 4.90 and 5.12 (multiplets, 1H), 6.5 and 6.8–7.4 (m, 11H).

$^{13}$C-NMR (δ, CDCl$_3$): (one diastereomer) 25.9, 26.3, 28.0, 31.0, 34.9, 42.5, 45.8, 46.6, 51.5, 55.2, 63.1, 64.7, 81.8, 109.0, 126.2, 126.3, 126.9, 127.0, 128.5, 128.6, 129.5, 129.6, 140.5, 145.9, 147.1, 154.9, 160.2, 168.3, 175.4

IR (cm.$^{-1}$, KBr): 1730 (CO$_2$R) and 1640 (CONR).

MS (%): 549 (parent, 3.5), 344 (25), 240 (30), 149 (60), 132 (100).

HRMS calc'd for C$_{32}$H$_{43}$N$_3$O$_4$: 549.3192. Found: 549.33256.

EXAMPLE 80 cis-1-(t-Butylacetamido)-3-(3-tolylureido)-5-phenyl-7-(4-fluorophenyl)hexahydroazepin-2-one Prepared from cis-1-(t-butylacetamido)-3-amino-5-phenyl-7-(4-fluorophenyl)-hexahydroazepin-2-one by a procedure analogous to that of Example 60 in 63% yield, M.P. 228°–232° C.

$^1$H-NMR (δ, CD$_3$SOCD$_3$): 1.16 (singlet, 9H), 2.0 (m, 3H), 2.24 (s, 3H), 2.5 (m, 1H), 3.1–3.9 (multipliers, 3H), 5.10 (m, 1H), 5.34 (m, 1H), 6.6–7.5 (m, 14H), 8.95 (bs, 1H).

$^{13}$C-NMR (δ, CD$_3$SOCD$_3$): 21.3, 28.4, 45.0, 50.0, 51.6, 58.5, 114.7, 115.1, 115.4, 118.1, 121.8, 122.4, 126.3, 126.8, 128.5, 131.6, 131.7, 135.5, 137.8, 140.5, 146.2, 154.1, 167.2, 173.4.

IR (cm.$^{-1}$, KBr): 1660 (broad, C=O).

FAB MS (%): 545 (parent+1, 43), 472 (36), 412 (37), 254 (27), 211 (100).

Anal. calc'd for C$_{32}$H$_{37}$N$_4$O$_3$F·3/4H$_2$O: C 68.86, H 6.95, N 10.04. Found: C 68.87, H 6.86, N 9.69.

EXAMPLE 81 cis-1-(t-Butylacetamido)-3-(3-methoxyphenylureido)-5-phenyl-7-(4-fluorophenyl)-hexahydroazepin-2-one Prepared from cis-1-(t-butylacetamido)-3-amino-5-phenyl-7-(4-fluorophenyl)-hexahydroazepin-2-one by a procedure analogous to that of Example 60 in 54% yield, M.P. 22.5°–227° C.

$^1$H-NMR (δ, CD$_3$SOCD$_3$): 1.16 (singlet, 9H), 2.0 (m, 3H), 2.6 (m, 1H), 3.2–3.9 (m, 3H), 3.70 (s, 3H), 5.10 (m, 1H), 5.32 (m, 1H), 6.5 and 6.8–7.5 (m, 14H), 9.05 (bs, 1H).

$^{13}$C-NMR (δ, CD$_3$SOCD$_3$): 28.4, 44.9, 46.8, 50.0, 51.5, 54.9, 58.5, 103.2, 106.5, 109.9, 115.1, 115.4, 126.3, 126.8, 128.5, 129.4, 131.6, 141.8, 146.1, 154.1, 159.7, 167.2, 173.3.

IR (cm.$^{-1}$, KBr): 1660 (broad, C=O).

FAB MS (%): 561 (parent+1, 25), 488 (30), 412 (28), 254 (27), 211 (100).

Anal. calc'd for C$_{32}$H$_{37}$N$_4$O$_4$·H$_2$O: C 66.42, H 6.79, N 9.68. Found: C 66.36, H 6.57, N 9.42.

EXAMPLE 82 cis-1-(t-Butylacetamido)-3-(3-chlorophenylureido)-5-phenyl-7-(4-fluorophenyl)-hexahydroazepin-2-one Prepared from cis-1-(t-butylacetamido)-3-amino-5-phenyl-7-(4-fluorophenyl)hexahydroazepin-2-one by a procedure analogous to Example 60 in 44% yield, M.P. 175°–178° C.

$^1$H-NMR (δ, CD$_3$SOCD$_3$): 1.16 (singlet, 9H), 2.0 (m, 3H), 2.6 (m, 1H), 3.2–3.9 (m, 3H), 5.10 (m, 1H), 5.32 (m, 1H), 6.8–7.6 (m, 14H), 9.27 (bs, 1H).

$^{13}$C-NMR (δ, CDCl$_3$): 28.45, 44.9, 46.8, 50.0, 51.6, 58.5, 115.1, 115.4, 115.8, 116.8, 120.7, 126.4, 126.8, 128.6, 130.3, 131.6, 131.7, 133.2, 135.4, 142.1, 146.1, 153.9, 167.2, 173.2.

IR (cm.$^{-1}$, KBr): 1660 (broad, C=O).

FAB MS (%): 565 (parent, 20), 492 (26), 412 (27), 254 (20), 211 (100).

Anal. calc'd for C$_{31}$H$_{34}$N$_4$O$_3$FCl·2H$_2$O: C 61.94, H 6.37, N 9.32. Found: C 61.93, H 5.73 (−0.64), N 9.09.

HRMS calc'd for C$_{31}$H$_{34}$N$_4$O$_3$FCl: 564.2790. Found: 564.23444.

EXAMPLE 83 cis-1-(t-Butylacetamido)-3-(3-tolylureido)-5-phenyl-7-(4-chlorophenyl)hexahydroazepin-2-one Prepared from cis-1-(t-butylacetamido)-3-amino-5-phenyl-7-(4-chlorophenyl)hexahydroazepin-2-one by a procedure analogous to that of Example 60 in 69% yield, M.P. 224°–226° C.

$^1$H-NMR (δ, CDCl$_3$, TFA): 1.20 (singlet, 9H), 2.0 (m, 1H), 2.3 (m, 3H), 2.33 (s, 3H), 3.30 (m, 1H), 3.98 (AB$_q$, J$_{AB}$=16, Δv=43, 2H), 5.27 (m, 1H), 5.38 (d, J=11, 1H), 6.69 (d, J=7, 1H), 6.9–7.5 (m, 16H).

$^{13}$C-NMR (δ, CDCl$_3$, TFA): 22.0, 27.9, 38.5, 38.8, 45.6, 52.8, 61.0, 112.4, 116.1, 119.9, 126.6, 127.3, 128.9, 129.5, 129.8, 130.8, 134.9, 143.6, 158, 176.

IR (cm.$^{-1}$, KBr): 1660 (broad, C=O).

FAB MS (%): 561 (parent+1, 47), 488 (30), 454 (20), 428 (25), 227 (28), 157 (100), 119 (46).

Anal. calc'd for C$_{32}$H$_{37}$N$_4$O$_3$Cl·1/2H$_2$O: C 67.41, H 6.72, N 9.83. Found: C 67.77, H 6.57, N 9.44.

EXAMPLE 84 cis-1-(t-Butylacetamido)-3-(3-methoxyphenylureido)-5-phenyl-7-(4-chlorophenyl)-hexahydroazepin-2-one Prepared from cis-1-(t-butylacetamido)-3-amino-5-phenyl-7-(4-chlorophenyl)hexahydroazepin-2-one by a procedure analogous to that of Example 60 in 33% yield, M.P. 130°–132° C.

¹H-NMR (δ, CDCl₃, TFA): 1.21 (singlet, 9H), 2.0–2.4 (multiplets, 4H), 3.29 (m, 1H), 3.82 (s, 3H), 3.89 (AB$_q$, J$_{AB}$=16, Δν=77, 2H), 5.24 (m, 1H), 5.39 (d, J=11, 1H), 6.7–6.9 and 7.1–7.4 (m, 16H).

¹³C-NMR (δ, CDCl₃, TFA): 28.0, 38.7, 38.9, 45.6, 48.3, 52.6, 52.8, 55.5, 60.8, 126.6, 127.3, 128.9, 129.5, 130.4, 130.5, 130.8, 135.1, 135.6, 143.8, 160.2, 168.8, 175.7.

IR (cm.⁻¹, KBr): 1660 (broad, C=O).

FAB MS (%): 577 (parent, 82), 504 (61), 428 (56), 227 (76), 119 (100), 103 (55).

Anal. calc'd for C₃₂H₃₇N₄O₄Cl: C 66.60, H 6.46, N 9.71. Found: C 66.83, H 6.46, N 9.51.

EXAMPLE 85 cis-1-(t-Butylacetamido)-3-(3-chlorophenylureido)-5-phenyl-7-(4-chlorophenyl)hexa-hydroazepin-2-one Prepared in analogy with Example 60 in 52% yield, M.P. 229°–231° C.

¹H-NMR (δ, CDCl₃, TFA): 1.21 (singlet, 9H), 2.0–2.4 (multiplets, 4H), 3.29 (m, 1H), 3.92 (AB$_q$, J$_{AB}$=16, Δν=65, 2H), 5.27 (d, J=8, 1H), 5.43 (d, J=10, 1H), 7.1–7.5 (m, 16H).

¹³C-NMR (δ, CDCl₃, TFA): 22.0, 27.9, 38.7, 45.6, 48.3, 52.5, 60.9, 71.3, 126.1, 126.6, 127.3, 128.9, 129.5, 130.6, 130.8, 134.9, 135.3, 135.7, 143.7, 176.0.

IR (cm.⁻¹, KBr): 1660 (broad, C=O).

FAB MS (%): 581 (parent+1, 63), 508 (61), 428 (36), 227 (65), 157 (81), 119 (100).

Anal. calc'd for C₃₁H₃₄N₄O₃Cl₂·1/3H₂O: C 63.37, H 5.95, N 9.54. Found: C 63.74, H 5.99, N 8.87 (−0.67).

HRMS calc'd for C₃₁H₃₄N₄O₃Cl₂: 580.2008. Found: 580.19940.

EXAMPLE 86 cis-1-(t-Butylacetamido)-3-(3-tolylureido)-5-phenyl-7-(4-tolyl)hexahydroazepin-2-one Prepared from cis-1-(t-butylacetamido)-3-amino-5-phenyl-7-(4-tolyl)hexahydroazepin-2-one by a procedure analogous to that of Example 60 in 57% yield, M.P. 216°–218° C.

¹H-NMR (δ, CDCl₃, TFA): 1.20 (singlet, 9H), 2.0–2.4 (multiplets, 4H), 2.33 (s, 3H), 2.34 (s, 3H), 3.27 (m, 1H), 3.96 (AB$_q$, J$_{AB}$=16, Δν=62, 2H), 5.22 (d, J=10, 1H), 5.39 (d, J=10, 1H), 7.0–7.4 (m, 16H).

¹³C-NMR (δ, CDCl₃, TFA): 20.9, 22.0, 27.9, 38.5, 38.9, 45.7, 48.2, 52.8, 61.5, 71.3, 120.8, 124.5, 126.6, 127.2, 128.0, 128.9, 129.3, 129.8, 130.0, 133.4, 134.7, 139.7, 140.4, 143.9, 176.

IR (cm.⁻¹, KBr): 1660 (broad, C=O).

FAB MS (%): 541 (parent+1, 10), 207 (12), 157 (100), 119 (24), 103 (12).

Anal. calc'd for C₃₃H₄₀N₄O₃: C 73.30, H 7.46, N 10.36. Found: C 72.90, H 7.37, N 10.11.

EXAMPLE 87 cis-1-(t-Butylacetamido)-3-(3-methoxyphenylureido)-5-phenyl-7-(4-tolyl)hexahydroazepin-2-one Prepared from cis-1-(t-butylacetamido)-3-amino-5-phenyl-7-(4-tolyl)hexahydroazepin-2-one by a procedure analogous to that of Example 60 in 40% yield as an amorphous solid.

¹H-NMR (δ, CDCl₃, TFA): 1.19 (singlet, 9H), 2.0–2.4 (multiplets, 4H), 2.34 (s, 3H), 3.29 (m, 1H), 3.83 (s, 3H), 3.95 (AB$_q$, J$_{AB}$=16, Δν=81, 2H), 5.22 (d, J=11, 1H), 5.40 (d, J=11, 1H), 6.8 and 7.1–7.4 (m, 16H).

¹³C-NMR (δ, CDCl₃, TFA): 22.0, 27.9, 38.6, 38.9, 45.6, 48.2, 52.7, 55.5, 61.4, 71.2, 126.2, 126.6, 127.2, 128.9, 129.3, 130.0, 130.5, 130.6, 133.4, 139.7, 143.9, 157.2, 169.4, 175.8.

IR (cm.⁻¹, KBr): 1660 (broad, C=O).

FAB MS (%): 557 (parent+1, 59), 484 (45), 408 (43), 250 (32), 207 (100), 132 (33), 105 (43).

Anal. calc'd for C₃₃H₄₀N₄O₄·H₂O: C 68.97, H 7.37, N 9.75. Found: C 68.97, H 7.38, N 9.60.

EXAMPLE 88 cis-1-(t-Butylacetamido)-3-(3-3-chlorophenylureido)-5-phenyl-7-(4-tolyl)hexahydroazepin-2-one Prepared from cis-1-(t-butylacetamido)-3-amino-5-phenyl-7-(4-tolyl)hexahydroazepin-2-one by a procedure analogous to that of Example 60 in 41% yield as an amorphous solid.

¹H-NMR (δ, CDCl₃, TFA): 1.20 (singlet, 9H), 2.0–2.4 (multiplets, 4H), 2.34 (s, 3H), 3.29 (m, 1H), 3.94 (AB$_q$, J$_{AB}$=16, Δν=58, 2H), 5.23 (d, J=9, 1H), 5.42 (d, J=11, 1H), 7.1–7.5 (m, 16H).

¹³C-NMR (δ, CDCl₃, TFA): 21.0, 27.9, 38.8, 38.9, 45.7, 48.2, 52.5, 61.4, 64.6, 122.2, 125.7, 126.6, 127.2, 128.9, 129.3, 130.0, 130.5, 133.5, 135.2, 137.4, 139.7, 144.0, 156.4, 169.3, 176.0.

IR (cm⁻¹, KBr): 1660 (broad, C=O).

FAB MS (%): 561 (parent+1, 44), 488 (34), 408 (28), 207 (67), 157 (100).

Anal. calc'd for C₃₂H₃₇N₄O₃Cl·1/4H₂O: C 67.95, H 6.68, N 9.91. Found: C 68.12, H 6.47, N 9.52.

EXAMPLE 89 cis-1-(t-Butylacetamido)-3-(3-tolylureido)-5-phenyl-7-(3-tolyl)hexahydroazepin-2-one Prepared from cis-1-(t-butylacetamido)-3-amino-5-phenyl-7-(3-tolyl)hexahydroazepin-2-one by a procedure analogous to that of Example 60 in 56% yield, M.P. 252°–254° C.

¹H-NMR (δ, CDCl₃, TFA): 1.20 (singlet, 9H), 2.0–2.4 (multiplets, 4H), 2.32 (s, 3H), 2.33 (s, 3H), 3.27 (m, 1H), 3.93 (AB$_q$, J$_{AB}$=16, Δν=54, 2H), 5.20 (d, J=9, 1H), 5.38 (d, J=11, 1H), 7.0–7.5 (m, 16H).

¹³C-NMR (δ, CDCl₃, TFA): 21.1, 21.2, 28.0, 38.7, 39.0, 45.8, 48.3, 52.6, 61.6, 120.4, 124.2, 126.4, 126.7, 127.2, 127.5, 128.9, 129.2, 129.7, 130.1, 130.2, 135.3, 136.5, 139.2, 140.2, 144.0, 158, 169, 175.6.

IR (cm.⁻, KBr): 1660 (broad, C=O).

FAB MS (%): 541 (parent+1, 72), 468 (63), 408 (45), 250 (32), 207 (100), 157 (100), 119 (68).

Anal. calc'd for C₃₃H₄₀N₄O₃: C 73.30, H 7.46, N 10.36. Found: C 73.02, H 7.39, N 10.30.

EXAMPLE 90 cis-1-(t-Butylacetamido)-3-(3-methoxyphenylureido)-5-phenyl-7-(3-tolyl)hexahydroazepin-2-one Prepared from cis-1-(t-butylacetamido)-3-amino-5-phenyl-7-(3-tolyl)hexahydroazepin-2-one by a procedure analogous to that of Example 60 in 76.5% yield as an amorphous solid.

¹H-NMR (δ, CDCl₃, TFA): 1.19 (singlet, 9H), 2.0–2.4 (multiplets, 4H), 2.32 (s, 3H), 3.28 (m, 1H), 3.81 (s, 3H), 4.0 (m, 2H), 5.21 (d, J=9, 1H), 5.39 (d, J=11, 1H), 6.7–6.9 and 7.1–7.4 (m, 16H).

¹³C-NMR (δ, CDCl₃, TFA): 21.2, 28.0, 38.8, 39.1, 45.7, 48.2, 52.6, 55.4, 61.6, 71.0, 126.4, 126.7, 127.2, 128.9, 129.2, 130.1, 130.5, 136.6, 139.2, 144.1, 157, 169, 176.

IR (cm.⁻¹, KBr): 1660 (broad, C=O)

FAB MS (%): 557 (parent+1, 34), 484 (39), 408 (32), 207 (75), 119 (100), 103 (100).

Anal. calc'd for $C_{33}H_{40}N_4O_4 \cdot H_2O$: C 68.97, H 7.37, N 9.75. Found: C 68.73, H 7.95 (−0.58), N 9.42.

EXAMPLE 91 cis-1-(t-Butylacetamido)-3-(3-chlorophenylureido)-5-phenyl-7-(3-tolyl)hexahydroazepin-2-one Prepared from cis-1-(t-butylacetamido)-3-amino-5-phenyl-7-(3-tolyl)hexahydroazepin-2-one by a procedure analogous to that of Example 60 in 65% yield as an amorphous solid.

¹H-NMR (δ, CDCl₃, TFA): 1.20 (singlet, 9H), 2.0–2.4 (multiplets, 4H), 2.33 (s, 3H), 3.29 (m, 1H), 3.95 (AB$_q$, J$_{AB}$=16, Δν=58, 2H), 5.22 (d, J=9, 1H), 5.44 (d, J=11, 1H), 7.1–7.4 (m, 16H).

¹³C-NMR (δ, CDCl₃, TFA): 21.2, 28.0, 38.8, 39.0, 45.7, 48.2, 52.5, 61.7, 71.1, 125.6, 126.3, 126.7, 127.2, 128.9, 129.2, 130.2, 130.5, 135.2, 136.5, 139.2, 144.0, 157, 169, 176.

IR (cm.⁻¹, KBr): 1660 (broad, C=O).

FAB MS (%): 561 (parent+1, 30), 488 (75), 408 (43), 250 (37), 207 (100), 115 (39).

Anal. calc'd for $C_{32}H_{37}N_4O_3Cl \cdot 1/4H_2O$: C 67.95, H 6.68, N 9.91. Found: C 67.89, H 6.72, N 9.91.

EXAMPLE 92

1-(t-Butylacetamido)-3-(2-methylphenylureido)-5,7-diphenylhexahydroazepin-2-one

Prepared from the more polar amine diastereomer of 1-(t-butylacetamido)-3-amino-5,7-diphenyl-hexahydroazepin-2-one in Example 60 in 26% yield, mp 145°–153° C.

¹H-NMR (δ, CD₃SOCD₃): 1.15 (singlet, 9H), 1.9–2.1 (m, 3H), 2.17 (s, 3H), 2.61 (m, 1H), 3.25 (m, 1H), 3.51 (AB$_q$, J$_{AB}$=16, Δν=214, 2H), 5.10 (m, 1H), 5.30 (d, J=10, 1H), 6.8–7.4 (m, 15H), 7.77 (d, J=8, 1H), 8.17 (s, 1H).

¹³C-NMR (δ, CD₃SOCD₃): 22.8, 28.5, 45.0, 47.0, 49.9, 51.8, 59.4, 67.3, 120.9, 121.0, 122.0, 125.9, 126.0, 126.3, 126.7, 126.8, 127.2, 128.0, 128.4, 128.5, 128.7, 129.4, 129.5, 130.1, 131.3, 138.2, 139.3, 146.3, 154.4, 167.3, 173.4.

IR (cm⁻¹, KBr): 1650 (broad, C=O)

FAB MS (%): 527 (parent+1, 90), 454 (75), 394 (45), 193 (100), 157 (67), 119 (54), 91 (66).

Anal. Calc'd. for $C_{32}H_{38}N_4O_3 \cdot 1/2H_2O$: C 71.75, H 7.34, N 10.46. Found: C 71.84, H 7.10, N 10.27.

EXAMPLE 93

1-(t-Butylacetamido)-3-(4-chlorophenylureido)-5,7-diphenylhexahydroazepin-2-one

Prepared from the more polar amine diastereomer of 1-(t-butylacetamido)-3-amino-5,7-diphenyl-hexahydroazepin-2-one in Example 60 in 19% yield, mp 165°–170° C.

¹H-NMR (δ, CDCl₃, TFA): 1.18 (singlet, 9H), 2.03 (m, 1H), 2.2–2.4 (m, 2H), 3.28 (m, 1H), 4.03 (AB$_q$, J$_{AB}$=17, Dn=132, 2H), 5.26 (δ, J=9, 1H), 5.43 (δ, J=11, 1H), 7.1–7.4 (m, 17H).

¹³C-NMR (δ, CDCl₃, TFA): 27.7, 38.5, 38.6, 45.7, 48.1, 52.9, 53.7, 61.9, 71.6, 124.7, 126.5, 127.3, 128.7, 128.9, 129.0, 129.4, 129.6, 129.7, 129.8, 130.0, 133.6, 136.2, 143.6, 157.4, 169.8, 176.3.

IR (cm.⁻¹, KBr): 1650 (broad, C=O)

FAB MS (%): 547 (parent+1, 23), 474 (22), 420 (15), 394 (16), 193 (28), 155 (45), 136 (30), 119 (100), 104 (40).

Anal. Calc'd. for $C_{31}H_{35}N_4O_3Cl \cdot 1/2H_2O$: C 66.96, H 6.52, N 10.07. Found: C 66.65, H 6.33, N 9.86.

EXAMPLE 94

1-(t-Butylacetamido)-3-(5-(benztriazolyl)ureido)-5,7-diphenylhexahydroazepin-2-one To a 35 mL round-bottomed flask equipped with N₂ inlet and condenser were added 62 mg (0.382 mmol) benztriazole-5-carboxylic acid, 5 mL dry tetrahydrofuran, 0.090 mL (0.420 mmol) diphenylphosphoryl azide, and 0.060 mL (0.420 mmol) triethylamine. The reaction was refluxed for 1 hr, cooled briefly, and 150 mg (0.382 mmol) of 1-(t-butylacetamido)-3-amino-5,7-diphenylhexahydroazepin-2-one (the more polar amine diastereomer in Example 60) was added and refluxing continued for 14 hr. The reaction was cooled, filtered to remove a small amount of amide byproduct that had formed, and the filtrate evaporated. The residue was triturated with chloroform to afford a white solid, 70 mg (34%), mp 210°–220° C.

¹H-NMR (δ, CDCl₃): 1.16 (singlet, 9H), 2.03 (m, 1H), 2.2–2.5 (m, 3H), 3.18 (m, 1H), 3.28 (m, 1H), 4.01 (AB$_q$, J$_{AB}$=16, Dn=108, 2H), 5.2–5.3 (m, 2H), 5.64 (bs, 1H), 7.1–7.4 (m, 13H), 7.92 (d, J=9, 1H), 8.06 (s, 1H), 8.38 (s, 1H).

¹³C-NMR (δ, CDCl₃): 27.9, 38.6, 39.0, 45.6, 48.0, 52.5, 53.4, 61.8, 116.1, 119.9, 125.2, 126.5, 127.4, 128.9, 129.5, 129.7, 129.9, 130.5, 135.0, 136.3, 140.9, 143.7, 155.1, 163.0, 169.2, 175.8.

IR (cm.⁻¹, KBr): 1640 (broad, C=O)

FAB MS (%): 555 (parent+1, 64), 481 (70), 394 (35), 193 (83), 155 (55), 119 (100).

HRMS: Calc'd. for $C_{31}H_{36}N_7O_3$: 554.2872. Found: 554.28607.

EXAMPLE 95

1-(t-Butylacetamido)-3-(3,4-dimethylphenylureido)-5,7-diphenylhexahydroazepin-2-one Prepared as in Example 94, using the more polar isomer of 1-(t-butylacetamido)-3-amino-5,7-diphenylhexahydroazepin-2-one described in Example 60, in 48% yield, mp 185°–188° C.

¹H-NMR (δ, CDCl₃): 1.19 (singlet, 9H), 2.0 (m, 1H), 2.14 (s, 3H), 2.15 (s, 3H), 2.2–2.3 (m, 2H), 2.55 (m, 1H), 3.20 (m, 1H), 3.59 (AB$_q$, J$_{AB}$=16, Dn=193, 2H), 5.16 (d, J=10, 1H), 5.24 (dd, J=7,10, 1H), 5.38 (s, 1H), 6.71 (d, J=6, 1H), 7.0–7.4 (m, 13H), 7.53 (bs, 1H).

¹³C-NMR (δ, CDCl₃): 19.0, 19.9, 28.6, 39.3, 39.4, 46.1, 48.2, 51.1, 52.2, 61.2, 117.9, 121.8, 121.9, 126.5, 126.6, 127.0, 128.5, 128.6, 128.8, 128.9, 129.4, 129.5, 130.0, 136.8, 137.1, 138.2, 145.3, 155.4, 167.5, 175.0.

IR (cm.⁻¹, KBr): 1660 (broad, C=O).

FAB MS (%): 541 (48, parent+1), 468 (35), 394 (32), 309 (39), 193 (42), 155 9100), 135 (72), 119 (100), 103 (96).

Anal. Calc'd. for $C_{33}H_{40}N_4O_3$: C 73.30, H 7.46, N 10.36. Found: C 73.09, H 7.32, N 10.08.

EXAMPLE 96

1-(t-Butylacetamido)-3-(3-dimethylaminophenylureido)-5,7-diphenyl-hexahydroazepin-2-one Prepared as in Example 94, using the more polar isomer of 1-(t-butylacetamido)-3-amino-5,7-diphenyl-hexahydroazepin-2-one described in Example 60, in 71% yield, mp 145°–153° C.

$^1$H-NMR ($\delta$, CDCl$_3$): 1.18 (singlet, 9H), 1.98 (m, 1H), 2.22 (m, 2H), 2.57 (m, 1H), 2.87 (s, 6H), 3.20 (m, 1H), 3.58 (AB$_q$, J$_{AB}$=16, Dn=174, 2H), 5.17 (d, J=10, 1H), 5.26 (m, 1H), 5.42 (s, 1H), 6.3, 6.6, 6.7, 6.9, and 7.0–7.3 (m, 16H), 7.59 (s, 1H).

$^{13}$C-NMR ($\delta$, CDCl$_3$): 28.6, 39.4, 39.5, 40.6, 46.0, 48.3, 51.1, 52.1, 61.2, 104.5, 107.7, 108.5, 108.6, 126.6, 127.0, 128.6, 128.8, 128.9, 129.1, 129.3, 129.5, 138.3, 140.1, 145.3, 151.5, 155.3, 167.5, 174.9.

IR (cm.$^{-1}$, KBr): 1640 (broad, C=O).

Anal. Calc'd. for $C_{33}H_{41}N_5O_3$·1/2H$_2$O: C 70.19, H 7.50, N 12.40. Found: C 69.81, H 7.13, N 12.05.

The hydrochloride salt was formed using HCl in ether and crystallized from acetone to afford a white solid, mp 190°–197° C.

Anal. Calc'd. for $C_{33}H_{41}N_5O_3$·HCl: C 66.93, H 7.15, N 11.83. Found: C 66.60, H 7.17, N 11.70.

EXAMPLE 97 cis-1-(t-Butylacetamido)-3-(3-tolylureido)-5-phenyl-7-(3-methoxyphenyl)hexahydroazepin-2-one Prepared from the more polar isomer of 1-(t-butylacetamido)-3-amino-5-phenyl-7-(3-methoxyphenyl) hexahydroazepin-2-one in analogy with Example 60 in 40% yield, mp 245°–247° C.

$^1$H-NMR ($\delta$, CDCl$_3$, TFA): 1.19 (singlet, 9H), 1.9–2.4 (multiplets, 4H), 2.33 (s, 3H), 3.28 (m, 1H), 3.81 (s, 3H), 3.97 (AB$_q$, J$_{AB}$=17, Dn York=62, 2H), 5.23 (d, J=10, 1H), 5.38 (d, J=11, 1H), 6.8–7.4 (m, 16H).

$^{13}$C-NMR ($\delta$, CDCl$_3$, TFA): 21.0, 27.9, 38.6, 38.8, 45.6, 48.2, 52.8, 52.9, 55.5, 61.6, 114.7, 115.9, 121.9, 124.5, 126.6, 127.3, 128.0, 128.9, 129.7, 130.5, 138.0, 140.3, 143.8, 158, 169, 175.6.

IR (cm.$^{-1}$, KBr): 1650 (broad, C=O)

FAB MS (%): 557 (parent+1, 30), 484 (45), 266 930), 223 (100), 132 (45), 115 (42), 91 (44).

Anal. Calc'd. for $C_{33}H_{40}N_4O_4$: C 71.20, H 7.24, N 10.07. Found: C 70.98, H 7.51, N 9.83.

EXAMPLE 98 cis-1-(t-Butylacetamido)-3-(3-methoxyphenylureido)-5-phenyl-7-(3-methoxyphenyl)hexahydroazepin-2-one Prepared from the more polar isomer of 1-(t-butylacetamido)-3-amino-5-phenyl-7-(3-methoxyphenyl) hexahydroazepin-2-one in analogy with Example 60 in 46% yield as an amorphous solid.

$^1$H-NMR ($\delta$, CDCl$_3$, TFA): 1.19 (singlet, 9H), 2.0–2.4 (multiplets, 4H), 3.29 (m, 1H), 3.80 (s, 3H), 3.82 (s, 3H), 3.8–3.9 and 4.0–4.1 (m, 2H), 5.25 (m, 1H), 5.38 (m, 1H), 6.7–7.0 and 7.1–7.4 (m, 16H).

$^{13}$C-NMR ($\delta$, CDCl$_3$, TFA): 22.1, 28.0, 38.7, 38.8, 45.6, 47, 52, 55.4, 55.5, 61.5, 114.6, 115.8, 121.7, 126.6, 127.2, 128.9, 130.5, 143.9 (remaining carbons not visible in this scan).

IR (cm.$^{-1}$, KBr): 1670, 1630, 1600 (broad, C=O).

FAB MS (%): 573 (parent+1, 45), 500 (52), 424 (35), 266 (34), 223 (100), 132 (32), 115 (48), 91 (37).

Anal. Calc'd. for $C_{33}H_{40}N_4O_5$·H$_2$O: C 67.10, H 7.17, N 9.48. Found: C 67.01, H 7.23, N 9.20.

EXAMPLE 99 cis-1-(t-Butylacetamido)-3-(3-chlorophenylureido)-5-phenyl-7-(3-methoxyphenyl)hexahydroazepin-2-one Prepared from the more polar isomer of 1-(t-butylacetamido)-3-amino-5-phenyl-7-(3-methoxyphenyl) hexahydroazepin-2-one in analogy with Example 60 in 31% yield as an amorphous solid.

$^1$H-NMR ($\delta$, CDCl$_3$, TFA): 1.20 (singlet, 9H), 2.0–2.4 (multiplets, 4H), 2.33 (s, 3H), 3.29 (m, 1H), 3.81 (s, 3H), 3.96 (AB$_q$, J$_{AB}$=17, Dn=59, 2H), 5.24 (d, J=9, 1H), 5.42 (d, J=11, 1H), 6.8–7.4 (m, 16H).

$^{13}$C-NMR ($\delta$, CDCl$_3$, TFA): 22, 28.0, 38.7, 38.8, 45.6, 48.2, 52.5, 55.4, 61.6, 114.7, 115.9, 121.8, 125.8, 126.6, 127.2, 128.9, 130.5, 130.6, 138.1, 143.9, 156, 167, 175.

IR (cm.$^{-1}$, KBr): 1670, 1620 (broad, C=O).

FAB MS (%): 577 (parent+1, 35), 504 (46), 223 (100), 157 (73), 119 (51).

Anal. Calc'd. for $C_{32}H_{37}N_4O_4$Cl·H$_2$O: C 64.58, H 6.60, N 9.41. Found: C 67.54, H 6.63, N 9.24.

EXAMPLE 100 cis-1-(t-Butylacetamido)-3-(3-tolylureido)-5-phenyl-7-(4-trifluoromethylphenyl)hexahydroazepin-2-one Prepared from the more polar isomer of 1-(t-butylacetamido)-3-amino-5-phenyl-7-(4-trifluoromethylphenyl)hexahydroazepin-2-one in analogy with Example 60 in 10% yield as an amorphous solid.

$^1$H-NMR ($\delta$, CDCl$_3$, TFA): 1.19 (singlet, 9H), 2.0–2.4 (multiplets, 4H), 2.34 (s, 3H), 3.31 (m, 1H), 3.82 (AB$_q$, J$_{AB}$=16, Dn=36, 2H), 4.82 and 5.02 (m, 1H), 5.3 (m, 1H), 7.0–7.7 (m, 16H).

$^{13}$C-NMR ($\delta$, CDCl$_3$, TFA): 21.1, 28.0, 38.6, 38.8, 43.3, 45.6, 48.4, 52.7, 61.0, 120.7, 121.2, 124.4, 125.0, 126.2, 126.5, 126.6, 126.9, 127.3, 127.7, 128.2, 128.9, 129.7, 130.0, 131.5, 131.9, 134.8, 135.0, 140.3, 140.5, 143.7, 143.9, 158, 168, 175.

IR (cm.$^{-1}$, KBr): 1680, 1660, 1640 (broad, C=O).

FAB MS (%): 595 (parent+1, 5), 482 (24), 349 (30), 157 (100), 135 (45), 119 (99), 103 (51).

Anal. Calc'd. for $C_{33}H_{37}N_4O_3F_3$·3/2H$_2$O: C 63.75, H 6.49, N 9.01. Found: C 64.01, H 6.44, N 8.74.

EXAMPLE 101 cis-1-(t-Butylacetamido)-3-(3-methoxyphenylureido)-5-phenyl-7-(4-trifluoromethylphenyl)hexahydroazepin-2-one Prepared from the more polar isomer of 1-(t-butylacetamido)-3-amino-5-phenyl-7-(4- trifluoromethylphenyl)hexahydroazepin-2-one in analogy with Example 60 in 48% yield as an amorphous solid.

$^1$H-NMR ($\delta$, CDCl$_3$, TFA): 1.18 (singlet, 9H), 2.0–2.4 (multiplets, 4H), 3.31 (m, 1H), 3.82 (s, 3H), 3.83 (AB$_q$, J$_{AB}$=16, Dn=37, 2H), 4.82 and 5.02 (m, 1H), 5.3–5.4 (m, 1H), 6.7–7.7 (m, 16H).

$^{13}$C-NMR ($\delta$, CDCl$_3$, TFA): 22.1, 28.0, 38.5, 38.7, 43.3, 45.6, 48.4, 55.5, 60.9, 126.2, 126.5, 126.6, 126.9, 127.3, 128.9, 130.1, 130.6, 130.8, 140.5, 143.7, 144.0, 157, 168, 176.

IR (cm.$^{-1}$, KBr): 1660, 1640, 1600 (broad, C=O).

FAB MS (%): 611 (parent+1, 4), 498 (17), 349 (20), 157 (100).

Anal. Calc'd. for C$_{33}$H$_{37}$N$_4$O$_4$F$_3$•H$_2$O: C 63.05, H 6.25, N 8.91. Found: C 63.05, H 6.11, N 8.59.

EXAMPLE 102 cis-1-(t-Butylacetamido)-3-(3-chlorophenylureido)-5-phenyl-7-(4-trifluoromethylphenyl)hexahydroazepin-2-one Prepared from the more polar isomer of 1-(t-butylacetamido)-3-amino-5-phenyl-7-(4-trifluoromethylphenyl)hexahydroazepin-2-one in analogy with Example 60 in 34% yield as an amorphous solid.

$^1$H-NMR ($\delta$, CDCl$_3$, TFA): 1.19 (singlet, 9H), 2.0–2.4 (multiplets, 4H), 3.33 (m, 1H), 3.93 (AB$_q$, J$_{AB}$=17, Dn=89, 2H), 5.37 (m, 1H), 5.46 (d, J=11, 1H), 7.0–7.7 (m, 16H).

$^{13}$C-NMR ($\delta$, CDCl$_3$, TFA): 27.8, 38.6, 38.7, 45.6, 48.3, 52.6, 53.1, 61.1, 120.4, 122.6, 126.2, 126.6, 127.4, 129.0, 130.0, 130.6, 132.0, 135.3, 137.0, 140.3, 143.6, 157, 169, 176.1.

IR (cm.$^{-1}$, KBr): 1680, 1640 (broad, C=O).

FAB MS (%): 615 (parent+1, 6), 233 (23), 157 (100), 135 (47), 119 (99), 103 (52).

Anal. Calc'd. for C$_{32}$H$_{34}$N$_4$O$_3$ClF$_3$.5/4H$_2$O: C 60.28, H 5.77, N 8.79. Found: C 60.17, H 5.91, N 8.64.

EXAMPLE 103 cis-1-(t-Butylacetamido)-3-(3-tolylureido)-5-phenyl-7-(3-fluorophenyl)hexahydroazepin-2-one Prepared from the more polar isomer of 1-(t-butylacetamido)-3-amino-5-phenyl-7-(3-fluorophenyl)hexahydroazepin-2-one in analogy with Example 60 in 39% yield as an amorphous solid.

$^1$H-NMR ($\delta$, CDCl$_3$, TFA): 1.22 (singlet, 9H), 2.0–2.4 (multiplets, 4H), 2.33 (s, 3H), 3.28 (m, 1H), 3.87 (AB$_q$, J$_{AB}$=16, Dn=43, 2H), 5.21 (d, J=9, 1H), 5.32 (d, J=11, 1H), 7.0–7.4 (m, 16H).

$^{13}$C-NMR ($\delta$, CDCl$_3$, TFA): 21.2, 28.1, 38.8, 38.9, 45.7, 48.3, 52.6, 60.8, 126.7, 127.3, 128.9, 129.6, 144.0, 157, 167, 175 (not all carbons visible in this scan).

IR (cm.$^{-1}$, KBr): 1660, 1640 (broad, C=O).

FAB MS (%): 545 (parent+1, 62), 472 (52), 211 (76), 157 (100), 132 (53), 107 (53), 91 (57).

Anal. Calc'd. for C$_{32}$H$_{37}$N$_4$O$_3$F•3/4H$_2$O: C 68.86, H 6.95, N 10.04. Found: C 68.87, H 6.83, N 9.73.

EXAMPLE 104 cis-1-(t-Butylacetamido)-3-(3-methoxyphenylureido)-5-phenyl-7-(3-fluorophenyl)hexahydroazepin-2-one Prepared from the more polar isomer of 1-(t-butylacetamido)-3-amino-5-phenyl-7-(3-fluorophenyl)hexahydroazepin-2-one in analogy with Example 60 in 30% yield as an amorphous solid.

$^1$H-NMR ($\delta$, CDCl$_3$, TFA): 1.20 (singlet, 9H), 2.0–2.4 (multiplets, 4H), 3.28 (m, 1H), 3.80 (s, 3H), 3.9 (m, 2H), 5.23 (d, J=11, 1H), 5.34 (d, J=11, 1H), 6.7–6.9 and 7.1–7.4 (m, 16H).

$^{13}$C-NMR ($\delta$, CDCl$_3$, TFA): 22.2, 28.2, 38.8, 38.9, 45.7, 48.3, 52.5, 55.4, 60.8, 116.5, 126.7, 127.2, 128.9, 143.9, 176 (not all carbons visible in this scan).

IR (cm.$^{-1}$, KBr): 1670, 1640 (broad, C=O).

FAB MS (%): 561 (parent+1, 95), 488 (78), 211 (100), 157 (89), 119 (88).

Anal. Calc'd. for C$_{32}$H$_{37}$N$_4$O$_4$F•1/2H$_2$O: C 67.47, H 6.72, N 9.83. Found: C 67.20, H 6.70, N 9.14 (−0.69).

HRMS Calc'd. for C$_{37}$C$_{37}$N$_4$O$_4$F: 561.2868. Found: 561.28552.

EXAMPLE 105 cis-1-(t-Butylacetamido)-3-(3-chlorophenylureido)-5-phenyl-7-(3-fluorophenyl)hexahydroazepin-2-one Prepared from the more polar isomer of 1-(t-butylacetamido)-3-amino-5-phenyl-7-(3-fluorophenyl)hexahydroazepin-2-one in analogy with Example 60 in 52% yield as an amorphous solid.

$^1$H-NMR ($\delta$, CDCl$_3$, TFA): 1.22 (singlet, 9H), 2.0–2.4 (multiplets, 4H), 2.33 (s, 3H), 3.29 (m, 1H), 3.9 (m, 2H), 5.26 (d, J=11, 1H), 5.42 (m, 1H), 6.9–7.3 (m, 16H).

$^{13}$C-NMR ($\delta$, CDCl$_3$, TFA): 22.2, 28.1, 38.8, 39.0, 45.6, 48.4, 52.5, 60.9, 116.6, 125.1, 125.4, 126.6, 126.7, 127.3, 128.9, 130.5, 130.9, 131.0, 135.2, 143.9, 157, 164, 175.

IR (cm.$^{-1}$, KBr): 1670, 1640 (broad, C=O).

FAB MS (%): 565 (parent+1, 58), 492 (71), 211 (100), 157 (91), 132 (53(, 115 (42), 91 (49).

Anal. Calc'd. for C$_{31}$H$_{34}$N$_4$O$_3$ClF•1/2H$_2$O: C 64.86, H 6.14, N 9.76. Found: C 64.79, H 5.93, N 9.42.

EXAMPLE 106

1-(t-Butylacetamido)-3-(3-methyl, 4-chlorophenylureido)-5,7-diphenylhexahydroazepin-2-one Prepared from the more polar isomer of 1-(t-butylacetamido)-3-amino-5,7-phenyl-hexahydroazepin-2-one in Example 60 in analogy with the procedure given in Example 94 in 70% yield, mp 168°–171° C.

$^1$H-NMR ($\delta$, CDCl$_3$): 1.19 (singlet, 9H), 2.0–2.3 (m, 3H), 2.24 (s, 3H), 2.62 (m, 1H), 3.17 (m, 1H), 3.58 (AB$_q$, J$_{AB}$=16, Dn=212, 2H), 5.18 (d, J=11, 1H), 5.2 (m, 1H), 6.87 (d, J=7, 1H), 7.0–7.4 (m, 15H), 8.03 (bs, 1H).

$^{13}$C-NMR ($\delta$, CDCl$_3$): 20.1, 28.6, 38.3, 40.0, 46.3, 48.2, 51.3, 52.4, 61.2, 118.3, 126.6, 126.9, 127.1, 127.4, 128.6, 128.7, 128.9, 129.0, 129.2, 129.3 , 129 . 4, 129.5, 136.3, 138.3, 138.4, 145.2, 155.4, 167.6, 175.4.

IR (cm.$^{-1}$, KBr): 1660, 1640 (broad, C=O)

FAB MS (%): 561 (parent+1, 22), 488 (37), 394 (30), 193 (100), 132 (40), 119 (47), 115 (43), 91 (62).

Anal. Calc'd. for C$_{32}$H$_{37}$N$_4$O$_3$Cl•1/2H$_2$O: C 67.41, H 6.72, N 9.83. Found: C 67.41, H 6.73, N 9.76.

EXAMPLE 107

1-(t-Butylacetamido)-3-(3-nitrophenylureido)-5,7-diphenylhexahydroazepin-2-one

Prepared from the more polar isomer of 1-(t-butylacetamido)-3-amino-5,7-phenyl-hexahydroazepin-2-one in Example 60 in 64% yield, mp 182°–185° C.

¹H-NMR (δ, CD₃SOCD₃): 1.15 (singlet, 9H), 1.9–2.1 (m, 3H), 2.63 (m, 1H), 3.3 (m, 1H), 3.52 (AB$_q$, J$_{AB}$=16, Dn=228, 2H), 5.13 (m, 1H), 5.32 (d, J=11, 1H), 6.9–7.7 (m, 15H), 8.54 (s, 1H), 9.56 (s, 1H).

¹³C-NMR (δ, CD₃SOCD₃): 28.5, 44.9, 47.0, 50.0, 51.6, 59.4, 126.4, 126.8, 128.5, 128.7, 129.4, 139.2, 141.8, 146.2, 148.2, 153 . 8, 167.2 , 173.1.

IR (cm.⁻¹, KBr): 1660, 1640 (broad, C=O).

FAB MS (%): 558 (parent+1, 20), 485 (23), 193 (67), 155 (52), 185 (85), 119 (100), 103 (48), 91 (39).

Anal. Calc'd. for C₃₁H₃₅N₅O₅·2/3H₂O: C 65.36, H 6.43, N 12.29. Found: C 65.06, H 6.35, N 11.91.

EXAMPLE 108

1-(t-Butylacetamido)-3-(3-aminophenylureido)-5,7-diphenylhexahydroazepin-2-one

Prepared from 1-(t-butylacetamido)-3-(3-aminophenylureido)-5,7-diphenylhexahydroazepin-2-one in 90% yield by reduction with 5 equivalents of ammonium formate in ethanol at room temperature in the presence of 10% palladium-on-carbon, mp 163°–168° C.

¹H-NMR (δ, CDCl₃): 1.17 (singlet, 9H), 2.0–2.3 (m, 3H), 2.48 (m, 1H), 3.18 (m, 1H), 3.59 (AB$_q$, J$_{AB}$=16, Dn=160, 2H), 4.08 (bs, 2H), 5.15 (d, J=10, 1H), 5.21 (m, 1H), 5.47 (s, 1H), 6.26 (d, J=7, 1H), 6.7–7.4 (m, 15H), 8.96 (bs, 1H).

¹³C-NMR (δ, CDCl₃): 28.6, 39.0, 39.6, 46.1, 48.2, 51.2, 52.2, 60.4, 61.1, 106.5, 109.7, 126.6, 126.9, 127.0, 128.4, 128.6, 128.8, 128.9, 129.1, 129.5, 129.7, 138.3, 140.4, 145.3, 147.3, 155.4, 167.6, 175.1.

IR (cm.⁻¹, KBr): 1640 (broad, C=O).

FAB MS (%): 528 (parent+1, 81), 455 (53), 394 (69), 193 (94), 157 (99), 119 (100).

Anal. Calc'd. for C₃₁H₃₇N₅O₃Cl·H₂O: C 68.23, H 7.20, N 12.83. Found: C 68.73 (+0.50), H 7.07, N 12.43.

EXAMPLE 109

1-(t-Butylacetamido)-3-(3-acetylaminophenylureido)-5,7-diphenylhexahydroazepin-2-one Prepared from 1-(t-butylacetamido)-3-(3-aminophenylureido)-5,7-diphenylhexahydroazepin-2-one 70% yield by acetylation with acetic anhydride in pyridine at reflux for 14 hr, mp 195°–205° C.

¹H-NMR (δ, CD₃SOCD₃): 1.15 (singlet, 9H), 1.8–2.0 (m, 3H), 2.57 (m, 1H), 3.17 (m, 1H), 3.51 (AB$_q$, J$_{AB}$=16, Dn=228, 2H), 5.01 (m, 1H), 5.30 (d, J=10, 1H), 6.7–7.4 (m, 15H), 7.67 (s, 1H), 9.01 (s, 1H), 9.82 (bs, 1H).

¹³C-NMR (δ, CD₃SOCD₃): 24.0, 28.5, 45.1, 47.0, 49.9, 51.6, 59.4, 112.0, 112.3, 126.3, 126.8, 128.0, 128.1, 128.5, 128.7, 128.8, 129.3, 129.4, 129.5, 134.6, 139.3, 139.7, 140.8, 146.3, 154.1, 167.3, 168.2, 173.3.

IR (cm.⁻¹, KBr): 1660, 1640 (broad, C=O).

FAB MS (%): 570 (parent+1, 25), 497 (29), 193 (42), 157 (100), 119 (34).

Anal. Calc'd. for C₃₃H₃₉N₅O₄·H₂O: C 67.44, H 7.03, N 11.92. Found: C 67.31, H 7.08, N 11.71.

EXAMPLE 110

1-(t-Butylacetamido)-3-(3-methylsulfonylaminophenylureido)-5,7-diphenylhexahydroazepin-2-one Prepared from 1-(t-butylacetamido)-3-(3-aminophenylureido)-5,7-diphenylhexahydroazepin-2-one in 69% yield by reaction with methanesulfonyl chloride in pyridine at room temperature, mp 185°–192° C.

¹H-NMR (δ, CD₃SOCD₃): 1.15 (singlet, 9H), 1.8–2.0 (m, 3H), 2.57 (m, 1H), 2.94 (s, 3H), 3.20 (m, 1H), 3.50 (AB$_q$, J$_{AB}$=16, Dn=231, 2H), 5.09 (d, J=11, 1H), 5.30 (d, J=10, 1H), 6.6–7.4 (m, 16H), 9.11 (s, 1H), 9.62 (s, 3H).

¹³C-NMR (δ, CD₃SOCD₃): 28.5, 45.0, 47.0, 49.9, 51.5, 59.4, 108.3, 126.8, 126.9, 128.0, 128.4, 128.5, 128.6, 128.7, 129.3, 129.4, 129.5, 129.6, 139.3, 141.4, 146.3, 153.6, 167.3, 173.2.

IR (cm.⁻¹, KBr): 1640 (broad, C=O).

FAB MS (%): 606 (parent+1, 47), 533 (64), 193 (100), 119 (63), 91 (59).

Anal. Calc'd. for C₃₂H₃₉N₅O₅S·1/2H₂O: C 62.52, H 6.56, N 11.39, S 5.22. Found: C 62.12, H 6.80, N 11.08, S 5.32.

EXAMPLE 111

1-(t-Butylacetamido)-3-(3-(N-methylureido)phenylureido)-5,7-diphenylhexahydroazepin-2-one Prepared from 1-(t-butylacetamido)-3-(3-aminophenylureido)-5,7-diphenylhexahydroazepin-2-one in 45% yield by reaction with methylisocyanate in refluxing tetrahydrofuran for 18 hr, mp 185°–195° C.

¹H-NMR (δ, CDCl₃): 1.10 (singlet, 9H), 1.9–2.2 (m, 3H), 2.5 (m, 1H), 2.60 (bs, 3H), 3.04 and 3.8 (multiplets, 2H), 3.28 (m, 1H), 5.0–5.2 (broad multiplet, 2H), 5.4–5.6 (broad multiplet, 2H), 6.8–7.4 (m, 15H), 7.6 (bs, 1H), 8.1 (bs, 1H).

¹³C-NMR (δ, CDCl₃): 26.6, 28.5, 46.0, 51.1, 126.9, 127.0, 128.4, 128.6, 128.7, 128.8, 128.9, 129.0, 129.5, 129.6, remaining carbons not visible in this scan.

IR (cm.⁻¹, KBr): 1640 (broad, C=O).

FAB MS (%): 585 (parent+1, 26), 512 (60), 193 (100), 115 (42), 91 (58).

Anal. Calc'd. for C₃₃H₄₀N₆O₄·H₂O: C 65.76, H 7.02, N 13.94. Found: C 65.94, H 6.74, N 13.58.

EXAMPLE 112

N-(1-Methylcyclohexyl) 2-[3-bromo-2-oxo-5-(phenyl)-2,3,4,5-tetrahydro-1H-(1)benzazepin-1-yl] ethanoic acid amide Prepared in analogy with Example 1 using N-(1-methylcyclohexyl) iodoacetamide to alkylate 3-bromo-2-oxo-5-(phenyl)-2,3,4,5-tetrahydro-1H-(1)benzazepine in 75% yield, mp 164°–168° C.

¹H-NMR (δ, CDCl₃): 1.35 (s, 9H), 1.46 (s, 3H), 1.2–1.5 and 1.9–2.1 (m, 10H), 2.62 and 2.79 (multiplets for 2 diastereomers, 1H), 2.92 (m, 1H), 4.2–4.7 (m, 4H), 6.0 and 6.11 (singlets, 1H), 6.6–7.4 (m, 9H).

¹³C-NMR (δ, CDCl₃): 121.9, 22.0, 25.5, 26.4, 36.3, 36.9, 43.0, 43.1, 44.1, 44.8, 47.1, 53.7, 54.8, 55.1, 56.5, 123.2, 127.5, 127.6, 127.7, 127.8, 128.0, 128.1, 128.7, 128.8, 129.0, 137.5, 137.7, 139.0, 140.7, 141.1, 167.1, 168.2, 168.7.

IR (cm⁻¹, KBr): 1660 broad (C=O).

MS (%): 468/470 (parent for Br⁷⁹/Br⁸¹, 1/1), 276 (50), 250 (51), 165 (40), 97 (38), 55 (100).

N-(1-Methylcyclohexyl) 2-[3-azido-2-oxo-5-(phenyl)-2,3,4,5-tetrahydro-1H-(1)benzazepin-1-yl] ethanoic acid amide Prepared in analogy with Example 1 in 41% yield as an oil.

¹H-NMR (δ, CDCl₃): 1.29 (s, 9H), 1.43 (s, 3H), 1.1–1.6 and 1.8–2.0 (m, 10H), 2.76 (m, 1H), 2.92 (m, 1H), 3.09 (AB$_q$, J$_{AB}$=15, dn=317, 2H), 3.97 (m, 1H), 4.20 (m, 1H), 6.18 (bs, 1H), 6.9–7.5 (m, 9H).

¹³C-NMR (δ, CDCl₃)): 21.8, 22.0, 25.5, 26.4, 35.7, 35.8, 36.0, 36.1, 36.3, 36.9, 37.0, 43.7, 53.4, 54.7, 58.4, 125.5, 125.6, 125.7, 125.8, 125.9, 126.0, 126.2, 126.5, 126.6, 126.7, 127.3, 127.5, 127.6, 127.7, 128.0, 128.5, 128.7, 129.2, 129.3, 130.3, 130.4, 1307.9, 141.0, 141.1, 168.0, 170.0.

IR (cm.⁻¹, KBr): 2100 (N₃) and 1675 broad (C=O).

FAB MS (%): 432 (parent+1, 32), 406 (70), 319 (100), 293 (92), 194 (90), 91 (92).

HRMS Calc'd. for C₂₅H₂₉N₅O₂: 431.2315. Found: 431.23135.

N-(1-Methylcyclohexyl) 2-[3-amino-2-oxo-5-(phenyl)-2,3,4,5-tetrahydro-1H-(1)benzazepin-1-yl] ethanoic acid amide Prepared in analogy with Example 1 in 69% yield as a white foam.

¹H-NMR (δ, CDCl₃): 1.26 (s, 9H), 1.39 (s, 3H), 1.0–1.7 and 1.8–2.0 (m, 10H), 2.22 (bs, 2H), NH₂), 2.5 (m, 1H), 2.78 (m, 1H), 3.08 (AB$_q$, J$_{AB}$=15, dn=305, 2H), 3.48 (m, 1H), 4.10 (m, 1H), 6.10 (bs, 1H), 6.9–7.4 (m, 9H).

¹³C-NMR (δ, CDCl₃): 21.9, 25.5, 26.4, 31.5, 36.2, 36.8, 39.7, 44.5, 50.7, 53.4, 54.4, 125.3, 125.4, 125.5, 126.2, 127.2, 128.3, 128.5, 128.8, 130.2, 138.7, 141.6, 141.8, 168.3, 175.1.

IR (cm.⁻¹, KBr): 1660 broad (C=O).

FAB MS (%): 406 (parent+1, 84), 293 (100), 237 (38), 194 (43).

HRMS Calc'd. for C₂₅H₃₁N₃O₂: 405.2409. Found: 405.23807.

N-(1-Methylcyclohexyl) 2-[3-(3-(3-ethylphenyl)ureido)-2-oxo-5-(phenyl)-2,3,4,5-tetrahydro-1H-(1) benzazepin-1-yl]ethanoic acid amide Prepared from N-(1-methylcyclohexyl) 2-[3-amino-2-oxo-5-(phenyl)-2,3,4,5-tetrahydro-1H-(1)benzazepin-1-yl] ethanoic acid amide as in Example 1, mp 130°–140° C., 94% yield.

¹H-NMR (δ, CDCl₃): 1.16 (t, J=8, 3H), 1.28 (s, 9H), 1.37 (s, 3H), 1.2–1.5 (m, 6H), 1.8–2.0 (m, 4H), 2.54 (q, J=8, 2H), 2.9 and 3.1 (m, 2H), 3.24 (AB$_q$, J$_{AB}$=16, dn=297, 2H), 4.22 (d, J=8, 1H), 4.66 (m, 1H), 5.90 (bs, 1H), 6.5–7.4 (m, 13H), 7.71 (bs, 1H).

¹³C-NMR (δ, CDCl₃): 15.6, 21.9, 22.0, 25.4, 26.1, 28.9, 36.4, 36.6, 37.3, 44.4, 50.1, 53.8, 54.0, 117.2, 119.6, 119.7, 122.5, 124.9, 125.0, 126.3, 126.4, 127.8, 127.9, 128.4, 128.8, 128.9, 129.0, 130.7, 130.8, 138.3, 139.1, 141.2, 141.8, 145.3, 155.4, 167.7, 173.0.

IR (cm.⁻¹, KBr): 1650 broad (C=O).

FAB MS (%): 553 (parent+1, 32), 440 (68), 293 (84), 220 (82), 194 (100), 91 (56).

Anal. Calc'd. for C₃₄H₄₀N₄O₃·1/4H₂O: C 73.29, H 7.33, N 10.05. Found: C 73.30, H 7.15, N 10.25.

EXAMPLE 113

N-(1-Methylcyclohexyl) 2-[3-(3-(3-chlorophenyl)ureido)-2-oxo-5-(phenyl)-2,3,4,5-tetrahydro-1H-(1) benzazepin-1-yl]ethanoic acid amide Prepared from N-(1-methylcyclohexyl) 2-[3-amino-2-oxo-5-(phenyl)-2,3,4,5-tetrahydro-1H-(1)benzazepin-1-yl] ethanoic acid amide as in Example 107, mp 215°–220° C., 84% yield.

¹H-NMR (δ, CDCl₃): 1.28 (s, 9H), 1.36 (s, 3H), 1.2–1.5 (m, 6H), 1.8–2.0 (m, 4H), 2.9–3.0 (m, 2H), 3.33 (AB$_q$, J$_{AB}$=16, dn=284, 2H), 4.26 (d, J=7, 1H), 4.63 (m, 1H), 5.79 (bs, 1H), 6.6–7.6 (m, 13H), 7.99 (bs, 1H).

¹³C-NMR (δ, CDCl₃): 22.0, 22.1, 25.4, 25.9, 36.4, 36.7, 36.9, 44.5, 53.4, 54.1, 117.1, 119.1, 122.2, 124.4, 124.5, 126.3, 126.5, 126.6, 127.8, 128.4, 129.1, 129.6, 130.8, 134.3, 138.2, 140.7, 141.1, 141.7, 155.1, 167.4, 173.2.

IR (cm.⁻¹, KBr): 1650 broad (C=O)

FAB MS (%): 559/561 (parent+1, Cl³⁵/Cl³⁷ 21/8), 446 (69), 293 (55), 237 (58), 220 (92), 194 (100), 97 (80).

Anal. Calc'd. for C₃₂H₃₅N₄O₃Cl: C 68.74, H 6.31, N 10.02. Found: C 68.40, H 6.19, N 9.82.

EXAMPLE 114

N-(1-Methylcyclohexyl) 2-[3-(3-(3-tolyl)ureido)-2-oxo-5-(phenyl)-2,3,4,5-tetra-hydro-1H-(1) benzazepin-1-yl]ethanoic acid amide Prepared from N-(1-methylcyclohexyl) 2-[3-amino-2-oxo-5-(phenyl)-2,3,4,5-tetrahydro-1H-(1)benzazepin-1-yl] ethanoic acid amide as in Example 107, mp 220°–225° C., 85% yield.

¹H-NMR (δ, CDCl₃): 1.28 (s, 9H), 1.38 (s, 3H), 1.2–1.5 (m, 6H), 1.8–2.0 (m, 4H), 2.23 (s, 3H), 2.8 (m, 1H), 3.06 (m, 1H), 3.22 (AB$_q$, J$_{AB}$=16, Δv=297, 2H), 4.23 (d, J=8, 1H), 4.65 (m, 1H), 5.90 (bs, 1H), 6.5–7.4 (m, 13H), 7.68 (bs, 1H).

¹³C-NMR (δ, CDCl₃): 21.5, 21.9, 22.0, 25.5, 26.1, 36.4, 37.2, 44.4, 50.1, 53.8, 53.9, 116.9, 117.0, 120.6, 123.7, 124.9, 126.3, 126.5, 127.8, 128.3, 128.5, 128.7, 129.0, 129.1, 130.7, 130.8, 138.3, 138.8, 139.0, 141.2, 141.8, 155.3, 167.6, 172.9.

IR (cm.⁻¹, KBr): 1650 broad (C=O).

FAB MS (%): 539 (parent+1, 60), 426 (82), 293 (92), 220 (94), 194 (100), 119 (73), 97 (71), 91 (99).

EXAMPLE 115

2-(Cyclohexyl)-2-phenylethanol

To a 500 mL round-bottomed flask equipped with condenser and N₂ inlet were added 15 g (68.8 mmol) α-phenylcyclohexylacetic acid, 110 mL dry tetrahydrofuran, and 137 mL (275 mmol) of a 2M solution of borane-methyl sulfide in tetrahydrofuran. The solution was refluxed 60 hr, cooled, and evaporated. The residue was taken up carefully in 200 mL ethanol, treated with 2 g sodium carbonate, and refluxed 3 hr. The reaction was cooled, evaporated, taken up in ethyl acetate/water, separated, and the aqueous phase extracted with fresh ethyl acetate. The organic layers were combined, washed with brine, dried over sodium sulfate, and evaporated to an oil which solidified on standing. The yield was 12.27 g (87%).

¹H-NMR (δ, CDCl₃): 0.7–1.9 (m, 11H), 2.54 (m, 1H), 3.7–3.9 (m, 2H), 7.1–7.3 (m, 5H).

2-(Cyclohexyl)-2-phenylethanol tosylate

To a 125 mL round-bottomed flask were added 12.27 g (60.15 mmol) 2-(cyclohexyl)-2-phenylethanol and 30 mL dry pyridine. The reaction was cooled to 0° C., and 13.78 g (72.18 mmol) tosyl chloride added. The reaction was let stand at 0° C. for 14 hr, poured into water, and extracted into ether. The ether layer was washed with 3 portions of 1N hydrochloric acid, 3 portions of saturated aqueous sodium bicarbonate solution, 2 portions water, and brine, dried over sodium sulfate, and evaporated. The residue was slurried in ethanol and collected by filtration to afford a white solid, mp 95°–100° C. 13 1 g (61%)

$^1$H-NMR (δ, CDCl$_3$): 0.6–1.7 (m, 11H), 2.40 (s, 3H), 2.64 (m, 1H), 4.1–4.3 (m, 2H), 6.9–7.5 (m, 5H).

IR (cm.$^{-1}$, KBr): 2940 (C—H) and 1600 (C=C).

MS (%): 186 (100, parent for elimination of tosic acid), 104 (95), 91 (70).

Anal. Calc'd. for C$_{21}$H$_{26}$O$_3$S: C 70.35, H 7.31. Found: C 70.32, H 7.33.

2-(Cyclohexyl)-2-phenyl-1-iodoethane

To a 250 mL round-bottomed flask equipped with condenser and N$_2$ inlet were added 13.9 g (39.4 mmol) 2-(cyclohexyl)-2-phenylethanol tosylate, 80 mL acetone and 6.49 g (43.3 mmol) sodium iodide. The reaction was refluxed 36 hr, cooled, and evaporated. The residue was taken up in ethyl acetate, washed with water and aqueous sodium bisulfite solution, dried over sodium sulfate, and evaporated to an oil, 12.11 g (98%), which was used directly in the next step.

$^1$H-NMR (δ, CDCl$_3$): 0.7–1.9 (m, 11H), 2.60 (m, 1H), 3.4 and 3.6 (m, 2H), 7.0–7.3 (m, 5H).

Diethyl-(2-(cyclohexyl)-2-phenylethyl)malonate

To a 500 mL round-bottomed flask equipped with condenser and N$_2$ inlet were added 3.05 g (77.1 mmol) sodium hydride, which was washed with hexane and the hexane pipetted off, and 100 mL dry tetrahydrofuran. To the stirring suspension was added a solution of 12.34 g (77.1 mmol) diethyl malonate in 50 mL dry tetrahydrofuran dropwise over 30 min. Once gas evolution had ceased, a solution of 12.11 g (38.57 mmol) 2-(cyclohexyl)-2-phenyl-1-iodoethane in 40 mL dry tetrahydrofuran was added, and the reaction refluxed 3 days. The reaction was concentrated, poured into 1N hydrochloric acid, and extracted twice into ethyl acetate. The combined organic layer was washed with water, 3 portions of aqueous sodium bisulfite solution, and brine, dried over sodium sulfate, and evaporated. The residue was chromatographed on silica gel using hexane/ethyl acetate as eluant to afford an oil, 12.53 g (87%).

$^1$H-NMR (δ, CDCl$_3$): 0.6–2.0 (m, 12H), 1.12 (t, J=7, 3H), 1.20 (t, J=7, 3H), 2.24 (m, 1H), 2.32 (m, 1H), 2.95 (dd, J=4,10, 1H), 3.98 (m, 2H), 4.15 (m, 2H), 6.9–7.2 (m, 5H).

$^{13}$C-NMR (δ, CDCl$_3$): 13.9, 14.1, 26.4, 26.5, 31.1, 31.2, 32.0, 43.3, 49.7, 50.3, 61.0, 61.2, 126.3, 128.2, 128.5, 142.6, 169.4, 169.6.

IR (cm.$^{-1}$, KBr): 1738 (C=O).

MS (%): 346 (parent, 12), 160 (100), 114 (60), 28 (59).

HRMS Calc'd. for C$_{21}$H$_{30}$O$_4$: 346.2136. Found: 346.21838.

3-Cyclohexyl-3-phenylbutanoic acid

To a 250 mL round-bottomed flask equipped with condenser and N$_2$ inlet were added 12.53 g (36.2 mmol) diethyl-(2-(cyclohexyl)-2-phenylethyl)malonate, 80 mL acetic acid, and 25 mL 6N hydrochloric acid. The reaction was refluxed 20 hr, cooled, poured into water, and extracted into ethyl acetate. The organic phase was washed with water and brine, dried over sodium sulfate, and evaporated. Evaporation from heptane removed traces of water to afford an oil, 9.78 g (99% crude yield).

$^1$H-NMR (δ, CDCl$_3$): 0.8–2.3 (m, 16H), 7.0–7.3 (m, 5H).

$^{13}$C-NMR (δ, CDCl$_3$): 26.5, 27.7, 31.2, 31.3, 32.6, 43.2, 51.6, 126.2, 128.3, 128.5, 143.3, 180.8.

IR (cm.$^{-1}$, KBr): 1720 (C=O)

MS (%): 246 (parent, 13), 173 (45), 163 (52), 117 (78), 104 (100), 91 (79), 55 (48).

HRMS Calc'd. for C$_{16}$H$_{22}$O$_2$: 246.1614. Found: 246.15968.

The remaining steps were carried out as described for the analogous compounds in Example 22:

4-Cyclohexyl-1,2,3,4-tetrahydronaphth-1-one

Prepared as an oil in 74% yield.

$^1$H-NMR (δ, CDCl$_3$): 1.9–2.1 (m, 5H), 1.4–1.8 (m, 6H), 2.0–2.2 (m, 2H), 2.4–2.7 (m, 3H), 7.0–7.3 (m, 3H), 7.88 (m, 1H).

$^{13}$C-NMR (δ, CDCl$_3$): 24.3, 26.3, 26.5, 30.5, 35.0, 39.9, 44.0, 126.6, 127.4, 129.2, 132.3, 132.6, 147.3, 198.6.

IR (cm.$^{-1}$, KBr): 1690 (C=O)

MS (%): 228 (parent, 7), 146 (100), 55 (20).

HRMS Calc'd. for C$_{16}$H$_{20}$O: 228.1509. Found: 228.15016.

4-Cyclohexyl-1,2,3,4-tetrahydronaphth-1-one oxime

Prepared as a solid, mp 120°–123° C. in 71% yield.

$^1$H-NMR (δ, CDCl$_3$): 0.8–1.7 (m, 11H), 1.88 (m, 1H), 2.12 (m, 1H), 2.39 (m, 1H), 2.79 (m, 2H), 7.0–7.3 (m, 3H), 7.77 (m, 1H).

$^{13}$C-NMR (δ, CDCl$_3$): 20.5, 22.4, 26.3, 26.4, 31.0, 32.0, 38.8, 44.9, 124.6, 126.6, 128.5, 129.7, 129.9, 143.2, 155.6.

IR (cm.$^{-1}$, KBr): 1640 (weak) (C=N).

Anal. Calc'd. for C$_{16}$H$_{21}$NO: C 78.97, H 8.70, N 5.75. Found: C 78.83, H 8.74, N 5.64.

5-Cyclohexyl-2,3,4,5-tetrahydro-1H-(1)benzazepin-2-one

Prepared as a white solid, mp 125°–128° C., in 80% yield.

$^1$H-NMR (δ, CDCl$_3$): 0.6–2.0 (m, 12H), 2.2–2.4 (m, 3H), 2.59 (m, 1H), 6.9–7.2 (m, 4H), 8.80 (bs, 1H).

$^{13}$C-NMR (δ, CDCl$_3$): 26.3, 26.4, 31.0, 31.6, 32.5, 32.7, 38.7, 45.8, 122.4, 125.3, 126.9, 128.6, 136.3, 138.2, 176.1.

IR (cm.$^{-1}$, KBr): 1680 (C=O)

MS (%): 243 (40, parent), 160 (100), 132 (32), 118 (37).

Anal. Calc'd. for C$_{16}$H$_{21}$NO: C 78.97, H 8.70, N 5.75. Found: C 78.77, H 8.71, N 5.66.

3-Bromo-5-cyclohexyl-2,3,4,5-tetrahydro-1H-(1)benzazepin-2-one

Prepared as a white solid, mp 104°–107° C. in 54% yield.

$^1$H-NMR (δ, CDCl$_3$): 0.6–2.0 (m, 11H), 2.25 (m, 1H), 2.69 (m, 2H), 4.37 (dd, J=7,11, 1H), 7.0–7.3 (m, 4H), 8.90 (bs, 1H).

$^{13}$C-NMR (δ, CDCl$_3$): 26.1, 26.4, 30.3, 32.3, 38.0, 44.2, 44.9, 48.0, 123.1, 126.5, 126.9, 127.2, 135.3, 137.3, 169.6.

N-t-Butyl 2-[3-bromo-2-oxo-5-cyclohexyl-2,3,4,5,-tetrahydro-1H-(1)benzazepin-1-yl]ethanoic acid amide Prepared as a mixture of diastereomers, which separated into the less polar isomer, mp 188°–189.5° C., 36% yield, and the more polar isomer, mp 190.5°–192° C., 58% yield. Less polar isomer:

$^1$H-NMR (δ, CDCl$_3$): 0.4–2.0 (m, 11H), 1.36 (s, 9H), 2.39 (m, 1H), 2.61 (m, 2H), 4.01 (AB$_q$, J$_{AB}$=15, Dn=381, 2H), 4.59 (dd, J=8,12, 1H), 6.25 (bs, 1H), 6.9–7.4 (m, 4H).

$^{13}$C-NMR (δ, CDCl$_3$): 26.1, 26.2, 28.7, 32.2, 32.5, 40.1, 42.5, 47.4, 50.3, 51.5, 55.7, 124.7, 127.5, 128.6, 131.4, 136.0, 141.4, 167.6, 168.6.

More polar isomer:

$^1$H-NMR (δ, CDCl$_3$): 0.6–1.9 (m, 11H), 1.31 (s, 9H), 2.06 (m, 1H), 2.65 (m, 2H), 4.26 (AB$_q$, J$_{AB}$=15, Dn=32, 2H), 4.2 (m, 1H), 6.22 (bs, 1H), 7.1–7.3 (m, 4H).

$^{13}$C-NMR (δ, CDCl$_3$): 26.0, 26.3, 26.4, 28.7, 30.3, 32.0, 37.7, 43.7, 45.4, 48.1, 51.4, 54.8, 123.6, 126.1, 127.5, 127.6, 127.7, 136.2, 142.0, 167.1, 168.4.

N-tert-butyl-2-[3-azido-2-oxo-5-cyclohexyl-2,3,4,5-tetrahydro-1H-(1)benzazepin-1-yl]ethanoic acid amide Prepared from the more polar diastereomer in the previous step in 47% yield, mp 136°–139° C.

$^1$H-NMR (δ, CDCl$_3$): 0.4–2.0 (m, 11H), 1.34 (s, 9H), 2.22 (m, 1H), 2.43 (m, 2H), 3.84 (m, 1H), 4.04 (AB$_q$, J$_{AB}$=15, Dn=291, 2H), 6.32 (bs, 1H), 7.0–7.4 (m, 4H).

$^{13}$C-NMR (δ, CDCl$_3$): 26.0, 26.1, 26.2, 28.6, 32.2, 32.5, 36.6, 40.2, 47.7, 51.5, 55.1, 58.4, 124.6, 127.4, 128.6, 131.3, 136.4, 140.7, 167.7, 170.8.

N-tert-butyl-2-[3-amino-2-oxo-5-cyclohexyl-2,3,4,5-tetrahydro-1H-(1)benzazepin-1-yl]ethanoic acid amide Prepared as a solid, mp 105°–115° C., in quantitative yield.

$^1$H-NMR (δ, CDCl$_3$): 0.4–1.7 (m, 10H), 1.31 (s, 9H), 1.98 (m 1H), 2.18 (m, 1H), 2.39 (m, 1H), 2.62 (m, 1H), 3.79 (m, 1H), 4.08 (AB$_q$, J$_{AB}$=15, Dn=364, 2H), 5.5 (bs, 2H), 6.61 (bs, 1H), 7.0–7.3 (m, 4H).

$^{13}$C-NMR (δ, CDCl$_3$): 25.9, 26.2, 28.7, 32.2, 32.3, 37.7, 39.9, 47.9, 50.6, 51.7, 54.1, 124.1, 127.3, 128.5, 131.6, 136.6, 140.4, 167.7, 172.1.

N-tert-butyl-2-[3-(3-(3-tolyl)ureido)-2-oxo-5-cyclohexyl-2,3,4,5-tetrahydro-1H-(1)benzazepin-1-yl]ethanoic acid amide Prepared as a white solid, mp 225°–228° C., 67% yield.

$^1$H-NMR (δ, CDCl$_3$): 0.54 (m, 1H), 0.8–1.8 (m, 9H),1.35 (s, 9H), 2.0–2.2 (m, 2H), 2.49 (m, 1H), 2.64 (m, 1H), 4.17 (AB$_q$, J$_{AB}$=16, Dn=408, 2H), 4.52 (m, 1H), 6.23 (d, J=7, 1H), 6.28 (s, 1H), 6.7–7.3 (m, 8H), 7.62 (s, 1H).

$^{13}$C-NMR (δ, CDCl$_3$): 21.4, 26.1, 26.2, 26.3, 28.7, 32.3, 32.5, 37.6, 40.4, 48.2, 50.6, 51.8, 54.0, 116.8, 120.5, 123.4, 123.5, 127.3, 128.4, 128.5, 128.6, 131.7, 136.7, 138.6, 139.0, 140.9, 155.5, 167.5, 174.1.

EXAMPLE 116

N-tert-butyl-2-[3-(3-(3-chlorophenyl)ureido)-2-oxo-5-cyclohexyl-2,3,4,5-tetrahydro-1H-(1)benzazepin-1-yl]ethanoic acid amide Prepared from N-tert-butyl-2-[3-amino-2-oxo-5-cyclohexyl-2,3,4,5-tetrahydro-1H-(1)benzazepin-1-yl] ethanoic acid amide as in Example 115 as a white solid, mp 223°–226° C., 48% yield.

$^1$H-NMR (δ, CDCl$_3$): 0.52 (m, 1H), 0.8–1.8 (m, 9H), 1.37 (s, 9H), 1.98 (m, 1H), 2.13 (m, 1H), 2.48 (m, 1H), 2.58 (m, 1H), 4.23 (AB$_q$, J$_{AB}$=16, Dn=408, 2H), 4.48 (m, 1H), 6.28 (s, 1H), 6.39 (δ, J=7, 1H), 6.8–7.3 (m, 7H), 7.55 (s, 1H), 8.01 (s, 1H).

$^{13}$C-NMR (δ, CDCl$_3$): 26.1, 26.2, 28.7, 32.3, 32.5, 37.2, 40.3, 48.2, 50.7, 52.1, 53.6, 116.9, 118.9, 119.0, 122.1, 123.0, 127.4, 128.6, 129.4, 131.8, 134.2, 136.6, 140.5, 140.7, 155.2, 167.4, 174.5.

EXAMPLE 117

N-tert-butyl-2-[3-(3-(3-ethylphenyl)ureido)-2-oxo-5-cyclohexyl-2,3,4,5-tetrahydro-1H-(1)benzazepin-1-yl]ethanoic acid amide Prepared from N-tert-butyl-2-[3-amino-2-oxo-5-cyclohexyl-2,3,4,5-tetrahydro-1H-(1)benzazepin-1-yl] ethanoic acid amide as in Example 115 as a white solid, mp 145°–155° C., 61% yield.

$^1$H-NMR (δ, CDCl$_3$): 0.48 (m, 1H), 0.7–1.7 (m, 9H), 1.30 (t, J=7.5, 3H), 1.35 (s, 9H), 1.9–2.1 (m, 2H), 2.47 (q, J=7.5, 2H), 2.62 (m, 1H), 4.16 (AB$_q$, J$_{AB}$=16, Dn=404, 2H), 4.50 (m, 1H), 6.23 (d, J=7, 1H), 6.26 (s, 1H), 6.7–7.3 (m, 8H), 7.63 (s, 1H).

$^{13}$C-NMR (δ, CDCl$_3$): 15.6, 26.1, 26.2, 26.3, 28.7, 28.9, 32.3, 32.5, 37.7, 40.4, 48.2, 50.5, 51.8, 54.1, 117.1, 119.4, 119.5, 122.4, 123.4, 123.5, 127.3, 128.5, 128.7, 131.7, 136.7, 139.0, 140.9, 145.1, 155.4, 167.6, 176.0.

EXAMPLE 118

4-(4-Fluorophenyl)-4-hydroxycyclohexanone ethyleneketal

Prepared in analogy with *J. Med. Chem.*, 1992, 35, 320–324 as follows: To a 1 L round-bottomed flask equipped with N$_2$ inlet were added 46.8 g (0.30 mol) cyclohexane-1, 4-dione monoethylene ketal and 500 mL dry tetrahydrofuran. The solution was cooled to −78° C., and 150 mL of a 2.0M solution (0.30 mol) of 4-fluorophenylmagnesium bromide in ether was added dropwise over 30 min, then the reaction was stirred for 10 min and warmed to room temperature. The reaction was poured into ice/water, the layers separated, and the aqueous phase extracted with ether. The combined organic phase was dried over sodium sulfate and evaporated to a an oil, which was triturated with ether to a white, low-melting solid, 24.3 g (32%).

$^1$H-NMR (δ, CDCl$_3$): 1.6–1.8 (m, 4H), 2.05 (m, 4H), 3.95 (bs, 4H), 6.96 (m, 2H), 7.61 (m, 2H).

$^{13}$C-NMR (δ, CDCl$_3$): 30.7, 36.7, 64.2, 64.4, 72.1, 108.3, 114.8, 115.1, 126.2, 126.3, 144.

MS (%): 234 (7, parent-H$_2$O), 123 (15), 99 (100), 86 (60).

4-(4-Fluorophenyl)cyclohexanone

A solution of 5.0 g (19.8 mmol) 4-(4-fluorophenyl)-4-hydroxycyclohexanone ethylene ketal in 170 mL dioxane was treated with 5.0 g 10% palladium-on-carbon under 35 p.s.i. hydrogen for 24 hr, then filtered through Celite to remove the catalyst. The filtrate was treated with 100 mL water and 3.5 mL concentrated hydrochloric acid, and stirred at room temperature for 24 hr. The solution was evaporated, the pH adjusted to 8 with saturated aqueous sodium bicarbonate solution, and extracted with methylene chloride. The organic layer was dried over sodium sulfate and evaporated. The residue was chromatographed on silica gel using methylene chloride as eluant to afford 2.9 g (74%) of an oil.

$^1$H-NMR (δ, CDCl$_3$): 1.83 (m, 2H), 2.12 (m, 2H), 2.42 (m, 4H), 2.96 (m, 1H), 6.8–7.2 (m, 4H).

$^{13}$C-NMR (δ, CDCl$_3$): 34.1, 35.1, 41.3, 42.0, 115.2, 115.5, 128.0, 128.1, 140.4, 140.5, 159.9, 163.1, carbonyl carbon not visible in this scan.

IR (cm$^{-1}$, CHCl$_3$): 1705 (C=O).

MS (%): 192 (90), 135 (60), 122 (100), 109 (65), 57 (15).

HRMS Calc'd. for $C_{12}H_{13}FO$: 192.0947. Found: 192.0983. The remainder of the synthesis was carried out as described in Example 60:

2-Chloro-4-(4-fluorophenyl)cyclohexanone

Prepared as an oil in 93% yield.

$^1$H-NMR ($\delta$, $CDCl_3$): 1.9–3.7 (series of multiplets, 7H), 4.67 and 5.34 (multiplets, 1H), 6.8–7.2 (m, 4H).

$^{13}$C-NMR ($\delta$, $CDCl_3$): 33.4, 33.9, 34.3, 35.9, 40.4, 42.8, 45.5, 63.2, 115.5, 115.7, 128.0, 128.1, 128.2, 128.3, carbonyl carbon not visible in this scan.

MS (%): 226 (55, parent), 171 (85), 122 (100), 109 (95), 55 (45).

2-Phenyl-4-(4-fluorophenyl)cyclohexanone

Prepared as an oil in 29% yield.

$^1$H-NMR ($\delta$, $CDCl_3$): 2.0–2.4 (m, 4H), 2.64 (m, 2H), 33.24 (m, 1H), 3.79 (dd, J=5,13, 1H), 6.9–7.4 (m, 9H).

MS (%): 268 (100, parent), 224 (90), 135 (65), 122 (95), 109 (75), 91 (99).

2-Phenyl-4-(4-fluorophenyl)cyclohexanone oxime

Prepared as a light yellow solid, mp 192°–194° C., in 64% yield.

$^1$H-NMR ($\delta$, DMSO-$d_6$): 1.5–2.2 (m, 4H), 3.02 (m, 1H), 3.42 (m, 1H), 3.66 (dd, J=4,13, 1H), 7.0–7.3 (m, 9H).

$^{13}$C-NMR ($\delta$, DMSO-$d_6$): 24.1, 32.7, 41.3, 42.3, 48.3, 114.9, 115.1, 126.0, 127.7, 128.5, 128.6, 128.9, 141.5, 142.0, 158.7, 159.12, 162.3.

5-(4-Fluorophenyl)-7-phenyl-hexahydroazepin-2-one

Prepared as a light yellow foam in 53% yield.

$^1$H-NMR ($\delta$, $CDCl_3$): 1.8–2.2 (m, 4H), 2.70 (m, 2H), 2.93 (m, 1H), 4.58 (m, 1H), 5.72 (bs, 1H) N<u>H</u>), 6.9–7.4 (m, 9H).

$^{13}$C-NMR ($\delta$, $CDCl_3$): 30.5, 36.2, 45.4, 46.2, 47.8, 58.0, 115.3, 115.6, 115.7, 116.0, 125.5, 126.3, 127.6, 128.0, 128.4, 129.2, 141.8, 141.9, 163.1, 176.4.

FAB MS (%): 284 (100, parent+1), 180 (37), 109 (10), 91 (11).

3-Bromo-5-(4-fluorophenyl)-7-phenyl-hexahydroazepin-2-one

Prepared as a mixture of diastereomers as a foam in 63% yield.

$^1$H-NMR ($\delta$, $CDCl_3$): 2.0–2.6 (m, 4H), 3.12 (m, 1H), 4.50 (m, 1H), 4.86 and 4.98 (multiplets for the diastereomers at the 3-position, 1H), 5.87 (bs, 1H) N<u>H</u>), 6.9–7.4 (m, 9H).

$^{13}$C-NMR ($\delta$, $CDCl_3$): 42.0, 42.6, 44.1, 46.2, 47.2, 50.3, 57.3, 57.6, 59.1, 115.5, 115.8, 126.2, 128.0, 128.1, 128.8, 129.4, 140.1, 141.0, 160.1, 163.3, 169.6.

IR (cm.$^{-1}$, KBr): 1670 (C=O).

N-(t-Butyl)-2-oxo-3-bromo-5-(4-fluorophenyl)-7-phenyl-hexahydroazepin-1-yl ethanoic amide Prepared as a mixture of diastereomers as a foam in 73% yield.

$^1$H-NMR ($\delta$, $CDCl_3$): 1.27 and 1.29 (singlets for the two diastereomers, 9H), 2.0–2.6 (m, 4H), 3.1 (m, 1H), 3.56 (m, 1H), 5.02 (m, 1H), 5.44 (m, 1H), 6.9–7.3 (m, 9H).

N-(t-Butyl)-2-oxo-3-azido-5-(4-fluorophenyl)-7-phenyl-hexahydroazepin-1-yl ethanoic amide Prepared as a mixture of diasterteomers as a foam in 77% yield.

$^1$H-NMR ($\delta$, $CDCl_3$): 1.28 and 1.36 (singlets, 9H), 2.0–2.3 (m, 3H), 2.5 (m, 1H), 3.10 (m, 1H), 3.51 and 3.79 ($AB_q$'s, $J_{AB}$=15, Dn=238 and 326, 2H), 4.1 and 4.52 (multiplets, 1H), 4.90 and 5.09 (multiplets, 1H), 5.50 and 5.90 (singlets, 1H), 6.9–7.5 (m, 9H).

$^{13}$C-NMR ($\delta$, $CDCl_3$): 28.7, 28.8, 37.1, 37.6, 39.2, 40.5, 45.4, 48.3, 51.5, 52.1, 60.9, 61.2, 62.0, 115.5, 115.8, 125.9, 128.1, 128.3, 128.4, 128.8, 129.0, 129.4, 137.9, 140.1, 167.5, 170.7, 172.2.

N-(t-Butyl)-2-oxo-3-amino-5-(4-fluorophenyl)-7-phenyl-hexahydroazepin-1-yl ethanoic amide Prepared as a foam in 34% yield.

$^1$H-NMR ($\delta$, $CD_3OD$): 1.21 (s, 9H), 2.0–2.3 (m, 3H), 2.70 (m, 1H), 3.30 (bs over a multiplet, 3H), 3.73 ($AB_q$, $J_{AB}$=17, Dn=178, 2H), 4.80 (d, J=11, 1H), 5.23 (d, J=11, 1H), 6.9–7.4 (m, 9H).

N-(t-Butyl)-2-oXo-3-(3-tolylureido)-5-(4-fluorophenyl)-7-phenyl-hexahydroazepin-1-yl ethanoic amide Prepared as an amorphous solid in 62% yield.

$^1$H-NMR ($\delta$, $CDCl_3$,TFA): 1.20 (s, 9H), 1.9–2.4 (m, 4H), 2.33 (s, 3H), 3.26 (m, 1H), 3.8–4.0 (m, 3H), 5.23 (m, 1H), 5.37 (m, 1H), 6.9–7.5 (m, 15H).

EXAMPLE 119

N-(t-Butyl)-2-oxo-3-(3-chlorophenylureido)-5-(4-fluorophenyl)-7-phenyl-hexahydroazepin-1-yl ethanoic amide Prepared from N-(t-butyl)-2-oxo-3-amino-5-(4-fluorophenyl)-7-phenyl-hexahydroazepin-1-yl ethanoic amide as in Example 118 as an amorphous solid in 54.5% yield.

$^1$H-NMR ($\delta$, $CDCl_3$,TFA): 1.20 (s, 9H), 2.00 (m, 1H), 2.2–2.5 (m, 3H), 3.29 (m, 1H), 3.86 (m, 1H), 3.91 ($AB_q$, $J_{AB}$=16, Dn=42, 2H), 5.25 (d, J=11, 1H), 5.41 (d, J=11, 1H), 6.9–7.4 (m, 15H).

EXAMPLE 120

N-(t-Butyl)-2-oxo-3-(3-methoxyphenylureido)-5-(4-fluorophenyl)-7-phenyl-hexahydroazepin-1-yl ethanoic amide Prepared from N-(t-butyl)-2-oxo-3-amino-5-(4-fluorophenyl)-7-phenyl-hexahydroazepin-1-yl ethanoic amide as in Example 118 as an amorphous solid in 55% yield.

$^1$H-NMR ($\delta$, $CDCl_3$,TFA): 1.19 (s, 9H), 1.97 (m, 1H), 2.2–2.5 (m, 3H), 3.29 (m, 1H), 3.82 (s, 3H), 3.83 (m, 1H), 3.92 ($AB_q$, $J_{AB}$=17, Dn=51, 2H), 5.23 (d, J=11, 1H), 5.38 (d, J=11, 1H), 6.7–7.4 (m, 15H).

I claim:
1. A compound of the formula

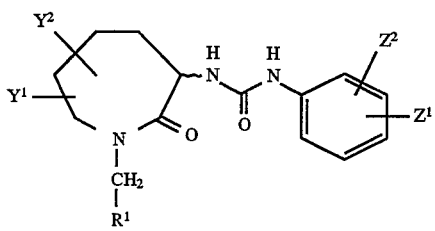

wherein $Y^1$ and $Y^2$ are independently selected from the group consisting of phenyl, thienyl, pyridyl, furyl, pyrimidyl, ($C_3$–$C_8$) straight or branched alkyl and ($C_5$–$C_8$) cycloalkyl, wherein said phenyl, thienyl, pyridyl, furyl and pyrimidyl may optionally substituted with one or two substituents independently selected from the group consisting of halo ($C_1$–$C_6$) alkyl, ($C_1$–$C_6$) alkoxy, nitro, amino and trifluoromethyl, and wherein said cycloalkyl may optionally be substituted with one or two substituents independently selected from ($C_1$–$C_6$) alkyl;

$Z^1$ and $Z^2$ are independently selected from the group consisting of halo, ($C_1$–$C_6$) alkyl, ($C_1$–$C_6$) thioalkyl, ($C_1$–$C_6$) alkoxy, trifluoromethyl, ($C_1$–$C_6$) carboalkoxy, amino and nitro;

$R^1$ is phenyl, $CO_2R^2$, $SO_2NR^3R^6$ or $CONR^4R^5$, wherein said phenyl may optionally be substituted with one or two substituents independently selected from the group consisting of halo, ($C_1$–$C_6$) alkyl, ($C_1$–$C_6$) alkoxy, nitro, amino and trifluoromethyl, and wherein $R^2$, $R^3$, $R^4$ and $R^5$ are independently selected from hydrogen, ($C_3$–$C_{12}$) alkyl and fused, saturated, carbocyclic systems containing two or three rings;

or a pharmaceutically acceptable salt thereof $R^1$ is phenyl, $CO_2R^2$, $SO_2NR^3R^6$ or $CONR^4R^5$, wherein said phenyl may optionally be substituted with one or two substituents independently selected from the group consisting of halo, ($C_1$–$C_6$) alkyl, ($C_1$–$C_6$) alkoxy, nitro, amino and trifluoromethyl, and wherein $R^2$, $R^3$, $R^4$ and $R^5$ are independently selected from hydrogen, ($C_3$–$C_{12}$) alkyl and fused, saturated, carbocyclic systems containing two or three rings;

or a pharmaceutically acceptable salt thereof.

2. A compound according to claim 1, wherein said compound is a compound of the formula I wherein either both of $Y^1$ and $Y^2$ are phenyl or one of $Y^1$ and $Y^2$ is cyclohexyl, or a pharmaceutically acceptable salt of said compound.

3. A compound according to claim 1, wherein said compound is selected from the group consisting of:

3-((3-chlorophenyl)ureido)-7-cyclohexyl-(N-t-butoxycarbonylmethyl)-hexahydroazepin-2-one;

3-((3-tolyl)ureido)-7-cyclohexyl-(N-t-butoxycarbonylmethyl)hexahydroazepin-2-one;

3-((3-chlorophenyl)ureido)-7-cyclohexyl-(N-1-adamantyloxycarbonylmethyl)-hexahydroazepin-2-one;

3-((3-chlorophenyl)ureido)-7-cyclohexyl-(N-2-adamantyloxycarbonylmethyl)-hexahydroazepin-2-one;

3-((3-tolyl)ureido)-7-cyclohexyl-(N-1-adamantyloxycarbonylmethyl)-hexahydroazepin-2-one;

3-((3-tolyl)ureido)-7-cyclohexyl-(N-2-adamantyloxycarbonylmethyl)-hexahydroazepin-2-one;

3-((3-methoxyphenyl)ureido)-7-cyclohexyl-(N-t-butoxycarbonylmethyl)-hexahydroazepin-2-one;

3-((3-methoxyphenyl)ureido)-7-cyclohexyl-(N-1-adamantyloxycarbonylmethyl)-hexahydroazepin-2-one;

3-((3-methoxyphenyl)ureido)-7-cyclohexyl-(N-2-adamantyloxycarbonylmethyl)-hexahydroazepin-2-one;

3-((3-chlorophenyl)ureido)-5,7-diphenyl-(N-t-butoxycarbonylmethyl)-hexahydroazepin-2-one;

3-((3-tolyl)ureido)-5,7-diphenyl-(N-t-butoxycarbonylmethyl)-hexahydroazepin-2-one;

3-((3-methoxyphenyl)ureido)-5,7-diphenyl-(N-t-butoxycarbonylmethyl)-hexahydroazepin-2-one;

3-((3-chlorophenyl)ureido)-5,7-diphenyl-(N-1-adamantyloxycarbonylmethyl)-hexahydroazepin-2-one;

N-tert-butyl-2-[2-oxo-3-((3-tolyl)ureido)-5,7-diphenyl-hexahydroazepin-1-yl]-ethanoic acid amide;

N-tert-butyl-2-[2-oxo-3-((3-chlorophenyl)ureido)-5,7-diphenylhexahydroazepin-1-yl]ethanoic acid amide;

N-tert-butyl-2-[2-oxo-3-((3-methoxyphenyl)ureido)-5,7-diphenylhexahydroazepin-1-yl]ethanoic acid amide;

N-tert-butyl-2-[2-oxo-3-((3-trifluoromethylphenyl)ureido)-5,7-diphenylhexahydroazepin-1-yl]ethanoic acid amide;

N-tert-butyl-2-[2-oxo-3-((3-methylthiophenyl)ureido)-5,7-diphenyl-hexahydroazepin-1-yl]ethanoic acid amide;

N-tert-butyl-2-[2-oxo-3-((3-cyanophenyl)ureido)-5,7-diphenyl-hexahydroazepin-1-yl]ethanoic acid amide;

N-tert-butyl-2-[2-oxo-3-((3-dimethylaminophenyl)ureido)-5,7-diphenyl-hexahydroazepin-1-yl]ethanoic acid amide; and N-tert-butyl-2-[2-oxo-3-((3-ethylphenyl)ureido)-5,7-diphenyl-hexahydroazepin-1-yl]ethanoic acid amide.

4. A pharmaceutical composition for treating or preventing a condition selected from the group consisting of pain, gastrointestinal disorders such as ulcer and colitis, and central nervous system disorders such as anxiety and panic disorder in a mammal, comprising an amount of a compound according to claim 1 effective in preventing or treating such condition and a pharmaceutically acceptable carrier.

5. A method of treating or preventing a condition selected from the group consisting of pain, gastrointestinal disorders such as ulcer and colitis, and central nervous system disorders such as anxiety and panic disorder in a mammal, comprising administering to a mammal in need of such treatment or prevention an amount of a compound according to claim 1 effective in treating or preventing such condition.

6. A pharmaceutical composition for antagonizing the effects of cholecystokinin in a mammal, comprising a CCK-B antagonizing effective amount of a compound according to claim 1 and a pharmaceutically acceptable carrier.

7. A method of antagonizing the effects of cholecystokinin in a mammal, comprising administering to said mammal a CCK-B antagonizing effective amount of a compound according to claim 1.

* * * * *